(12) United States Patent
Dubridge et al.

(10) Patent No.: US 10,849,973 B2
(45) Date of Patent: *Dec. 1, 2020

(54) PROSTATE SPECIFIC MEMBRANE ANTIGEN BINDING PROTEIN

(71) Applicant: Harpoon Therapeutics, Inc., South San Francisco, CA (US)

(72) Inventors: Robert Dubridge, Belmont, CA (US); Pui Seto, San Carlos, CA (US); Patrick Baeuerle, Gauting (DE); Jeanmarie Guenot, San Francisco, CA (US); Holger Wesche, San Francisco, CA (US); Bryan D. Lemon, Mountain View, CA (US); Richard J. Austin, San Francisco, CA (US)

(73) Assignee: HARPOON THERAPEUTICS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/821,498

(22) Filed: Nov. 22, 2017

(65) Prior Publication Data

US 2018/0161428 A1 Jun. 14, 2018

Related U.S. Application Data

(60) Provisional application No. 62/426,086, filed on Nov. 23, 2016.

(51) Int. Cl.

| | |
|---|---|
| *A61K 39/00* | (2006.01) |
| *A61K 39/395* | (2006.01) |
| *A61P 35/00* | (2006.01) |
| *A61K 38/17* | (2006.01) |
| *C07K 16/30* | (2006.01) |
| *C07K 16/18* | (2006.01) |
| *C07K 16/28* | (2006.01) |
| *A61K 38/00* | (2006.01) |

(52) U.S. Cl.
CPC .... *A61K 39/39558* (2013.01); *A61K 38/1764* (2013.01); *A61K 39/001195* (2018.08); *A61P 35/00* (2018.01); *C07K 16/18* (2013.01); *C07K 16/2809* (2013.01); *C07K 16/2863* (2013.01); *C07K 16/3069* (2013.01); *A61K 38/00* (2013.01); *A61K 2039/505* (2013.01); *C07K 2317/31* (2013.01); *C07K 2317/565* (2013.01); *C07K 2317/569* (2013.01); *C07K 2317/622* (2013.01); *C07K 2317/73* (2013.01); *C07K 2317/92* (2013.01); *C07K 2317/94* (2013.01)

(58) Field of Classification Search
CPC ............................................... A61K 2039/505
See application file for complete search history.

(56) References Cited

U.S. PATENT DOCUMENTS

| | | |
|---|---|---|
| 4,816,567 A | 3/1989 | Cabilly et al. |
| 5,061,620 A | 10/1991 | Tsukamoto et al. |
| 5,199,942 A | 4/1993 | Gillis |
| 5,225,539 A | 7/1993 | Winter |
| 5,350,674 A | 9/1994 | Boenisch et al. |
| 5,399,346 A | 3/1995 | Anderson et al. |
| 5,530,101 A | 6/1996 | Queen et al. |
| 5,565,332 A | 10/1996 | Hoogenboom et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,759,808 A | 6/1998 | Casterman et al. |
| 5,766,886 A | 6/1998 | Studnicka et al. |
| 5,773,292 A | 6/1998 | Bander |
| 5,800,988 A | 9/1998 | Casterman et al. |
| 5,840,526 A | 11/1998 | Casterman et al. |
| 5,858,358 A | 1/1999 | June et al. |
| 5,859,205 A | 1/1999 | Adair et al. |
| 5,874,541 A | 2/1999 | Casterman et al. |
| 5,883,223 A | 3/1999 | Gray |
| 6,005,079 A | 12/1999 | Casterman et al. |
| 6,015,695 A | 1/2000 | Casterman et al. |
| 6,107,090 A | 8/2000 | Bander |
| 6,120,766 A | 9/2000 | Hale et al. |
| 6,136,311 A | 10/2000 | Bander |
| 6,326,193 B1 | 12/2001 | Liu et al. |
| 6,331,415 B1 | 12/2001 | Cabilly et al. |
| 6,352,694 B1 | 3/2002 | June et al. |
| 6,407,213 B1 | 6/2002 | Carter et al. |
| 6,534,055 B1 | 3/2003 | June et al. |

(Continued)

FOREIGN PATENT DOCUMENTS

| | | |
|---|---|---|
| CN | 1563092 A | 1/2005 |
| CN | 101646689 A | 2/2010 |

(Continued)

OTHER PUBLICATIONS

Foote et al. (J. Mol. Biol. Mar. 20, 1992; 224 (2): 487-99).*
Mariuzza et al. (Annu. Rev. Biophys. Biophys. Chem. 1987; 16: 139-159).*
Rudikoff et al. (Proc. Natl. Acad. Sci. USA. 1982; 79: 1979-1983).*
Winkler et al. (J. Immunol. Oct. 15, 2000; 165 (8): 4505-4514).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*

(Continued)

*Primary Examiner* — Stephen L Rawlings
(74) *Attorney, Agent, or Firm* — Wilson Sonsini Goodrich & Rosati

(57) ABSTRACT

Disclosed herein are PSMA binding proteins with improved binding affinities, and robust aggregation profiles. Also described are multispecific binding proteins comprising a PSMA binding protein according to the instant disclosure. Pharmaceutical compositions comprising the binding proteins disclosed herein and methods of using such formulations are further provided.

8 Claims, 18 Drawing Sheets

Specification includes a Sequence Listing.

(56) References Cited

U.S. PATENT DOCUMENTS

| | | |
|---|---|---|
| 6,548,640 B1 | 4/2003 | Winter |
| 6,670,453 B2 | 12/2003 | Frenken et al. |
| 6,692,964 B1 | 2/2004 | June et al. |
| 6,759,518 B1 | 7/2004 | Kontermann et al. |
| 6,767,711 B2 | 7/2004 | Bander |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,163,680 B2 | 1/2007 | Bander |
| 7,172,869 B2 | 2/2007 | June et al. |
| 7,175,843 B2 | 2/2007 | June et al. |
| 7,232,566 B2 | 6/2007 | June et al. |
| 7,262,276 B2 | 8/2007 | Huang et al. |
| 7,666,414 B2 | 2/2010 | Bander |
| 7,807,162 B2 | 10/2010 | Silence |
| 7,850,971 B2 | 12/2010 | Maddon et al. |
| 8,114,965 B2 | 2/2012 | Maddon et al. |
| 8,188,223 B2 | 5/2012 | Beirnaert et al. |
| 8,236,308 B2 | 8/2012 | Kischel et al. |
| 8,470,330 B2 | 6/2013 | Schuelke et al. |
| 8,623,356 B2 | 1/2014 | Christopherson et al. |
| 8,629,244 B2 | 1/2014 | Kolkman et al. |
| 8,703,135 B2 | 4/2014 | Beste et al. |
| 8,784,821 B1 | 7/2014 | Kufer et al. |
| 8,846,042 B2 | 9/2014 | Zhou |
| 8,907,071 B2 | 12/2014 | Sullivan et al. |
| 8,937,164 B2 | 1/2015 | Descamps et al. |
| 9,169,316 B2 | 10/2015 | Baty et al. |
| 9,309,327 B2 | 4/2016 | Humphreys et al. |
| 9,327,022 B2 | 5/2016 | Zhang et al. |
| 9,340,621 B2 | 5/2016 | Kufer et al. |
| 9,708,412 B2 * | 7/2017 | Baeuerle .............. C07K 16/468 |
| 10,428,120 B2 | 10/2019 | Kontermann et al. |
| 2005/0042664 A1 | 2/2005 | Wu et al. |
| 2005/0048617 A1 | 3/2005 | Wu et al. |
| 2005/0100543 A1 | 5/2005 | Hansen et al. |
| 2005/0175606 A1 | 8/2005 | Huang et al. |
| 2006/0046971 A1 | 3/2006 | Stuhler et al. |
| 2006/0121005 A1 | 6/2006 | Berenson et al. |
| 2006/0228364 A1 | 10/2006 | Dennis et al. |
| 2006/0252096 A1 | 11/2006 | Zha et al. |
| 2007/0014794 A1 | 1/2007 | Carter et al. |
| 2007/0178082 A1 | 8/2007 | Silence et al. |
| 2007/0269422 A1 | 11/2007 | Beirnaert et al. |
| 2008/0069772 A1 | 3/2008 | Stuhler et al. |
| 2008/0260757 A1 | 10/2008 | Holt et al. |
| 2009/0259026 A1 | 10/2009 | Tomlinson et al. |
| 2010/0122358 A1 | 5/2010 | Brueggemann et al. |
| 2010/0150918 A1 | 6/2010 | Kufer et al. |
| 2010/0166734 A1 | 7/2010 | Dolk |
| 2010/0189727 A1 | 7/2010 | Rodeck et al. |
| 2010/0266531 A1 | 10/2010 | Hsieh et al. |
| 2010/0291112 A1 | 11/2010 | Kellner et al. |
| 2011/0129458 A1 | 6/2011 | Dolk et al. |
| 2011/0165621 A1 | 7/2011 | Dreier et al. |
| 2011/0262439 A1 | 10/2011 | Kufer et al. |
| 2011/0275787 A1 | 11/2011 | Kufer et al. |
| 2011/0313135 A1 | 12/2011 | Vanhove et al. |
| 2012/0231024 A1 | 9/2012 | Elsaesser-Beile et al. |
| 2012/0328619 A1 | 12/2012 | Fey et al. |
| 2013/0017200 A1 | 1/2013 | Scheer et al. |
| 2013/0136744 A1 | 5/2013 | Bouche et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0330335 A1 | 12/2013 | Bremel et al. |
| 2014/0004121 A1 | 1/2014 | Fanslow, III et al. |
| 2014/0023664 A1 | 1/2014 | Lowman et al. |
| 2014/0045195 A1 | 2/2014 | Daugherty et al. |
| 2014/0073767 A1 | 3/2014 | Lee et al. |
| 2014/0088295 A1 | 3/2014 | Smith et al. |
| 2014/0205601 A1 | 7/2014 | Beirnaert et al. |
| 2014/0242075 A1 | 8/2014 | Parren et al. |
| 2014/0302037 A1 | 10/2014 | Borges et al. |
| 2014/0322218 A1 | 10/2014 | Xiao et al. |
| 2015/0037334 A1 | 2/2015 | Kufer et al. |
| 2015/0056206 A1 | 2/2015 | Zhou |
| 2015/0064169 A1 | 3/2015 | Wang et al. |
| 2015/0079088 A1 | 3/2015 | Lowman et al. |
| 2015/0079093 A1 | 3/2015 | Stuhler |
| 2015/0093336 A1 | 4/2015 | Van Ginderachter et al. |
| 2015/0174268 A1 | 6/2015 | Li et al. |
| 2015/0183875 A1 | 7/2015 | Cobbold et al. |
| 2015/0232557 A1 | 8/2015 | Tan et al. |
| 2015/0274836 A1 | 10/2015 | Ho et al. |
| 2015/0274844 A1 | 10/2015 | Blankenship et al. |
| 2016/0024174 A1 | 1/2016 | Odunsi et al. |
| 2016/0032019 A1 | 2/2016 | Xiao et al. |
| 2016/0039942 A1 | 2/2016 | Cobbold et al. |
| 2016/0068605 A1 | 3/2016 | Nemeth et al. |
| 2016/0130331 A1 | 5/2016 | Stull et al. |
| 2016/0215063 A1 | 7/2016 | Bernett et al. |
| 2016/0251440 A1 | 9/2016 | Roobrouck et al. |
| 2016/0257721 A1 | 9/2016 | Lieber et al. |
| 2016/0319040 A1 | 11/2016 | Dreier et al. |
| 2016/0340444 A1 * | 11/2016 | Baeuerle .............. C07K 16/468 |
| 2016/0355842 A1 | 12/2016 | Parks et al. |
| 2017/0029502 A1 | 2/2017 | Raum et al. |
| 2017/0152316 A1 | 6/2017 | Cobbold et al. |
| 2017/0204164 A1 | 7/2017 | Himmler et al. |
| 2017/0275373 A1 | 9/2017 | Kufer et al. |
| 2017/0298149 A1 | 10/2017 | Baeuerle et al. |
| 2017/0334979 A1 | 11/2017 | Dubridge et al. |
| 2017/0334997 A1 | 11/2017 | Dubridge et al. |
| 2017/0369563 A1 | 12/2017 | Dubridge et al. |
| 2017/0369575 A1 | 12/2017 | Dubridge et al. |
| 2018/0016323 A1 | 1/2018 | Brandenburg et al. |
| 2018/0134789 A1 | 5/2018 | Baeuerle et al. |
| 2018/0148508 A1 | 5/2018 | Wang et al. |
| 2019/0225702 A1 | 7/2019 | Baeuerle et al. |
| 2020/0095340 A1 | 3/2020 | Wesche et al. |
| 2020/0115461 A1 | 4/2020 | Evnin et al. |
| 2020/0148771 A1 | 5/2020 | Baeuerle et al. |

FOREIGN PATENT DOCUMENTS

| | | |
|---|---|---|
| EP | 0239400 A2 | 9/1987 |
| EP | 0519596 A1 | 12/1992 |
| EP | 0592106 A1 | 4/1994 |
| EP | 1378520 A1 | 1/2004 |
| EP | 1736484 A1 | 12/2006 |
| EP | 2336179 A1 | 6/2011 |
| FR | 901228 A | 7/1945 |
| JP | 2005501517 A | 1/2005 |
| WO | WO-9109967 A1 | 7/1991 |
| WO | WO-9307105 A1 | 4/1993 |
| WO | WO-9404678 A1 | 3/1994 |
| WO | WO-9937681 A2 | 7/1999 |
| WO | WO-0043507 A1 | 7/2000 |
| WO | WO-0190190 A2 | 11/2001 |
| WO | WO-0196584 A2 | 12/2001 |
| WO | WO-02085945 A2 | 10/2002 |
| WO | WO-03025020 A1 | 3/2003 |
| WO | WO-03035694 A2 | 5/2003 |
| WO | WO-03064606 A2 | 8/2003 |
| WO | WO-2004003019 A2 | 1/2004 |
| WO | WO-2004041867 A2 | 5/2004 |
| WO | WO-2004042404 A1 | 5/2004 |
| WO | WO-2004049794 A2 | 6/2004 |
| WO | WO-2006020258 A2 | 2/2006 |
| WO | WO-2006122787 A1 | 11/2006 |
| WO | WO-2007024715 A2 | 3/2007 |
| WO | WO-2007042261 A2 | 4/2007 |
| WO | WO-2007062466 A1 | 6/2007 |
| WO | WO-2007115230 A2 | 10/2007 |
| WO | WO-2008028977 A2 | 3/2008 |
| WO | WO-2009025846 A2 | 2/2009 |
| WO | WO-2009030285 A1 | 3/2009 |
| WO | WO-2009147248 A2 | 12/2009 |

(56) References Cited

FOREIGN PATENT DOCUMENTS

| | | |
|---|---|---|
| WO | WO-2010003118 A1 | 1/2010 |
| WO | WO-2010037836 A2 | 4/2010 |
| WO | WO-2010037837 A2 | 4/2010 |
| WO | WO-2011039368 A2 | 4/2011 |
| WO | WO-2011051327 A2 | 5/2011 |
| WO | WO-2012131053 A1 | 10/2012 |
| WO | WO-2012138475 A1 | 10/2012 |
| WO | WO-2012158818 A2 | 11/2012 |
| WO | WO-2013036130 A1 | 3/2013 |
| WO | WO-2013104804 A2 | 7/2013 |
| WO | WO-2013110531 A1 | 8/2013 |
| WO | WO-2013128027 A1 | 9/2013 |
| WO | WO-2014033304 A2 | 3/2014 |
| WO | WO-2014138306 A1 | 9/2014 |
| WO | WO-2014140358 A1 | 9/2014 |
| WO | WO-2014151910 A1 | 9/2014 |
| WO | WO-2015103072 A1 | 7/2015 |
| WO | WO-2015150447 A1 | 10/2015 |
| WO | WO-2015184207 A1 | 12/2015 |
| WO | WO-2016009029 A1 | 1/2016 |
| WO | WO-2016034044 A1 | 3/2016 |
| WO | WO-2016046778 A1 | 3/2016 |
| WO | WO-2016055551 A1 | 4/2016 |
| WO | WO-2016105450 A2 | 6/2016 |
| WO | WO-2016130819 A2 | 8/2016 |
| WO | WO-2016171999 A2 | 10/2016 |
| WO | WO-2016179003 A1 | 11/2016 |
| WO | WO-2016187101 A2 | 11/2016 |
| WO | WO-2016187594 A1 | 11/2016 |
| WO | WO-2016210447 A1 | 12/2016 |
| WO | WO-2017025698 A1 | 2/2017 |
| WO | WO-2017027392 A1 | 2/2017 |
| WO | WO-2017041749 A1 | 3/2017 |
| WO | WO-2017079528 A1 | 5/2017 |
| WO | WO-2017136549 A1 | 8/2017 |
| WO | WO-2017156178 A1 | 9/2017 |
| WO | WO-2017201488 A1 | 11/2017 |
| WO | WO-2017201493 A1 | 11/2017 |
| WO | WO-2018017863 A1 | 1/2018 |
| WO | WO-2018071777 A1 | 4/2018 |
| WO | WO-2018098354 A1 | 5/2018 |
| WO | WO-2018098356 A1 | 5/2018 |
| WO | WO-2018136725 A1 | 7/2018 |
| WO | WO-2018160671 A1 | 9/2018 |
| WO | WO-2018160754 A2 | 9/2018 |
| WO | WO-2018165619 A1 | 9/2018 |
| WO | WO-2018204717 A1 | 11/2018 |
| WO | WO-2018209298 A1 | 11/2018 |
| WO | WO-2018209304 A1 | 11/2018 |
| WO | WO-2019075359 A1 | 4/2019 |
| WO | WO-2019075378 A1 | 4/2019 |
| WO | WO-2019222278 A1 | 11/2019 |
| WO | WO-2019222282 A1 | 11/2019 |
| WO | WO-2019222283 A1 | 11/2019 |
| WO | WO-2020060593 A1 | 3/2020 |
| WO | WO-2020061482 A1 | 3/2020 |
| WO | WO-2020061526 A1 | 3/2020 |
| WO | WO-2020069028 A1 | 4/2020 |

OTHER PUBLICATIONS

Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Connnnun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Saerens et al. (J. Mol. Biol. Sep. 23, 2005; 352 (3): 597-607).*
Vincke et al. (J. Biol. Chem. Jan. 30, 2009; 284 (5): 3273-84).*
Goldman et al. (Front. Immunol. Jul. 25, 2017; 8: 865; pp. 1-11).*
Tiller et al. (Front. Immunol. 2017; 8: 986; pp. 1-16).*
Su et al. (Cancer Lett. Sep. 28, 2013; 338 (2): 282-91).*
Zare et al. (Int. J. Biol. Markers. Jun. 25, 2014; 29 (2): e169-79; pp. 1-11).*
Schmidt et al. (Prostate. May 2013; 73 (6): 642-500).*
Schmittgen et al. (Int. J. Cancer. Nov. 1, 2003; 107 (2): 323-9).*
Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).
Bortoletto et al. Optimizing anti-CD3 affinity for effective T cell targeting against tumor cells. Eur J Immunol 32:3102-3107 (2002).
Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).
Chang et al. Molecular cloning of mesothelin, a differentiation antigen present on mesothelium, mesotheliomas, and ovarian cancers. PNAS USA 93:136-140 (1996).
Co-pending U.S. Appl. No. 15/977,968, filed May 11, 2018.
Co-pending U.S. Appl. No. 15/977,988, filed May 11, 2018.
Corso et al. Real-time detection of mesothelin in pancreatic cancer cell line supernatant using an acoustic wave immunosensor. Cancer Detect Prev 30:180-187 (2006).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
Document D28—Investigation of human CD3ε variants binding to monoclonal antibodies. Submitted by Pfizer to the European Patent Register on Apr. 30, 2014 in connection with their opposition to the EP2155783 patent. (3 pages) (2014).
Document D78—CD3ε N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ε and SP34 CDR residues. CD3ε residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).
Gross et al. Endowing T cells with antibody specificity using chimeric T cell receptors. FASEB J. 6(15):3370-3378 (1992).
Gubbels et al. Mesothelin-MUC16 binding is a high affinity, N-glycan dependent interaction that facilitates peritoneal metastasis of ovarian tumors. Mol Cancer 5:50 (2006).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prev 15:1014-1020 (2006).
Ho et al. A novel high-affinity human monoclonal antibody to mesothelin. Int J Cancer 128:2020-2030 (2011).

(56) References Cited

OTHER PUBLICATIONS

Ho et al. Mesothelin expression in human lung cancer. Clin Cancer Res 13:1571-1575 (2007).
Janssen letter—Submission under Rule 116 EPC. Submitted by Janssen Biotech to the European Patent Register on Mar. 18, 2016 in connection with their opposition to the EP2155783 patent (6 pages) (2016).
Kojima et al. Molecular cloning and expression of megakaryocyte potentiating factor cDNA. J Biol Chem 270:21984-21990 (1995).
Li et al. Development of novel tetravalent anti-CD20 antibodies with potent antitumor activity. Cancer Res 68:2400-2408 (2008).
Mirsky et al. Antibody-Specific Model of Amino Acid Substitution for Immunological Inferences from Alignments of Antibody Sequences. Mol. Biol. Evol. 32(3):806-819 (2014).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Muul et al. Persistence and expression of the adenosine deaminase gene for 12 years and immune reaction to gene transfer components: long-term results of the first clinical gene therapy trial. Blood 101(7):2563-2569 (2003).
Ordonez. Application of mesothelin immunostaining in tumor diagnosis. Am J Surg Pathol 27:1418-1428 (2003).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX. J Immunol 183:749-758 (2009).
PCT/US2018/020185 International Search Report and Written Opinion dated Jun. 15, 2018.
PCT/US2018/020307 International Search Report and Written Opinion dated Aug. 24, 2018.
PCT/US2018/030983 Invitation to Pay Additional Fees dated Jul. 31, 2018.
PCT/US2018/032427 International Search Report and Written Opinion dated Sep. 13, 2018.
PCT/US2018/32418 Invitation to Pay Additional Fees dated Jul. 23, 2018.
PCT/US2018/32427 Invitation to Pay Additional Fees dated Jul. 24, 2018.
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Rump et al. Binding of ovarian cancer antigen CA125/MUC16 to mesothelin mediates cell adhesion. J Biol Chem 279:9190-9198 (2004).
Sadelain et al. Targeting tumours with genetically enhanced T lymphocytes. Nat Rev Cancer 3(1):35-45 (2003).
Schmittgen et al. Expression of prostate specific membrane antigen and three alternatively spliced variants of PSMA in prostate cancer patients. Int J Cancer 107:323-329 (2003).
Tang et al. A human single-domain antibody elicits potent antitumor activity by targeting an epitope in mesothelin close to the cancer cell surface. Mol. Cancer Thera 12(4):416-426 (2013).
Thomas et al. Mesothelin-specific CD8(+) T cell responses provide evidence of in vivo cross-priming by antigen-presenting cells in vaccinated pancreatic cancer patients. J Exp Med 200:297-306 (2004).
U.S. Appl. No. 15/600,264 Office Action dated Apr. 26, 2018.
U.S. Appl. No. 15/821,530 Office Action dated Sep. 25, 2018.
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Holt et al. Anti-serum albumin domain antibodies for extending the half-lives of short lived drugs. Protien Eng Des Sel 21(5):283-288 (2008).
Liu et al. MGD011, a CD19 x CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Nelson et al. Antibody fragments Hope and Hype. mAbs 2(1):77-83 (2010).
PCT/US2017/063121 International Search Report and Written Opinion dated Mar. 26, 2018.
PCT/US2017/063126 International Search Report and Written Opinion dated Apr. 5, 2018.
PCT/US2017056530 International Search Report and Written Opinion dated Jan. 23, 2018.
PCT/US2017/063121 Invitation to Pay Additional Fees dated Feb. 1, 2018.
PCT/US2017/063126 Invitation to Pay Additional Fees dated Feb. 1, 2018.
Almagro et al. Humanization of antibodies. Front Biosci 13:1619-1633 (2008).
Baca et al. Antibody humanization using monovalent phage display. J Biol Chem 272(16):10678-10684 (1997).
Baeuerle et al. Bispecific T-cell engaging antibodies for cancer therapy. Cancer Res 69:4941-4944 (2009).
Bedouelle et al. Diversity and junction residues as hotspots of binding energy in an antibody neutralizing the dengue virus. FEBS J 273(1):34-46 (2006).
Brown et al. Tolerance of single, but not multiple, amino acid replacements in antibody VH CDR 2: a means of minimizing B cell wastage from somatic hypermutation? J Immunol 156(9):3285-3291 (1996).
Carter et al. Humanization of an anti-p185HER2 antibody for human cancer therapy. PNAS USA 89(10):4285-4289 (1992).
Casset et al. A peptide mimetic of an anti-CD4 monoclonal antibody by rational design. Biochemical and Biophysical Research Communication 307:198-205 (2003).
Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Selection and analysis of an optimized anti-VEGF antibody: Crystal structure of an affinity-matured Fab in complex with antigen. J Mol Bio 293:865-881 (1999).
Chothia et al. Canonical structures for the hypervariable regions of immunoglobulins. J Mol Biol 196(4):901-917 (1987).
Co-pending U.S. Appl. No. 15/821,530, filed Nov. 22, 2017.
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Frankel et al. Targeting T cells to tumor cells using bispecific antibodies. Curr Opin Chem Biol 17(3):385-392 (2013).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Harding et al. The immunogenicity of humanized and fully human antibodies: residual immunogenicity resides in the CDR regions. MAbs 2(3):256-265 (2010).
Hutchinson et al. Mutagenesis at a specific position in a DNA sequence. J Biol Chem 253:6551-6560 (1978).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Le Gall et al. Immunosuppressive properties of anti-CD3 single-chain Fv and diabody. J Immunol Methods 285(1):111-127 (2004).
Lutterbuese et al. T cell-engaging BiTE antibodies specific for EGFR potently eliminate KRAS- and BRAF-mutated colorectal cancer cells. PNAS 107:12605-12610 (2007).
Maccallum et al. Antibody-antigen interactions: contact analysis and binding site topography. J Mol Biol. 262(5):732-745 (1996).
Muller et al. Improving the pharmacokinetic properties of biologics by fusion to an anti-HSA shark VNAR domain. MAbs 4(6):673-685 (2012).

(56) References Cited

OTHER PUBLICATIONS

Nazarian et al. Characterization of bispecific T-cell Engager (BiTE) antibodies with a high-capacity T-cell dependent cellular cytotoxicity (TDCC) assay. J Biomol Screen 20:519-527 (2015).
Ohiro et al. A homogeneous and noncompetitive immunoassay based on the enhanced fluorescence resonance energy transfer by leucine zipper interaction. Anal Chem 74(22):5786-5792 (2002).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Padlan. Anatomy Of The Antibody Molecule. Mol Immunol 31(3):169-217 (1994).
Padlan et al. Structure of an antibody-antigen complex: Crystal structure of the HyHEL-10 Fab-lysozyme complex. PNAS USA 86:5938-5942 (1989).
PCT/US2016/033644 International Preliminary Report on Patentability dated Nov. 30, 2017.
PCT/US2016/33644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
Presta et al. Humanization of an antibody directed against IgE. J Immunol 151:2623-2632 (1993).
Riechmann et al. Single domain antibodies: comparison of camel VH and camelised human VH domains. J Immunol Methods 231(1-2):25-38 (1999).
Rosok et al. A Combinatorial Library Strategy for the Rapid Humanization of Anticarcinoma BR96 Fab. J Biol Chem 271:22611-22618 (1996).
Rudikoff et al. Single amino acid substitution altering antigen-binding Specificity. PNAS USA 79:1979-1983 (1982).
Sims et al. A humanized CD18 antibody can block function without cell destruction. J Immunol 151:2296-2308 (1993).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Oct. 3, 2017.
U.S. Appl. No. 15/600,582 Office Action dated Nov. 16, 2017.
U.S. Appl. No. 15/704,620 Office Action dated Oct. 26, 2017.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol Biol 310:591-601 (2001).
Vaughan et al. Human antibodies by design. Nature Biotech 16:535-539 (1998).
Wu et al. Humanization of a murine monoclonal antibody by simultaneous optimization of framework and CDR residues. J. Mol. Biol. 294:151-162 (1999).
Cho et al. Targeting B Cell Maturation Antigen (BCMA) in Multiple Myeloma: Potential Uses of BCMA-Based Immunotherapy. Front Immunol 9:1821 (2018).
PCT/US2018/055659 International Search Report and Written Opinion dated Feb. 21, 2019.
PCT/US2018/055682 International Search Report and Written Opinion dated Mar. 1, 2019.
U.S. Appl. No. 15/977,968 Office Action dated Feb. 21, 2019.
Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14-Apr. 18, 2018).
Co-pending U.S. Appl. No. 16/159,545, filed Oct. 12, 2018.
Co-pending U.S. Appl. No. 16/159,554, filed Oct. 12, 2018.
Co-pending U.S. Appl. No. 16/161,986, filed Oct. 16, 2018.
Liu et al. A New Format of Single Chain Tri-specific Antibody with Diminished Molecular Size Efficiently Induces Ovarian Tumor Cell Killing. Biotechnology Letters 27(22):1821-1827 (2005).
Lu et al. In vitro and in vivo antitumor effect of a trivalent bispecific antibody targeting ErbB2 and CD16. Cancer Biol Ther. 7(11):1744-1750 (2008).
Mueller et al. Improved pharmacokinetics of recombinant bispecific antibody molecules by fusion to human serum albumin. J Bio Chem 282(17):12650-12660 (2007).
Nunez-Prado et al. The coming of age of engineered multivalent antibodies. Drug Discovery Today 20(5):588-594 (2015).
PCT/US2018/014396 International Search Report and Written Opinion dated Jun. 14, 2018.
PCT/US2018/030983 International Search Report and Written Opinion dated Sep. 25, 2018.
PCT/US2018/032418 International Search Report and Written Opinion dated Sep. 24, 2018.
PCT/US2018/055659 Invitation to Pay Additional Fees dated Dec. 19, 2018.
PCT/US2018/055682 Invitation to Pay Additional Fees dated Jan. 8, 2019.
Running Deer et al. High-level expression of proteins in mammalian cells using transcription regulatory sequences from the Chinese hamster EF-1alpha gene. Biotechnol Prog. 20:880-889 (2004).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1-Apr. 5, 2017.
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
U.S. Appl. No. 15/600,264 Office Action dated Nov. 27, 2018.
U.S. Appl. No. 15/977,988 Preinterview First Office Action dated Jan. 25, 2019.
Wang et al. A New Recombinant Single Chain Trispecific Antibody Recruits T Lymphocytes to Kill CEA (Carcinoma Embryonic Antigen) Positive Tumor Cells In Vitro Efficiently. Journal Of Biochemistry 135(4):555-565 (2004).
Zhu et al. Combody: one-domain antibody multimer with improved avidity. Immunology And Cell Biology 88(6):667-675 (2010).
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Schmidt et al. Cloning and Characterization of Canine Prostate-Specific Membrane Antigen. The Prostate 73:642-650 (2013).
U.S. Appl. No. 15/600,264 Office Action dated Apr. 25, 2019.
U.S. Appl. No. 15/821,530 Office Action dated Apr. 3, 2019.
U.S. Appl. No. 15/977,988 Office Action dated Mar. 26, 2019.
Muyldermans. Nanobodies: natural single-domain antibodies. Annu Rev Biochem 82:775-797 (2013).
U.S. Appl. No. 16/159,545 Office Action dated Aug. 6, 2019.
PCT/US2018/014396 International Preliminary Report on Patentability dated Aug. 1, 2019.
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
U.S. Appl. No. 15/977,988 Office Action dated Aug. 20, 2019.
Chen, Xiaoying et al. Fusion protein linkers: Property, design and functionality. Advanced Drug Delivery Reviews 65:1357-1369 (2013).
Dennis et al. Imaging Tumors with an Albumin-Binding Fab, a Novel Tumor-Targeting Agent. Cancer Res 67(1):254-61 (2007).
Hipp et al. A novel BCMA/CD3 bispecific T-cell engager for the treatment of multiple myeloma induces selective lysis in vitro and in vivo. Leukemia 31(8):1743-1751 (2017).
Hopp et al. The effects of affinity and valency of an albumin-binding domain (ABD) on the half-life of a single-chain diabody-ABD fusion protein. Protein Eng. Des. Sel. 23(11):827-34 (2010).

(56) References Cited

OTHER PUBLICATIONS

Laabi et al. The BCMA gene, preferentially expressed during B lymphoid maturation, is bidirectionally transcribed. Nucleic Acids Res 22(7):1147-1154 (1994).
Müller et al. Improved Pharmacokinetics of Recombinant Bispecific Antibody Molecules by Fusion to Human Serum Albumin. J. Biol. Chem. 282(17):12650-60 (2007).
Ramadoss et al. An Anti-B Cell Maturation Antigen bispecific Antibody for Multiple Myeloma. J. Ann. Chem. Soc. 137(16):5288-91 (2015).
Smirnova et al. Identification of new splice variants of the genes BAFF and BCMA. Mol. Immunol. 45 (4):1179-83 (2008).
Spiess et al. Alternative molecular formats and therapeutic applications for bispecific antibodies. Mol. Immunol. 67(2 Pt A):95-106 (2015).
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
Tijink et al. Improved tumor targeting of anti-epidermal growth factor receptor nanobodies through albumin binding: taking advantage of modular Nanobody technology. Mol. Cancer Ther. 7(8):2288-97 (2008).
U.S. Appl. No. 16/159,554 Office Action dated Jun. 7, 2019.
Agata et al. Expression of the PD-1 antigen on the surface of stimulated mouse T and B lymphocytes. Int. Immunol 8:765-75 (1996).
Al-Lazikani et al. Standard conformations for the canonical structures of immunoglobulins. J. Mol Biology 273(4):927-948 (1997).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1977).
Barrett et al. Treatment of advanced leukemia in mice with mRNA engineered T cells. Hum Gene Ther 22:1575-1586 (2011).
Batzer et al. Enhanced evolutionary PCR using oligonucleotides with inosine at the 3'- terminus. Nucleic Acids Res. 19(18):5081 (1991).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Caldas et al. Design and synthesis of germline-based hemi-humanized single-chain Fv against the CD18 surface antigen. Protein Eng 13(5):353-360 (2000).
Carter et al. PD-1: PD-L inhibitory pathway affects both CD4(+) and CD8(+) T cells and is overcome by IL-2. Eur J Immunol 32:634-643 (2002).
Choi et al. Engineering of Immunoglobulin Fc heterodimers using yeast surface-displayed combinatorial Fc library screening. PLOS One 10(12):e0145349 (2015).
Chothia, et al. Conformations of immunoglobulin hypervariable regions. Nature 342(6252):877-83 (1989).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing antibodies with minimal positional templates. Cancer Res 55(23 Supp):5973s-5977s (1995).
Dao et al. Targeting the intracellular WT1 oncogene product with a therapeutic human antibody. Sci Transl Med 5(176):176ra33 (2013).
De Genst et al. Antibody repertoire development in camelids. Dev Comp Immunol 30(1-2):187-198 (2006).
Dong et al. B7-H1 pathway and its role in the evasion of tumor immunity. J Mol Med 81:281-287 (2003).
Elango et al. Optimized transfection of mRNA transcribed from a d(A/T)100 tail-containing vector. Biochim Biophys Res Commun 330:958-966 (2005).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).
Grupp et al. Chimeric antigen receptor-modified T cells for acute lymphoid leukemia. NEJM 368:1509-1518 (2013).
Haanen et al. Selective expansion of cross-reactive CD8(+) memory T cells by viral variants. J Exp Med 190(9):1319-1328 (1999).
Ho et al. Mesothelin is shed from tumor cells. Cancer Epidemiol Biomarkers Prev 15:1751 (2006).
Hollinger et al. "Diabodies": Small bivalent and bispecific antibody fragments . PNAS USA 90:6444 6448 (1993).
Huston et al. Protein engineering of antibody binding sites: recovery of specific activity in an anti-digoxin single-chain Fv analogue produced in *Escherichia coli*. PNAS USA 85(16):5879-5883 (1988).
Izumoto et al. Phase II clinical trial of Wilms tumor 1 peptide vaccination for patients with recurrent glioblastoma multiforme. J Neurosurg 108:963-971 (2008).
Jones et al. Replacing the complementarity-determining regions in a human antibody with those from a mouse. Nature 321:522-525 (1986).
Kabat et al. Sequences of proteins of immunological interest. NIH Publ. No. 91-3242 1:647-669 (1991).
Kalos et al. T cells with chimeric antigen receptors have potent antitumor effects and can establish memory in patients with advanced leukemia. Sci Transl Med 3(95):95ra73 (2011).
Konishi et al. B7-H1 expression on non-small cell lung cancer cells and its relationship with tumor-infiltrating lymphocytes and their PD-1 expression. Clin Cancer Res 10:5094-5100 (2004).
Latchman et al. PD-L2 is a second ligand for PD-1 and inhibits T cell activation. Nat Immunol 2:261-268 (2001).
Lowman et al. Monovalent phage display: A method for selecting variant proteins from random libraries. Methods 3:205-216 (1991).
Milone et al. Chimeric receptors containing CD137 signal transduction domains mediate enhanced survival of T cells and increased antileukemic efficacy in vivo. Mol Ther 17(8):1453-1464 (2009).
Mumtaz et al. Design of liposomes for circumventing the reticuloendothelial cells. Glycobiology 5:505-10 (1991).
Nacheva et al. Preventing nondesired RNA-primed RNA extension catalyzed by T7 RNA polymerase. Eur J Biochem 270:1458-1465 (2003).
Needleman et al. A general method applicable to the search for similarities in the amino acid sequence of two proteins. J. Mol. Biol. 48:443-453 (1970).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
Padlan. A possible procedure for reducing the immunogenicity of antibody variable domains while preserving their ligand-binding properties. Mol Immunol 28(4-5):489-498 (1991).
PCT/US2019/052206 International Search Report and Written Opinion dated Feb. 14, 2020.
PCT/US2019/052206 Invitation to Pay Additional Fees dated Dec. 23, 2019.
PCT/US2019/052270 Invitation to Pay Additional Fees dated Jan. 9, 2020.
PCT/US2019/053017 International Search Report and Written Opinion dated Jan. 31, 2020.
PCT/US2019/053017 Invitation to Pay Additional Fees dated Nov. 27, 2019.
Pearson, et al. Improved Tools for Biological Sequence Comparison. Proc. Nat'l Acad. Sci. USA. 85 (1988): 2444-48.

(56) References Cited

OTHER PUBLICATIONS

Pedersen et al. Comparison of surface accessible residues in human and murine immunoglobulin Fv domains. Implication for humanization of murine antibodies. J Mol Biol 235(3):959-973 (1994).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Presta. Antibody Engineering. Curr Op Struct Biol 2:593-596 (1992).
Riechmann et al. Reshaping human antibodies for therapy. Nature, 332.6162:323-7 (1988).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg et al. Use of tumor-infiltrating lymphocytes and interleukin-2 in the immunotherapy of patients with metastatic melanoma. A preliminary report. NEJM 319:1676 (1988).
Rossolini et al. Use of deoxyinosine-containing primers vs degenerate primers for polymerase chain reaction based on ambiguous sequence information. Mol Cell Probes 8(2):91-98 (1994).
Sadelain et al. The basic principles of chimeric antigen receptor design. Cancer Discov. 3(4):388-98 (2013).
Sandhu. A rapid procedure for the humanization of monoclonal antibodies. Gene 150(2):409-410 (1994).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
Scheraga. Predicting three-dimensional structures of oligopeptides. Rev Computational Chem 3:73-142 (1992).
Sergeeva et al. An anti-PR1/HLA-A2 T-cell receptor-like antibody mediates complement-dependent cytotoxicity against acute myeloid leukemia progenitor cells. Blood 117(16):4262-4272 (2011).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Strop. Veracity of microbial transglutaminase. Bioconjugate Chem. 25(5):855-862 (2014).
Studnicka et al. Human-engineered monoclonal antibodies retain full specific binding activity by preserving non-CDR complementarity-modulating residues. Pro Eng 7(6):805-814 (1994).

Tan et al. "Superhumanized" antibodies: reduction of immunogenic potential by complementarity-determining region grafting with human germline sequences: application to an anti-CD28. J Immunol 169:1119-1125 (2002).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Ui-Tei et al. Sensitive assay of RNA interference in *Drosophila* and Chinese hamster cultured cells using firefly luciferase gene as target. FEBS Letters 479: 79-82 (2000).
U.S. Appl. No. 15/630,259 Office Action dated Dec. 30, 2019.
U.S. Appl. No. 16/159,545 Office Action dated Dec. 2, 2019.
U.S. Appl. No. 16/159,554 Office Action dated Oct. 1, 2019.
Van Der Linden et al. Induction of immune responses and molecular cloning of the heavy chain antibody repertoire of Lama glama. J Immunol Methods 240:185-195 (2000) .
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).
Willemsen et al. A phage display selected fab fragment with MHC class I-restricted specificity for MAGE-A1 allows for retargeting of primary human T lymphocytes. Gene Ther 8(21):1601-1608 (2001).
Yan et al. Engineering upper hinge improves stability and effector function of a human IgG1. J. Biol. Chem. 287:5891 (2012).
Yoshinaga et al. Ig L-chain shuffling for affinity maturation of phage library-derived human anti-human MCP-1 antibody blocking its chemotactic activity. J Biochem 143(5):593-601 (2008).
Baum et al. Antitumor activities of PSMAxCD3 diabodies by redirected T-cell lysis of prostate cancer cells. Immunotherapy 5(1):27-38 (2013).
Co-pending U.S. Appl. No. 16/773,806, filed Jan. 27, 2020.
Co-pending U.S. Appl. No. 16/773,843, filed Jan. 27, 2020.
Co-pending U.S. Appl. No. 16/802,007, filed Feb. 26, 2020.
Harmsen et al. Properties, production, and applications of camelid single-domain antibody fragments. Appl. Microbiol. Biotechnol. 77:13-22 (2007).
U.S. Appl. No. 15/821,530 Office Action dated Apr. 22, 2020.
U.S. Appl. No. 16/583,070 Office Action dated Mar. 3, 2020.
Zabetakis et al. Contributions of the complementarity determining regions to the thermal stability of a single-domain antibody. PLoS One 8(10):e77678 (2013).
Zhang et al. New High Affinity Monoclonal Antibodies Recognize Non-Overlapping Epitopes On Mesothelin For Monitoring And Treating Mesothelioma. Sci Rep 5:9928 (2015).

\* cited by examiner

| EC50 [pM] | LNCaP | 22Rv1 |
|---|---|---|
| TRITAC™ CD3 high aff. - C324 | 10 | 35 |
| TRITAC™ CD3 med. aff. - C339 | 87 | 561 |
| TRITAC™ CD3 low aff. - C325 | 1,389 | 7,460 |

FIG. 2C

| EC50 [pM] | LNCaP | LNCaP with HSA | HSA shift |
|---|---|---|---|
| PSMA p8 TRITAC™ C362 | 20 | 43 | 2x |
| PSMA HDS TRITAC™ C363 | 10 | 21 | 2x |
| PSMA HTS TRITAC™ C364 | 1.3 | 1.3 | 1x |
| PSMA BiTE | 20 | 9 | 0.5x |

FIG. 5C

- 22Rv1 human prostate cancer xenograft study in NOD/SCID/gamma mice reconstituted with resting, primary human T cells mixed at 1:1 ratio with cancer cells

PROSTATE SPECIFIC MEMBRANE ANTIGEN BINDING PROTEIN

CROSS-REFERENCE

This application claims the benefit of U.S. Provisional Application No. 62/426,086 filed Nov. 23, 2016, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Nov. 22, 2017, is named 47517-707_201_SL.txt and is 148,650 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if set forth in their entireties.

BACKGROUND OF THE INVENTION

The present disclosure provides a prostate specific membrane antigen (PSMA) binding protein which can be used for diagnosing and treating prostate conditions and other indications correlated to expression of PSMA.

SUMMARY OF THE INVENTION

Provided herein in one embodiment is a prostate specific membrane antigen (PSMA) binding protein, comprising complementarity determining regions CDR1, CDR2, and CDR3, wherein (a) the amino acid sequence of CDR1 is as set forth in RFMIS$X_1$YX$_2$MH (SEQ ID No. 1); (b) the amino acid sequence of CDR2 is as set forth in $X_3$INPAX$_4$X$_5$TDYAEX$_6$VKG (SEQ ID No. 2); and (c) the amino acid sequence of CDR3 is as set forth in DX$_7$YGY (SEQ ID No. 3). In some embodiments, the prostate specific membrane antigen binding protein comprises the following formula f1-r1-f2-r2-f3-r3-f4, wherein, r1 is SEQ ID NO. 1; r2 is SEQ ID NO. 2; and r3 is SEQ ID No. 3; and wherein $f_1$, $f_2$, $f_3$ and $f_4$ are framework residues selected so that said protein is at least eighty percent identical to the amino acid sequence set forth in SEQ ID No. 4. In some embodiments, $X_1$ is proline. In some embodiments, $X_2$ is histidine. In some embodiments, $X_3$ is aspartic acid. In some embodiments, $X_4$ is lysine. In some embodiments, $X_5$ is glutamine. In some embodiments, $X_6$ is tyrosine. In some embodiments, $X_7$ is serine. In some embodiments, the prostate specific membrane antigen binding protein has a higher affinity towards a human prostate specific membrane antigen than that of a binding protein which has the sequence set forth as SEQ ID NO. 4. In some embodiments, $X_1$ is proline. In some embodiments, $X_5$ is glutamine. In some embodiments, $X_6$ is tyrosine. In some embodiments, $X_4$ is lysine, and $X_7$ is serine. In some embodiments, $X_2$ is histidine, $X_3$ is aspartic acid, $X_4$ is lysine, and $X_7$ is serine. In some embodiments, $X_1$ is proline, $X_2$ is histidine, $X_3$ is aspartic acid, and $X_7$ is serine. In some embodiments, $X_2$ is histidine, $X_3$ is aspartic acid, $X_5$ is glutamine, and $X_7$ is serine. In some embodiments, $X_2$ is histidine, $X_3$ is aspartic acid, $X_6$ is tyrosine, and $X_7$ is serine. In some embodiments, $X_2$ is histidine, and $X_7$ is serine. In some embodiments, $X_2$ is histidine, $X_3$ is aspartic acid, and $X_7$ is serine. In some embodiments, the prostate specific membrane antigen binding protein has a higher affinity towards a human prostate specific membrane antigen than that of a binding protein which has the sequence set forth in SEQ ID NO. 4. In some embodiments, the prostate specific membrane antigen binding protein further has a higher affinity towards a cynomolgus prostate specific membrane antigen than that of a binding protein which has the sequence set forth in SEQ ID NO. 4. In some embodiments, r1 comprises SEQ ID No. 5, SEQ ID No. 6, or SEQ ID No. 7. In some embodiments, r2 comprises SEQ ID No. 8, SEQ ID NO. 9, SEQ ID No. 10, SEQ ID No. 11, SEQ ID No. 12, SEQ ID No. 13, or SEQ ID No. 14. In some embodiments, r3 comprises SEQ ID No. 15.

Another embodiment of the invention provides a prostate specific membrane antigen binding protein comprising CDR1, CDR2, and CDR3, comprising the sequence set forth as SEQ ID No. 4 wherein one or more amino acid residues selected from amino acid positions 31, 33, 50, 55, 56, 62, and 97 are substituted. In some embodiments, the binding protein comprises one or more additional substitutions at amino acid positions other than positions 31, 33, 50, 55, 56, 62, and 97. In some embodiments, the binding protein comprises substitution at position 31. In some embodiments, the binding protein comprises substitution at position 33. In some embodiments, the binding protein comprises substitution at position 50. In some embodiments, the binding protein comprises substitution at position 55. In some embodiments, the binding protein comprises substitution at position 56. In some embodiments, the binding protein comprises substitution at position 62. In some embodiments, the binding protein comprises substitution at position 97. In some embodiments, the binding protein comprises substitutions at amino acid positions 55 and 97. In some embodiments, the prostate specific membrane antigen binding protein has a higher affinity towards human prostate specific membrane antigen than that of a binding protein which has the sequence set forth in SEQ ID No. 4. In some embodiments, the binding protein comprises substitutions at amino acid positions 33 and 97. In some embodiments, the binding protein comprises substitutions at amino acid positions 33, 50, and 97. In some embodiments, the prostate specific membrane antigen binding protein has a higher affinity towards human prostate specific membrane antigen than that of a binding protein which has the sequence set forth as SEQ ID No. 4. In some embodiments, the prostate specific membrane antigen binding protein has a higher affinity towards cynomolgus prostate specific membrane antigen than that of a binding protein which has the sequence set forth in SEQ ID No. 4. In some embodiments, the binding protein comprises substitutions at amino acid positions 31, 33, 50, and 97. In some embodiments, the binding protein comprises substitutions at amino acid positions 33, 50, 55, and 97. In some embodiments, the binding protein comprises substitutions in amino acid positions 33, 50, 56, and 97. In some embodiments, comprises substitutions at amino acid positions 33, 50, 62, and 97.

A further embodiment provides a prostate specific membrane antigen binding protein comprising a CDR1, CDR2 and CDR3, wherein CDR1 comprises the sequence as set forth is SEQ ID No. 16. One embodiment provides a prostate specific membrane antigen binding protein comprising a CDR1, CDR2 and CDR3, wherein CDR2 comprises the sequence as set forth in SEQ ID No. 17. An additional embodiment provides a prostate specific membrane antigen binding protein comprising a CDR1, CDR2 and CDR3, wherein CDR3 comprises the sequence as set forth in SEQ ID No. 18. In one embodiment is provided a prostate specific membrane antigen binding protein comprising a sequence that is at least 80% identical to the sequence set forth in SEQ ID No. 4. In one embodiment is provided a prostate specific membrane antigen binding protein comprising a CDR1, CDR2 and CDR3, wherein CDR1 has at least 80% identity to SEQ ID No. 16, CDR2 has at least 85% identity to SEQ ID No. 17, and CDR3 has at least 80% identity to SEQ ID No. 18.

Another embodiment provides a prostate specific membrane antigen binding protein comprising a CDR1, CDR2 and CDR3, wherein CDR1 comprises the sequence set forth in SEQ ID No. 16, CDR2 comprises the sequence set forth in SEQ ID No. 17, and CDR3 comprises the sequence set forth in SEQ ID No. 18. In some embodiments, the prostate specific membrane antigen binding protein binds to one or both of human prostate specific membrane antigen and cynomolgus prostate specific membrane antigen. In some embodiments, the binding protein binds to human prostate specific membrane antigen and cynomolgus prostate specific membrane antigen with comparable binding affinities. In some embodiments, the binding protein binds to human prostate specific membrane antigen with a higher binding affinity than cynomolgus prostate specific membrane antigen.

Another embodiment provides a polynucleotide encoding a PSMA binding protein according to the present disclosure. A further embodiment provides a vector comprising the polynucleotide encoding a PSMA binding protein according to the present disclosure. In another embodiment is provided a host cell is transformed with the vector. In another embodiment is provided a pharmaceutical composition comprising (i) a PSMA binding protein according to the present disclosure, the polynucleotide according to the present disclosure, the vector according to the present disclosure or the host cell according to the present disclosure, and (ii) a pharmaceutically acceptable carrier. Another embodiment provides a process for the production of a PSMA binding protein according to the present disclosure, said process comprising culturing a host transformed or transfected with a vector comprising a nucleic acid sequence encoding a PSMA albumin binding protein according to the present disclosure under conditions allowing the expression of the PSMA binding protein and recovering and purifying the produced protein from the culture. In one embodiment is provided a method for the treatment or amelioration of a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease comprising the administration of the PSMA binding protein according to the present disclosure, to a subject in need thereof. In some embodiments, the subject is human. In some embodiments, the method further comprises administration of an agent in combination with the PSMA binding protein according to the present disclosure.

One embodiment provides a multispecific binding protein comprising the PSMA binding protein according to the present disclosure. A further embodiment provides an antibody comprising the PSMA binding protein according to the present disclosure. In one embodiment is provided a multispecific antibody, a bispecific antibody, an sdAb, a variable heavy domain, a peptide, or a ligand, comprising the PSMA binding protein according to the present disclosure. In one embodiment is provided an antibody comprising the PSMA binding protein according to the present disclosure, wherein said antibody is a single domain antibody. In some embodiments, the single domain antibody is derived from a heavy chain variable region of IgG. A further embodiment provides a multispecific binding protein or antibody comprising the PSMA binding protein according to the present disclosure. In one embodiment is provided a method for the treatment or amelioration of a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease comprising administration of the multispecific antibody according to the present disclosure, to a subject in need thereof. In a further embodiment is provided a method for the treatment or amelioration of a prostate condition comprising administration of the multispecific antibody according to the present disclosure, to a subject in need thereof. Another embodiment provides a method for the treatment or amelioration of a prostate condition comprising administration of the PSMA binding protein according to any of the above embodiments, to a subject in need thereof. A further embodiment provides a method for the treatment or amelioration of a prostate condition comprising administration of the PSMA binding protein according to the present disclosure, to a subject in need thereof.

In some embodiments, the prostate specific membrane antigen binding protein comprises any combination of the following: (i) wherein $X_1$ is proline; (ii) wherein X2 is histidine; (iii) wherein X3 is aspartic acid; (iv) wherein X4 is lysine; (v) wherein X5 is glutamine; (vi) wherein X6 is tyrosine; and (vii) wherein X7 is serine. In some embodiments, the prostate specific membrane antigen binding protein of the above embodiment has a higher affinity towards a human prostate specific membrane antigen than that of a binding protein which has the sequence set forth as SEQ ID NO. 4. In some embodiments, the prostate specific membrane antigen binding comprises any combination of the following: (i) wherein $X_1$ is proline; wherein $X_5$ is glutamine; (ii) wherein $X_6$ is tyrosine; wherein $X_4$ is lysine and $X_7$ is serine; (iii) wherein $X_2$ is histidine, $X_3$ is aspartic acid, $X_4$ is lysine, and $X_7$ is serine; (iv) wherein $X_1$ is proline, $X_2$ is histidine, $X_3$ is aspartic acid, and $X_7$ is serine; (v) wherein $X_2$ is histidine, $X_3$ is aspartic acid, $X_5$ is glutamine, and $X_7$ is serine; (vi) wherein $X_2$ is histidine, $X_3$ is aspartic acid, $X_4$ is lysine, and $X_7$ is serine; (vii) wherein $X_1$ is proline, $X_2$ is histidine, $X_3$ is aspartic acid, and $X_7$ is serine; (viii) wherein $X_2$ is histidine, $X_3$ is aspartic acid, $X_5$ is glutamine, and $X_7$ is serine; (ix) wherein $X_2$ is histidine, $X_3$ is aspartic acid, $X_6$ is tyrosine, and $X_7$ is serine; and (x) wherein $X_2$ is histidine, $X_3$ is aspartic acid, and $X_7$ is serine. In some cases, the prostate specific membrane antigen binding protein of the above embodiment has a higher affinity towards a human prostate specific membrane antigen than that of a binding protein which has the sequence set forth in SEQ ID NO. 4. In some cases, the prostate specific membrane antigen binding protein of the above embodiment further has a higher affinity towards a cynomolgus prostate specific membrane antigen than that of a binding protein which has the sequence set forth in SEQ ID NO. 4. In some embodiments, the prostate specific membrane antigen binding protein comprises any combination of the following: (i) substitution at position 31; (ii) substitution at position 50; (iii) substitution at position 55; substitution at position 56; (iv) substitution at position 62; (v) substitution at position 97; (vi) substitutions at positions 55 and 97; (vii) substitutions at positions 33 and 97; (viii) substitutions at 33, 50, and 97; (ix)

substitutions at positions 31, 33, 50, and 97; (x) substitutions at positions 33, 50, 55, and 97; (xi) substitutions at positions 33, 50, 56, and 97; and (xiii) substitutions at positions 33, 50, 62, and 97. In some cases, the prostate specific membrane antigen binding protein of the above embodiment has a higher affinity towards human prostate specific membrane antigen than that of a binding protein which has the sequence set forth in SEQ ID No. 4. In some cases, the prostate specific membrane antigen binding protein of the above embodiment further has a higher affinity towards cynomolgus prostate specific membrane antigen than that of a binding protein which has the sequence set forth in SEQ ID No. 4.

One embodiment provides a method for the treatment or amelioration of prostate cancer, the method comprising administration of the PSMA binding protein comprising complementarity determining regions CDR1, CDR2, and CDR3, wherein (a) the amino acid sequence of CDR1 is as set forth in RFMISX$_1$YX$_2$MH (SEQ ID No. 1); (b) the amino acid sequence of CDR2 is as set forth in X$_3$INPAX$_4$X$_5$TDYAEX$_6$VKG (SEQ ID No. 2); and (c) the amino acid sequence of CDR3 is as set forth in DX$_7$YGY (SEQ ID No. 3), to a subject in need thereof.

In some embodiments the PSMA binding protein is a single domain antibody. In some embodiments, said single domain antibody is part of a trispecific antibody.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows killing by different PMSA targeting TRITAC™ molecules in prostate cancer model LNCaP. FIG. 2B shows killing by different PMSA targeting TRITAC™ molecules in prostate cancer model 22Rv1. FIG. 2C shows EC50 values for PSMA targeting TRITAC™ in LNCaP and 22Rv1 prostate cancer models.

FIGS. 5A-C show the ability of PSMA targeting TRITAC™ molecules with different affinities for PSMA to induce T cells to kill the human prostate cancer cell line LNCaP. FIG. 5A shows the experiment performed in the absence of human serum albumin with a PSMA targeting BiTE as positive control. FIG. 5B shows the experiment performed in the presence of human serum albumin with a PSMA targeting BiTE as positive control. FIG. 5C shows EC50 values for PMSA targeting TRITAC™ in the presence or absence of HSA with a PSMA targeting BiTE as a positive control in LNCaP prostate cancer models.

FIG. 7A shows EGFR and PSMA expression in LNCaP, KMS12BM, and OVCAR8 cell lines. FIG. 7B shows killing of LNCaP tumor cells by PSMA, EGFR, and negative control TRITAC™ molecules. FIG. 7C shows killing of KMS12BM tumor cells by PSMA, EGFR, and negative control TRITAC™ molecules. FIG. 7D shows killing of OVCAR8 cells by PSMA, EGFR, and negative control TRITAC™ molecules.

FIG. 8A shows PSMA TRITAC™ C235 activity after pre-incubation at 37° C. or freeze/thaw cycles. FIG. 8B shows PSMA TRITAC™ C359 activity after pre-incubation at 37° C. or freeze/thaw cycles. FIG. 8C shows PSMA TRITAC™ C360 activity after pre-incubation at 37° C. or freeze/thaw cycles. FIG. 8D shows PSMA TRITAC™ C361 activity after pre-incubation at 37° C. or freeze/thaw cycles.

FIG. 9A shows the impact of the PSMA targeting TRITAC™ molecule in redirecting cynomolgus peripheral blood mononuclear cells (PBMCs), from cynomolgus monkey donor G322, in killing LNCaP cells. FIG. 9B shows the impact of the PSMA targeting TRITAC™ molecule in redirecting cynomolgus PBMCs, from cynomolgus monkey donor D173, to kill MDAPCa2b cells.

DETAILED DESCRIPTION OF THE INVENTION

Figure 1:
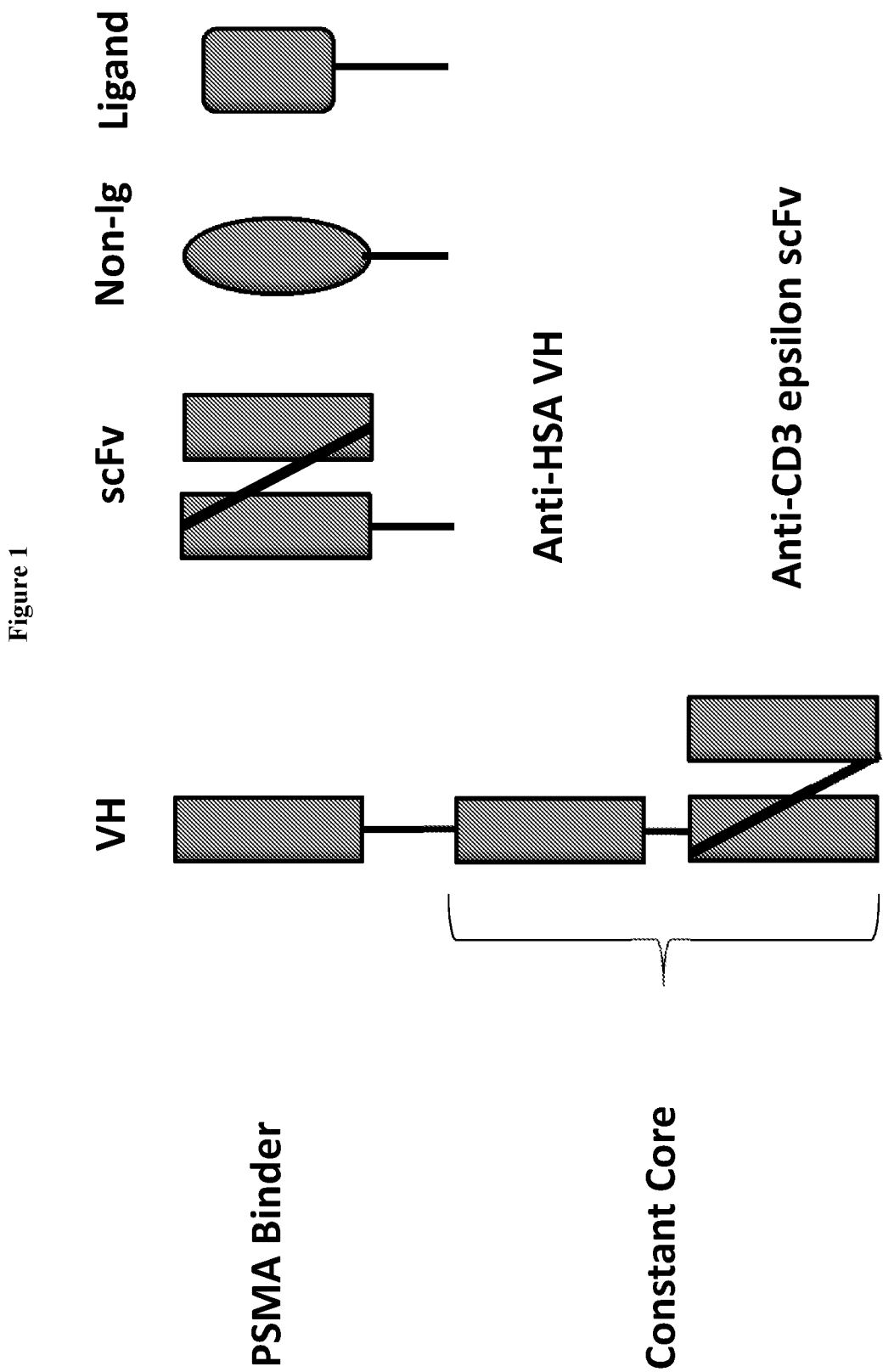
FIG. 1 is schematic representation of an exemplary PSMA targeting trispecific antigen-binding protein where the protein has an constant core element comprising an anti-CD3ε single chain variable fragment (scFv) and an anti-HSA variable heavy chain region; and a PSMA binding domain that can be a VH, scFv, a non-Ig binder, or ligand.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby Certain Definitions The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The term "Framework" or "FR" residues (or regions) refer to variable domain residues other than the CDR or hypervariable region residues as herein defined. A "human consensus framework" is a framework which represents the most commonly occurring amino acid residue in a selection of human immunoglobulin VL or VH framework sequences.

As used herein, "Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the βsheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. "Variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. It is not intended that CDRs of the present disclosure necessarily correspond to the Kabat numbering convention.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer softwares such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

As used herein, "elimination half-time" is used in its ordinary sense, as is described in *Goodman and Gillman's The Pharmaceutical Basis of Therapeutics* 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, $t_{1/2}$ the time required for 50% completion of the process. The units of these two constants are $time^{-1}$ and time, respectively. A first-order rate constant and the half-time of the reaction are simply related ($k \times t_{1/2} = 0.693$) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

As used herein, the term "binding affinity" refers to the affinity of the proteins described in the disclosure to their binding targets, and is expressed numerically using "Kd" values. If two or more proteins are indicated to have comparable binding affinities towards their binding targets, then the Kd values for binding of the respective proteins towards their binding targets, are within ±2-fold of each other. If two or more proteins are indicated to have comparable binding affinities towards single binding target, then the Kd values for binding of the respective proteins towards said single binding target, are within ±2-fold of each other. If a protein is indicated to bind two or more targets with comparable binding affinities, then the Kd values for binding of said protein to the two or more targets are within ±2-fold of each other. In general, a higher Kd value corresponds to a weaker binding. In some embodiments, the "Kd" is measured by a radiolabeled antigen binding assay (MA) or surface plasmon resonance assays using a BIAcore™-2000 or a BIAcore™-3000 (BIAcore, Inc., Piscataway, N.J.). In certain embodiments, an "on-rate" or "rate of association" or "association rate" or "kon" and an "off-rate" or "rate of dissociation" or "dissociation rate" or "koff" are also determined with the surface plasmon resonance technique using a BIAcore™-2000 or a BIAcore™-3000 (BIAcore, Inc., Piscataway, N.J.). In additional embodiments, the "Kd", "kon", and "koff" are measured using the OCTET® Systems (Pall Life Sciences). In an exemplary method for measuring binding affinity using the OCTET® Systems, the ligand, e.g., biotinylated human or cynomolgus PSMA, is immobilized on the OCTET® streptavidin capillary sensor tip surface which streptavidin tips are then activated according to manufacturer's instructions using about 20-50 µg/ml human or cynomolgus PSMA protein. A solution of PBS/Casein is also introduced as a blocking agent. For association kinetic measurements, PSMA binding protein variants are introduced at a concentration ranging from about 10 µg/ml to about 1000 µg/ml. Complete dissociation is observed in case of the negative control, assay buffer without the binding proteins. The kinetic parameters of the binding reactions are then determined using an appropriate tool, e.g., ForteBio software.

Described herein are PSMA binding proteins, pharmaceutical compositions as well as nucleic acids, recombinant expression vectors, and host cells for making such PSMA binding proteins. Also provided are methods of using the disclosed PSMA binding proteins in the prevention, and/or treatment of diseases, conditions and disorders. The PSMA binding proteins are capable specifically binding to PSMA. In some embodiments, the PSMA binding proteins include additional domains, such as a CD3 binding domain.

Prostate Specific Membrane Antigen (PSMA) and its Role in Prostate Conditions

Contemplated herein are prostate specific membrane antigen binding proteins. Prostate-specific membrane antigen (PSMA), also known as glutamate carboxypeptidase II, N-acetyl-α-linked acidic dipeptidase I [Naaladase (NLD) I], or folate hydrolase, is a 750-residue type II transmembrane glycoprotein that has been found to be highly expressed in prostate cancer cells and in nonprostatic solid tumor neovasculature and expressed at lower levels in other tissues including healthy prostate, kidney, liver, small intestine, small bowel, salivary gland, duodenal mucosa, proximal renal tubules, and brain. PSMA is a member of a superfamily of zinc-dependent exopeptidases, which include carboxypeptidases with a mononuclear zinc active site (e.g., carboxypeptidase A) and carboxy- and aminopeptidases with a binuclear zinc active site [e.g., carboxypeptidase G2 (CPG2), peptidases T and V (PepT and PepV), *Streptomyces griseus* aminopeptidase (Sgap), and *Aeromonas proteolytica* aminopeptidase (AAP)]. In addition to a limited region of homology with these soluble single-domain (e.g., AAP), or double-domain (e.g., CPG2) zinc-dependent exopeptidases, the entire sequence of PSMA is homologous to at least four other human proteins: NLDL (expressed in ileum; 35% identity), NLD2 (expressed in ovary, testis, and brain; 67% identity), transferrin receptor (TfR) 1 (TfR1; expressed in most cell types; 26% identity), and TfR2 (expressed predominantly in liver; 28% identity).

The crystal structure of PSMA has been shown to comprise a symmetric dimer with each polypeptide chain containing three domains analogous to the three TfR1 domains: a protease domain, an apical domain, and a helical domain. A large cavity (≈1,100 Å2) at the interface between the three domains includes a binuclear zinc site and predominantly polar residues (66% of 70 residues). The observation of two zinc ions and conservation of many of the cavity-forming residues among PSMA orthologs and homologs identify the cavity as the probable substrate-binding site.

Typically, PSMA expression is found to increase with prostate disease progression and metastasis. The expression of PSMA is increased in prostate cancer, especially in poorly differentiated, metastatic, and hormone refractory carcinomas. PSMA is also expressed in endothelial cells of capillary vessels in peritumoral and endotumoral areas of certain malignancies, including renal cell carcinomas, and colon carcinomas, but not in blood vessels from normal tissues. In addition, PSMA is reported to be related to tumor angiogenesis. PSMA has been demonstrated to be expressed in endothelial cells of tumor-associated neovasculature in carcinomas of the colon, breast, bladder, pancreas, kidney, and melanoma.

In addition to its role as a tumor marker, PSMA contains a binuclear zinc site and is active as a glutamate carboxypeptidase, catalyzing the hydrolytic cleavage of α- or γ-linked glutamates from peptides or small molecules. Its substrates include poly-γ-glutamated folates, which are essential nutrients, and the poly-γ-glutamated form of the anticancer drug methotrexate, in which case cleavage renders it less efficacious. The enzymatic activity of PSMA can be exploited for the design of prodrugs, in which an inactive glutamated form of the drug is selectively cleaved and thereby activated only at cells that express PSMA. PSMA also cleaves and inactivates the abundant neuropeptide N-acetyl-1-aspartyl-1-glutamate (α-NAAG), which is an inhibitor of the NMDA ionotropic receptor and an agonist of the type II metabotropic glutamate receptor subtype 3. A breakdown of the regulation of glutamatergic neurotransmission by α-NAAG is implicated in schizophrenia, seizure disorders, Alzheimer's disease, Huntington's disease, and amyotrophic lateral sclerosis. Thus, inhibition of PSMA potentially confers neuroprotection both by reducing glutamate and increasing α-NAAG. For example, the subnanomolar inhibitor 2-(phosphonomethyl) pentanedioc acid has been shown to provide neuroprotection in cell culture and/or animal models of ischemia, diabetic neuropathy, drug abuse, chronic pain, and amyotrophic lateral sclerosis.

Prostate cancer is the most prevalent type of cancer and one of the leading causes of death from cancer in American men. The number of men diagnosed with prostate cancer has steadily increasing as a result of the increasing population of older men as well as a greater awareness of the disease leading to its earlier diagnosis. The life time risk for men developing prostate cancer is about 1 in 5 for Caucasians, 1 in 6 for African Americans. High risk groups are represented by those with a positive family history of prostate cancer or African Americans. Over a lifetime, more than two-thirds of the men diagnosed with prostate cancer die of the disease. Moreover, many patients who do not succumb to prostate cancer require continuous treatment to ameliorate symptoms such as pain, bleeding and urinary obstruction. Thus, prostate cancer also represents a major cause of suffering and increased health care expenditures. Where prostate cancer is localized and the patient's life expectancy is 10 years or more, radical prostatectomy offers the best chance for eradication of the disease. Historically, the drawback of this procedure is that most cancers had spread beyond the bounds of the operation by the time they were detected. Patients with bulky, high-grade tumors are less likely to be successfully treated by radical prostatectomy. Radiation therapy has also been widely used as an alternative to radical prostatectomy. Patients generally treated by radiation therapy are those who are older and less healthy and those with higher-grade, more clinically advanced tumors. Particularly preferred procedures are external-beam therapy which involves three dimensional, confocal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy. For treatment of patients with locally advanced disease, hormonal therapy before or following radical prostatectomy or radiation therapy has been utilized. Hormonal therapy is the main form of treating men with disseminated prostate cancer. Orchiectomy reduces serum testosterone concentrations, while estrogen treatment is similarly beneficial. Diethylstilbestrol from estrogen is another useful hormonal therapy which has a disadvantage of causing cardiovascular toxicity. When gonadotropin-releasing hormone agonists are administered testosterone concentrations are ultimately reduced. Flutamide and other nonsteroidal, anti-androgen agents block binding of testosterone to its intracellular receptors. As a result, it blocks the effect of testosterone, increasing serum testosterone concentrations and allows patients to remain potent—a significant problem after radical prostatectomy and radiation treatments. Cytotoxic chemotherapy is largely ineffective in treating prostate cancer. Its toxicity makes such therapy unsuitable for elderly patients. In addition, prostate cancer is relatively resistant to cytotoxic agents. Relapsed or more advanced disease is also treated with anti-androgen therapy. Unfortunately, almost all tumors become hormone-resistant and progress rapidly in the absence of any effective therapy. Accordingly, there is a need for effective therapeutics for prostate cancer which are not overwhelmingly toxic to normal tissues of a patient, and which are effective in selectively eliminating prostate cancer cells. The present disclosure provides, in certain embodiments, PSMA binding proteins that are useful in treating prostate cancer. In additional embodiments, the disclosure provides a method of treating prostate cancer by immunotherapy using the PSMA binding proteins described herein.

Prostate cancer is also difficult to diagnose because the prostate specific membrane antigen screening method is associated with many false positives. Accordingly, in some embodiments, the present disclosure provides an improved method of detecting prostate cancer using the PSMA binding proteins described herein.

PSMA Binding Proteins

Provided herein in certain embodiments are binding proteins, such as anti-PSMA antibodies or antibody variants, which bind to a PSMA protein. The PSMA protein, in some embodiments, is a multimer. A PSMA protein multimer, as used herein, is a protein complex of at least two PSMA proteins or fragments thereof. The PSMA protein multimers can be composed of various combinations of full-length PSMA proteins (e.g., SEQ ID No. 20), recombinant soluble PSMA (rsPSMA, e.g., amino acids 44-750 of SEQ ID No. 20) and fragments of the foregoing that form multimers (i.e., that retain the protein domain required for forming dimers and/or higher order multimers of PSMA). In some embodiments, at least one of the PSMA proteins forming the multimer is a recombinant, soluble PSMA (rsPSMA) polypeptide. In some embodiments, PSMA protein multimers are dimers, such as those formed from recombinant soluble PSMA protein. In some embodiments, rsPSMA is a homodimer. While not being bound by any particular theory, the PSMA protein multimers referred to herein are believed to assume a native conformation and preferably have such a conformation. The PSMA proteins in certain embodiments are noncovalently bound together to form the PSMA protein multimer. For example, it has been discovered that PSMA protein noncovalently associates to form dimers under non-denaturing conditions. The PSMA protein multimers can, and preferably do, retain the activities of PSMA. The activity of a PSMA protein is, in certain embodiments, an enzymatic activity, such as folate hydrolase activity, NAALADase activity, dipeptidyl peptidase IV activity and γ-glutamyl hydrolase activity. Methods for testing the PSMA activity of multimers are known in the field (e.g., reviewed by O'Keefe et al. in: Prostate Cancer: Biology, Genetics, and the New Therapeutics, L. W. K. Chung, W. B. Isaacs and J. W. Simons (eds.) Humana Press, Totowa, N.J., 2000, pp. 307-326).

In some embodiments, the binding proteins of the present disclosure that bind a PSMA protein or a PSMA protein multimer modulate enzymatic activity of the PSMA protein or the PSMA protein multimer. In some embodiments, the PSMA binding protein inhibits at least one enzymatic activity such as NAALADase activity, folate hydrolase activity, dipeptidyl dipeptidase IV activity, γ-glutamyl hydrolase activity, or combinations thereof. In other embodiments, the PSMA binding protein enhances at least one enzymatic activity such as NAALADase activity, folate hydrolase activity, dipeptidyl dipeptidase IV activity, γ-glutamyl hydrolase activity, or combinations thereof.

As used herein, the term "antibody variants" refers to variants and derivatives of an antibody described herein. In certain embodiments, amino acid sequence variants of the anti-PSMA antibodies described herein are contemplated. For example, in certain embodiments amino acid sequence variants of anti-PSMA antibodies described herein are contemplated to improve the binding affinity and/or other biological properties of the antibodies. Exemplary method for preparing amino acid variants include, but are not limited to, introducing appropriate modifications into the nucleotide sequence encoding the antibody, or by peptide synthesis. Such modifications include, for example, deletions from, and/or insertions into and/or substitutions of residues within the amino acid sequences of the antibody.

Any combination of deletion, insertion, and substitution can be made to arrive at the final construct, provided that the final construct possesses the desired characteristics, e.g., antigen-binding. In certain embodiments, antibody variants having one or more amino acid substitutions are provided. Sites of interest for substitution mutagenesis include the CDRs and framework regions. Examples of such substitutions are described below. Amino acid substitutions may be introduced into an antibody of interest and the products screened for a desired activity, e.g., retained/improved antigen binding, decreased immunogenicity, or improved antibody-dependent cell mediated cytotoxicity (ADCC) or complement dependent cytotoxicity (CDC). Both conservative and non-conservative amino acid substitutions are contemplated for preparing the antibody variants.

In another example of a substitution to create a variant anti-PSMA antibody, one or more hypervariable region residues of a parent antibody are substituted. In general, variants are then selected based on improvements in desired properties compared to a parent antibody, for example, increased affinity, reduced affinity, reduced immunogenicity, increased pH dependence of binding. For example, an affinity matured variant antibody can be generated, e.g., using phage display-based affinity maturation techniques such as those described herein and known in the field.

Substitutions can be made in hypervariable regions (HVR) of a parent anti-PSMA antibody to generate variants and variants are then selected based on binding affinity, i.e., by affinity maturation. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. Substitutions can be in one, two, three, four, or more sites within a parent antibody sequence.

In some embodiments, the PSMA binding protein described herein is a single domain antibody such as a heavy chain variable domain (VH), a variable domain (VHH) of camelid derived sdAb, peptide, ligand or small molecule entity specific for PSMA. In some embodiments, the PSMA binding domain of the PSMA binding protein described herein is any domain that binds to PSMA including but not limited to domains from a monoclonal antibody, a polyclonal antibody, a recombinant antibody, a human antibody, a humanized antibody. In certain embodiments, the PSMA binding protein is a single-domain antibody. In other embodiments, the PSMA binding protein is a peptide. In further embodiments, the PSMA binding protein is a small molecule.

Generally, it should be noted that the term single domain antibody as used herein in its broadest sense is not limited to a specific biological source or to a specific method of preparation. For example, in some embodiments, the single domain antibodies of the disclosure are obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a species of mammal, such as from a human being, or by expression of a nucleic acid encoding such a camelized VH domain; (5) by "camelisation" of a "domain antibody" or "Dab", or by expression of a nucleic acid encoding such a camelized VH domain; (6) by using synthetic or semi-synthetic techniques for preparing proteins, polypeptides or other amino acid sequences; (7) by preparing a nucleic acid encoding a single domain antibody using techniques for nucleic acid synthesis known in the field, followed by expression of the nucleic acid thus obtained; and/or (8) by any combination of one or more of the foregoing.

In one embodiment, a single domain antibody corresponds to the VHH domains of naturally occurring heavy chain antibodies directed against PSMA. As further described herein, such VHH sequences can generally be generated or obtained by suitably immunizing a species of Camelid with PSMA, (i.e., so as to raise an immune response and/or heavy chain antibodies directed against PSMA), by obtaining a suitable biological sample from said Camelid (such as a blood sample, serum sample or sample of B-cells), and by generating VHH sequences directed against PSMA, starting from said sample, using any suitable technique known in the field.

In another embodiment, such naturally occurring VHH domains against PSMA, are obtained from naïve libraries of Camelid VHH sequences, for example by screening such a library using PSMA, or at least one part, fragment, antigenic determinant or epitope thereof using one or more screening techniques known in the field. Such libraries and techniques are for example described in WO 99/37681, WO 01/90190, WO 03/025020 and WO 03/035694. Alternatively, improved synthetic or semi-synthetic libraries derived from naïve VHH libraries are used, such as VHH libraries obtained from naïve VHH libraries by techniques such as random mutagenesis and/or CDR shuffling, as for example described in WO 00/43507.

In a further embodiment, yet another technique for obtaining VHH sequences directed against PSMA, involves suitably immunizing a transgenic mammal that is capable of expressing heavy chain antibodies (i.e., so as to raise an immune response and/or heavy chain antibodies directed against PSMA), obtaining a suitable biological sample from said transgenic mammal (such as a blood sample, serum sample or sample of B-cells), and then generating VHH sequences directed against PSMA, starting from said sample, using any suitable technique known in the field. For example, for this purpose, the heavy chain antibody-expressing rats or mice and the further methods and techniques described in WO 02/085945 and in WO 04/049794 can be used.

In some embodiments, a single domain PSMA antibody, as described herein comprises single domain antibody with an amino acid sequence that corresponds to the amino acid sequence of a naturally occurring VHH domain, but that has been "humanized", i.e., by replacing one or more amino acid residues in the amino acid sequence of said naturally occurring VHH sequence (and in particular in the framework sequences) by one or more of the amino acid residues that occur at the corresponding position(s) in a VH domain from a conventional 4-chain antibody from a human being (e.g., as indicated above). This can be performed in a manner known in the field, which will be clear to the skilled person, for example on the basis of the further description herein. Again, it should be noted that such humanized anti-PSMA single domain antibodies of the disclosure are obtained in any suitable manner known per se (i.e., as indicated under points (1)-(8) above) and thus are not strictly limited to polypeptides that have been obtained using a polypeptide that comprises a naturally occurring VHH domain as a starting material. In some additional embodiments, a single domain PSMA antibody, as described herein, comprises a single domain antibody with an amino acid sequence that corresponds to the amino acid sequence of a naturally occurring VH domain, but that has been "camelized", i.e., by replacing one or more amino acid residues in the amino acid sequence of a naturally occurring VH domain from a conventional 4-chain antibody by one or more of the amino acid residues that occur at the corresponding position(s) in a VHH domain of a heavy chain antibody. Such "camelizing" substitutions are preferably inserted at amino acid positions that form and/or are present at the VH-VL interface, and/or at the so-called Camelidae hallmark residues (see for example WO 94/04678 and Davies and Riechmann (1994 and 1996)). Preferably, the VH sequence that is used as a starting material or starting point for generating or designing the camelized single domain is preferably a VH sequence from a mammal, more preferably the VH sequence of a human being, such as a VH3 sequence. However, it should be noted that such camelized anti-PSMA single domain antibodies of the disclosure, in certain embodiments, is obtained in any suitable manner known in the field (i.e., as indicated under points (1)-(8) above) and thus are not strictly limited to polypeptides that have been obtained using a polypeptide that comprises a naturally occurring VH domain as a starting material. For example, as further described herein, both "humanization" and "camelization" is performed by providing a nucleotide sequence that encodes a naturally occurring VHH domain or VH domain, respectively, and then changing, one or more codons in said nucleotide sequence in such a way that the new nucleotide sequence encodes a "humanized" or "camelized" single domain antibody, respectively. This nucleic acid can then be expressed, so as to provide the desired anti-PSMA single domain antibody of the disclosure. Alternatively, in other embodiments, based on the amino acid sequence of a naturally occurring VHH domain or VH domain, respectively, the amino acid sequence of the desired humanized or camelized anti-PSMA single domain antibody of the disclosure, respectively, are designed and then synthesized de novo using known techniques for peptide synthesis. In some embodiments, based on the amino acid sequence or nucleotide sequence of a naturally occurring VHH domain or VH domain, respectively, a nucleotide sequence encoding the desired humanized or camelized anti-PSMA single domain antibody of the disclosure, respectively, is designed and then synthesized de novo using known techniques for nucleic acid synthesis, after which the nucleic acid thus obtained is expressed in using known expression techniques, so as to provide the desired anti-PSMA single domain antibody of the disclosure.

Other suitable methods and techniques for obtaining the anti-PSMA single domain antibody of the disclosure and/or nucleic acids encoding the same, starting from naturally occurring VH sequences or VHH sequences for example comprises combining one or more parts of one or more naturally occurring VH sequences (such as one or more framework (FR) sequences and/or complementarity determining region (CDR) sequences), one or more parts of one or more naturally occurring VHH sequences (such as one or more FR sequences or CDR sequences), and/or one or more synthetic or semi-synthetic sequences, in a suitable manner, so as to provide an anti-PSMA single domain antibody of the disclosure or a nucleotide sequence or nucleic acid encoding the same.

It is contemplated that in some embodiments the PSMA binding protein is fairly small and no more than 25 kD, no more than 20 kD, no more than 15 kD, or no more than 10 kD in some embodiments. In certain instances, the PSMA binding protein is 5 kD or less if it is a peptide or small molecule entity.

In some embodiments, the PSMA binding protein is an anti-PSMA specific antibody comprising a heavy chain variable complementarity determining regions (CDR), CDR1, a heavy chain variable CDR2, a heavy chain variable CDR3, a light chain variable CDR1, a light chain variable CDR2, and a light chain variable CDR3. In some embodiments, the PSMA binding protein comprises any domain that binds to PSMA including but not limited to domains from a monoclonal antibody, a polyclonal antibody, a recombinant antibody, a human antibody, a humanized antibody, or antigen binding fragments such as single domain antibodies (sdAb), Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some instances, it is beneficial for the PSMA binding domain to be derived from the same species in which the PSMA binding protein described herein will ultimately be used in. For example, for use in humans, it may be beneficial for the PSMA binding domain of the PSMA binding protein to comprise human or humanized residues from the antigen binding domain of an antibody or antibody fragment. In some embodiments, the PSMA binding protein is an anti-PSMA specific binding protein comprising a heavy chain variable CDR1, a heavy chain variable CDR2, and a heavy chain variable CDR3. In some embodiments, the PSMA binding protein is an anti-PSMA single domain antibody comprising a heavy chain variable CDR1, a heavy chain variable CDR2, and a heavy chain variable CDR3.

In some embodiments, the PSMA binding protein of the present disclosure is a polypeptide comprising an amino acid sequence that is comprised of four framework regions/sequences (f1-f4) interrupted by three complementarity determining regions/sequences, as represented by the formula: f1-r1-f2-r2-f3-r3-f4, wherein r1, r2, and r3 are complementarity determining regions CDR1, CDR2, and CDR3, respectively, and f1, f2, f3, and f4 are framework residues. The framework residues of the PSMA binding protein of the present disclosure comprise, for example, 75, 76, 77, 78, 79, 80, 81 amino acid residues, and the complementarity determining regions comprise, for example, 30, 31, 32, 33, 34, 35, 36 amino acid residues. In some embodiments, the PSMA binding protein comprises an amino acid sequence as set forth in SEQ ID No. 4 comprising framework residues and CDR1, a CDR2, and a CDR3, wherein (a) the CDR1 comprises the amino acid sequence as set forth in SEQ ID No. 16 or a variant having one, two, three, or four amino acid substitutions in SEQ ID No. 16, (b) the CDR2 comprises a sequence as set forth in SEQ ID No. 17 or a variant having one, two, three, or four amino acid substitutions in SEQ ID No. 17, and (c) the CDR3 comprises a sequence as set forth in SEQ ID No. 18 or a variant having one, two, three, or four amino acid substitutions in SEQ ID No. 18.

In some embodiments, the PSMA binding protein comprises an amino acid sequence as set forth in SEQ ID No. 19 comprising framework residues and CDR1, a CDR2, and a CDR3, wherein (a) the CDR1 comprises the amino acid sequence as set forth in SEQ ID No. 16 or a variant having one, two, three, or four amino acid substitutions in SEQ ID No. 16, (b) the CDR2 comprises a sequence as set forth in SEQ ID No. 17 or a variant having one, two, three, or four amino acid substitutions in SEQ ID No. 17, and (c) the CDR3 comprises a sequence as set forth in SEQ ID No. 18 or a variant having one, two, three, or four amino acid substitutions in SEQ ID No. 18.

In embodiments wherein the CDR1 of the PSMA binding protein comprises the amino acid sequence as set forth in SEQ ID No. 16 or a variant having one, two, three, or four amino acid substitutions in SEQ ID No. 16, such substitutions include, for example, proline, histidine. In embodiments wherein the CDR2 of the PSMA binding protein comprises the amino acid sequence as set forth in SEQ ID No. 17 or a variant having one, two, three, or four amino acid substitutions in SEQ ID No. 17, such substitutions include, for example, aspartic acid, lysine, glutamine, tyrosine.

In embodiments wherein the CDR3 of the PSMA binding protein comprises the amino acid sequence as set forth in SEQ ID No. 18 or a variant having one, two, three, or four amino acid substitutions in SEQ ID No. 18, such substitutions include, for example, serine.

In some embodiments, the PSMA binding protein of the present disclosure comprises the following formula: f1-r1-f2-r2-f3-r3-f4, wherein r1, r2, and r3 are complementarity determining regions CDR1, CDR2, and CDR3, respectively, and f1, f2, f3, and f4 are framework residues, and wherein r1 comprises SEQ ID No. 5, SEQ ID No. 6, or SEQ ID No. 7, r2 comprises SEQ ID No. 8, SEQ ID NO. 9, SEQ ID No. 10, SEQ ID No. 11, SEQ ID No. 12, SEQ ID No. 13, or SEQ ID No. 14, and r3 comprises SEQ ID No. 15. In some embodiments, the PSMA binding protein of the present disclosure is a single domain antibody comprising the following formula: f1-r1-f2-r2-f3-r3-f4, wherein r1, r2, and r3 are complementarity determining regions CDR1, CDR2, and CDR3, respectively, and f1, f2, f3, and f4 are framework residues, and wherein r1 is SEQ ID No. 5, SEQ ID No. 6, or SEQ ID No. 7, r2 is SEQ ID No. 8, SEQ ID NO. 9, SEQ ID No. 10, SEQ ID No. 11, SEQ ID No. 12, SEQ ID No. 13, or SEQ ID No. 14, and r3 is SEQ ID No. 15.

In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X$_3$INPAX4X$_5$TDYAEX6VKG), and (c) the amino acid sequence of CDR3 is as set forth in SEQ ID No. 3 (DX$_7$YGY). In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 17, and (c) the amino acid sequence of CDR3 is as set forth in SEQ ID No. 18. In some embodiments, the PSMA binding protein comprises a CDR1, CDR2, and CDR3, wherein (a) the amino acid sequence of CDR1 is as set forth in SEQ ID No. 16, (b) the amino acid sequence of CDR2 is as set forth in SEQ ID No. 2 (X$_3$INPAX$_4$X$_5$TDYAEX6VKG), and (c) the amino acid sequence of CDR3 is as set forth in SEQ ID No. 18. In some embodiments, the PSMA binding protein comprises a CDR1, CDR2, and CDR3, wherein (a) the amino acid sequence of CDR1 is as set forth in SEQ ID No. 16, (b) the amino acid sequence of CDR2 is as set forth in SEQ ID No. 17, and (c) the amino acid sequence of CDR3 is as set forth in SEQ ID No. 3 (DX$_7$YGY). In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X$_3$INPAX$_4$X$_5$TDYAEX$_6$VKG), and (c) the amino acid sequence of CDR3 is as set forth in SEQ ID No. 18. In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 17, and (c) the amino acid sequence of CDR3 is as set forth in SEQ ID No. 3 (DX$_7$YGY). In some embodiments, the PSMA binding protein comprises a CDR1, CDR2, and CDR3, wherein (a) the amino acid sequence of CDR1 is as set forth in SEQ ID No. 16, (b) the amino acid sequence of CDR2 is as set forth in SEQ ID No. 2 (X$_3$INPAX$_4$X$_5$TDYAEX$_6$VKG), and (c) the amino acid sequence of CDR3 is as set forth in SEQ ID No. 3 (DX$_7$YGY).

In some embodiments, the amino acid residues $X_1$, $X_2$, $X_3$, $X_4$, $X_5$, $X_6$, and $X_7$ are independently selected from glutamic acid, proline, serine, histidine, threonine, aspartic acid, glycine, lysine, threonine, glutamine, and tyrosine. In some embodiments, $X_1$ is proline. In some embodiments, $X_2$ is histidine. In some embodiments, $X_3$ is aspartic acid. In some embodiments, $X_4$ is lysine. In some embodiments, $X_5$ is glutamine. In some embodiments, $X_6$ is tyrosine. In some embodiments, $X_7$ is serine. The PSMA binding protein of the present disclosure may in some embodiments comprise CDR1, CDR2, and CDR3 sequences wherein $X_1$ is glutamic acid, $X_2$ is histidine, $X_3$ is aspartic acid, $X_4$ is glycine, $X_5$ is threonine, $X_6$ is serine, and $X_7$ is serine.

In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X$_3$INPAX$_4$X$_5$TDYAEX$_6$VKG), and (c) the amino acid sequence of CDR3 is as set forth in SEQ ID No. 3 (DX$_7$YGY), wherein X1 is proline. In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X$_3$INPAX$_4$X$_5$TDYAEX$_6$VKG), and (c) the amino acid sequence of CDR3 is as set forth in SEQ ID No. 3 (DX$_7$YGY), wherein X5 is glutamine. In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X$_3$INPAX$_4$X$_5$TDYAEX$_6$VKG), and (c) the amino acid sequence of CDR3 is as set forth in SEQ ID No. 3 (DX$_7$YGY), wherein $X_6$ is tyrosine. In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X$_3$INPAX$_4$X$_5$TDYAEX$_6$VKG), and (c) the amino acid sequence of CDR3 is as set forth in SEQ ID No. 3 (DX$_7$YGY), wherein $X_4$ is lysine, and $X_7$ is serine. In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X3INPAX$_4$X$_5$TDYAEX$_6$VKG), and (c) the amino acid sequence of CDR3 is as set forth in SEQ ID No. 3 (DX$_7$YGY), wherein $X_2$ is histidine, $X_3$ is aspartic acid, $X_4$ is lysine, and $X_7$ is serine. In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X$_3$INPAX$_4$X$_5$TDYAEX$_6$VKG), and (c) the amino acid sequence of CDR3 is as set forth in SEQ ID No. 3 (DX$_7$YGY), wherein $X_1$ is proline, $X_2$ is histidine, $X_3$ is aspartic acid, and $X_7$ is serine.

In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X$_3$INPAX$_4$X$_5$TDYAEX$_6$VKG), and (c) the amino acid sequence of CDR3 is as set forth in SEQ ID No. 3 (DX$_7$YGY), wherein $X_2$ is histidine, $X_3$ is aspartic acid, $X_5$ is glutamine, and $X_7$ is serine. In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X$_3$INPAX$_4$X$_5$TDYAEX$_6$VKG), and (c) the amino acid sequence of CDR3 is as set forth in SEQ ID No. 3 (DX$_7$YGY), wherein $X_2$ is histidine, $X_3$ is aspartic acid, $X_6$ is tyrosine, and $X_7$ is serine. In some embodiments, the PSMA binding protein comprises a CDR1, CDR2, and CDR3, wherein (a) the amino acid sequence of CDR1 is as set forth in SEQ ID No. 1 (RFMISX$_1$YX$_2$MH), (b) the amino acid sequence of CDR2 is as set forth in SEQ ID No. 2 (X$_3$INPAX$_4$X$_5$TDYAEX$_6$VKG), and (c) the amino acid sequence of CDR3 is as set forth in SEQ ID No. 3 (DX$_7$YGY), wherein X$_2$ is histidine, X$_3$ is aspartic acid, and X$_7$ is serine.

The PSMA binding protein of the present disclosure may in some embodiments comprise CDR1, CDR2, and CDR3 sequences wherein X$_1$ is glutamic acid, X$_2$ is histidine, X$_3$ is threonine, X$_4$ is glycine, X$_5$ is threonine, X$_6$ is serine, and X$_7$ is serine. The PSMA binding protein of the present disclosure may in some embodiments comprise CDR1, CDR2, and CDR3 sequences wherein X$_1$ is glutamic acid, X$_2$ is histidine, X$_3$ is threonine, X$_4$ is glycine, X$_5$ is threonine, X$_6$ is serine, and X$_7$ is serine. The PSMA binding protein of the present disclosure may in some embodiments comprise CDR1, CDR2, and CDR3 sequences wherein X$_1$ is glutamic acid, X$_2$ is serine, X$_3$ is threonine, X$_4$ is lysine, X$_5$ is threonine, X$_6$ is serine, and X$_7$ is serine. The PSMA binding protein of the present disclosure may in some embodiments comprise CDR1, CDR2, and CDR3 sequences wherein X$_1$ is proline, X$_2$ is serine, X$_3$ is threonine, X$_4$ is glycine, X$_5$ is threonine, X6 is serine, and X7 is glycine. The PSMA binding protein of the present disclosure may in some embodiments comprise CDR1, CDR2, and CDR3 sequences wherein X$_1$ is glutamic acid, X$_2$ is serine, X$_3$ is threonine, X$_4$ is glycine, X$_5$ is glutamine, X$_6$ is serine, and X$_7$ is glycine. The PSMA binding protein of the present disclosure may in some embodiments comprise CDR1, CDR2, and CDR3 sequences wherein X$_1$ is glutamic acid, X$_2$ is serine, X$_3$ is threonine, X$_4$ is glycine, X$_5$ is threonine, X$_6$ is tyrosine, and X$_7$ is glycine. The PSMA binding protein of the present disclosure may in some embodiments comprise CDR1, CDR2, and CDR3 sequences wherein X$_1$ is glutamic acid, X$_2$ is histidine, X$_3$ is aspartic acid, X$_4$ is lysine, X$_5$ is threonine, X$_6$ is serine, and X$_7$ is serine. The PSMA binding protein of the present disclosure may in some embodiments comprise CDR1, CDR2, and CDR3 sequences wherein X$_1$ is proline, X$_2$ is histidine, X$_3$ is aspartic acid, X$_4$ is glycine, X$_5$ is threonine, X$_6$ is serine, and X$_7$ is serine. The PSMA binding protein of the present disclosure may in some embodiments comprise CDR1, CDR2, and CDR3 sequences wherein X$_1$ is glutamic acid, X$_2$ is histidine, X$_3$ is aspartic acid, X$_4$ is glutamine, X$_5$ is threonine, X$_6$ is serine, and X$_7$ is serine. The PSMA binding protein of the present disclosure may in some embodiments comprise CDR1, CDR2, and CDR3 sequences wherein X$_1$ is glutamic acid, X$_2$ is histidine, X$_3$ is aspartic acid, X$_4$ is glycine, X$_5$ is threonine, X$_6$ is tyrosine, and X$_7$ is serine. The PSMA binding protein of the present disclosure may in some embodiments comprise CDR1, CDR2, and CDR3 sequences wherein X$_2$ is histidine, and X$_7$ is serine. Exemplary framework sequences are disclosed as SEQ ID NO: 165-168.

In some embodiments, the prostate specific membrane antigen binding protein comprises any combination of the following: (i) wherein X$_1$ is proline; (ii) wherein X2 is histidine; (iii) wherein X3 is aspartic acid; (iv) wherein X4 is lysine; (v) wherein X5 is glutamine; (vi) wherein X6 is tyrosine; and (vii) wherein X7 is serine. In some embodiments, the prostate specific membrane antigen binding protein of the above embodiment has a higher affinity towards a human prostate specific membrane antigen than that of a binding protein which has the sequence set forth as SEQ ID NO. 4. In some embodiments, the prostate specific membrane antigen binding comprises any combination of the following: (i) wherein X$_1$ is proline; wherein X$_5$ is glutamine; (ii) wherein X$_6$ is tyrosine; wherein X$_4$ is lysine and X$_7$ is serine; (iii) wherein X$_2$ is histidine, X$_3$ is aspartic acid, X$_4$ is lysine, and X$_7$ is serine; (iv) wherein X$_1$ is proline, X$_2$ is histidine, X$_3$ is aspartic acid, and X$_7$ is serine; (v) wherein X$_2$ is histidine, X$_3$ is aspartic acid, X$_5$ is glutamine, and X$_7$ is serine; (vi) wherein X$_2$ is histidine, X$_3$ is aspartic acid, X$_4$ is lysine, and X$_7$ is serine; (vii) wherein X$_1$ is proline, X$_2$ is histidine, X$_3$ is aspartic acid, and X$_7$ is serine; (viii) wherein X$_2$ is histidine, X$_3$ is aspartic acid, X$_5$ is glutamine, and X$_7$ is serine; (ix) wherein X$_2$ is histidine, X$_3$ is aspartic acid, X$_6$ is tyrosine, and X$_7$ is serine; and (x) wherein X$_2$ is histidine, X$_3$ is aspartic acid, and X$_7$ is serine.

In some embodiments, the PSMA binding protein has an amino acid sequence as set forth in SEQ ID No. 4. In some embodiments, the PSMA binding protein has an amino acid sequence as set forth in SEQ ID No. 4 wherein one or more amino acid positions are substituted. In some embodiments, one or more of amino acid positions 19, 86, 87, and 106 of SEQ ID No. 4 are substituted. Exemplary substitutions in amino acid positions 19, 86, 87, and 106, include but are not limited to T19R, K86R, P87A, and Q106L. In some embodiments, one or more of amino acid positions 31, 33, 50, 55, 56, 62, and 97 of SEQ ID No. 4 are substituted. In some embodiments, amino acid position 31 of SEQ ID No.4 is substituted as E31P. In some embodiments, amino acid position 33 of SEQ ID No.4 is substituted as S33H. In some embodiments, amino acid position 50 of SEQ ID No.4 is substituted as T50D. In some embodiments, amino acid position 55 of SEQ ID No.4 is substituted as G55K. In some embodiments, amino acid position 56 of SEQ ID No.4 is substituted as T56Q. In some embodiments, amino acid position 62 of SEQ ID No.4 is substituted as S62Y. In some embodiments, amino acid position 97 of SEQ ID No.4 is substituted as G97S. In some embodiments, amino acid positions 33 and of SEQ ID No.4 is substituted as S33H. In some embodiments, the substitution of SEQ ID No. 4 at position 31 is combined with substitutions at positions 50 and 97. In some embodiments, the amino acid positions 31, 50, and 97 of SEQ ID No. 4 are respectively substituted as E31P, T50D, and G97S. In some embodiments, the substitution of SEQ ID No. 4 at position 33 is combined with substitutions at position 97. In some embodiments, the amino acid positions 33 and 97 of SEQ ID No. 4 are respectively substituted as S33H and G97S. In some embodiments, the substitution of SEQ ID No. 4 at position 33 is combined with substitutions at positions 50 and 97. In some embodiments, the amino acid positions 33, 50, and 97 of SEQ ID No. 4 are respectively substituted as S33H, T50D, and G97S. In some embodiments, the substitution of SEQ ID No. 4 at position 33 is combined with substitutions at positions 50, 55 and 97. In some embodiments, the amino acid positions 33, 50, 55 and 97 of SEQ ID No. 4 are respectively substituted as S33H, T50D, G55K, and G97S. In some embodiments, the substitution of SEQ ID No. 4 at position 33 is combined with substitutions at positions 31, 50, and 97. In some embodiments, the amino acid positions 31, 33, 50, and 97 of SEQ ID No. 4 are respectively substituted as E31P, S33H, T50D, and G97S. In some embodiments, the substitution of SEQ ID No. 4 at position 33 is combined with substitutions at positions 50, 56, and 97. In some embodiments, the amino acid positions 33, 50, 56, and 97 of SEQ ID No. 4 are respectively substituted as S33H, T50D, T56Q, and G97S. In some embodiments, the substitution of SEQ ID No. 4 at position 33 is combined with substitutions at positions 50, 62, and 97. In some embodiments, the amino acid positions 33, 50, 62, and 97 of SEQ ID No. 4 are respectively substituted as S33H, T50D, S62Y, and G97S.

In some embodiments, the PSMA binding protein has an amino acid sequence as set forth in SEQ ID No. 19 In some embodiments, the PSMA binding protein has an amino acid sequence as set forth in SEQ ID No. 19 wherein one or more amino acid positions are substituted. In some embodiments, one or more of amino acid positions 31, 33, 50, 55, 56, 62, and 97 of SEQ ID No. 19 are substituted. In some embodiments, amino acid position 31 of SEQ ID No.4 is substituted as E31P. In some embodiments, amino acid position 33 of SEQ ID No. 19 is substituted as S33H. In some embodiments, amino acid position 50 of SEQ ID No. 19 is substituted as T50D. In some embodiments, amino acid position 55 of SEQ ID No. 19 is substituted as G55K. In some embodiments, amino acid position 56 of SEQ ID No. 19 is substituted as T56Q. In some embodiments, amino acid position 62 of SEQ ID No. 19 is substituted as S62Y. In some embodiments, amino acid position 97 of SEQ ID No. 19 is substituted as G97S. In some embodiments, amino acid positions 33 and of SEQ ID No. 19 is substituted as S33H. In some embodiments, the substitution of SEQ ID No. 19 at position 31 is combined with substitutions at positions 50 and 97. In some embodiments, the amino acid positions 31, 50, and 97 of SEQ ID No. 19 are respectively substituted as E31P, T50D, and G97S. In some embodiments, the substitution of SEQ ID No. 19 at position 33 is combined with substitutions at position 97. In some embodiments, the amino acid positions 33 and 97 of SEQ ID No. 19 are respectively substituted as S33H and G97S. In some embodiments, the substitution of SEQ ID No. 19 at position 33 is combined with substitutions at positions 50 and 97. In some embodiments, the amino acid positions 33, 50, and 97 of SEQ ID No. 19 are respectively substituted as S33H, T50D, and G97S. In some embodiments, the substitution of SEQ ID No. 19 at position 33 is combined with substitutions at positions 50, 55 and 97. In some embodiments, the amino acid positions 33, 50, 55 and 97 of SEQ ID No. 19 are respectively substituted as S33H, T50D, G55K, and G97S. In some embodiments, the substitution of SEQ ID No. 19 at position 33 is combined with substitutions at positions 31, 50, and 97. In some embodiments, the amino acid positions 31, 33, 50, and 97 of SEQ ID No. 19 are respectively substituted as E31P, S33H, T50D, and G97S. In some embodiments, the substitution of SEQ ID No. 19 at position 33 is combined with substitutions at positions 50, 56, and 97. In some embodiments, the amino acid positions 33, 50, 56, and 97 of SEQ ID No. 19 are respectively substituted as S33H, T50D, T56Q, and G97S. In some embodiments, the substitution of SEQ ID No. 4 at position 33 is combined with substitutions at positions 50, 62, and 97. In some embodiments, the amino acid positions 33, 50, 62, and 97 of SEQ ID No. 4 are respectively substituted as S33H, T50D, S62Y, and G97S.

In some embodiments, the prostate specific membrane antigen binding protein comprises any combination of the following: (i) substitution at position 31; (ii) substitution at position 50; (iii) substitution at position 55; substitution at position 56; (iv) substitution at position 62; (v) substitution at position 97; (vi) substitutions at positions 55 and 97; (vii) substitutions at positions 33 and 97; (viii) substitutions at 33, 50, and 97; (ix) substitutions at 31, 33, 50, and 97; (x) substitutions at positions 33, 50, 55, and 97; (xi) substitutions at positions 33, 50, 56, and 97; and (xiii) substitutions at positions 33, 50, 62, and 97.

In some embodiments, the PSMA binding protein is cross-reactive with human and cynomolgus PSMA. In some embodiments, the PSMA binding protein is specific for human PSMA. In various embodiments, the PSMA binding protein of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID No. 4.

In various embodiments, the PSMA binding protein of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID No. 19.

In various embodiments, a complementarity determining region of the PSMA binding protein of the present disclosure is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID No. 16.

In various embodiments, a complementarity determining region of the PSMA binding protein of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID No. 17.

In various embodiments, a complementarity determining region of the PSMA binding protein PSMA binding protein of the present disclosure is at least about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID No. 18.

Humanization and Affinity Maturation

In designing binding proteins for therapeutic applications, it is desirable to create proteins that, for example, modulate a functional activity of a target, and/or improved binding proteins such as binding proteins with higher specificity and/or affinity and/or and binding proteins that are more bioavailable, or stable or soluble in particular cellular or tissue environments.

The PSMA binding proteins described in the present disclosure exhibit improved the binding affinities towards the target binding domain, which is PSMA. The present disclosure identifies amino acid substitutions in the complementarity determining regions (CDRs) of the PSMA binding proteins described herein which lead to higher binding affinity towards one or both of human and cyno PSMA. In some embodiments, the PSMA binding protein is an antibody. In certain embodiments, the PSMA binding protein is a humanized antibody. Generally, a humanized antibody comprises one or more variable domains in which CDRs or portions of CDRs are derived from a non-human antibody, and framework regions or portions of framework regions are derived from human antibody sequences. Optionally, a humanized antibody also comprises at least a portion of a human constant region. In some embodiments, selected framework residues are substituted with corresponding residues from a non-human antibody (e.g., the antibody from which the CDRs are derived), e.g., to restore or improve antibody specificity, affinity, or pH dependence. Human framework regions that can be used for humanization include but are not limited to framework regions selected using a best-fit method (e.g., Sims et al. J Immunol 151: 2296, 1993); framework regions derived from the consensus sequence of human antibodies of a particular subgroup of light or heavy chain variable regions (e.g., Carter et al. Proc Natl Acad Sci USA, 89:4285, 1992; and Presta et al., J Immunol, 151:2623, 1993); human mature (somatically mutated) framework regions or human germline framework regions (e.g., Almagro and Fransson, Front Biosci 13:1619-1633, 2008); and framework regions derived from screening framework libraries (e.g., Baca et al., J Biol Chem 272: 10678-10684, 1997; and Rosok et al., J Biol Chem 271: 22611-22618, 1996)). Thus, in one aspect, the PSMA binding protein comprises a humanized or human antibody or an antibody fragment. In one embodiment, the humanized or human anti-PSMA binding protein comprises one or more (e.g., all three) light chain complementary determining region 1 (LC CDR1), light chain complementary determining region 2 (LC CDR2), and light chain complementary determining region 3 (LC CDR3) of a humanized or human anti-PSMA binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-PSMA binding domain described herein, e.g., a humanized or human anti-PSMA binding domain comprising one or more, e.g., all three, LC CDRs and one or more, e.g., all three, HC CDRs. In some embodiments, the humanized or human anti-PSMA binding domain comprises a humanized or human light chain variable region specific to PSMA where the light chain variable region specific to PSMA comprises human or non-human light chain CDRs in a human light chain framework region. In certain instances, the light chain framework region is a λ (lambda) light chain framework. In other instances, the light chain framework region is a κ (kappa) light chain framework. In some embodiments, the humanized or human anti-PSMA binding domain comprises a humanized or human heavy chain variable region specific to PSMA where the heavy chain variable region specific to PSMA comprises human or non-human heavy chain CDRs in a human heavy chain framework region. In certain instances, the complementary determining regions of the heavy chain and/or the light chain are derived from known anti-PSMA antibodies, such as, for example, 7E11, EPR6253, 107.1A4, GCP-05, EP3253, BV9, SP29, human PSMA/FOLH1/NAALADase I antibody.

The PSMA binding proteins of the present disclosure is, in some embodiments, affinity matured to increase its binding affinity to the target binding domain. Where it is desired to improve the affinity of the PSMA binding proteins of the disclosure, such as anti-PSMA antibodies, containing one or more of the above-mentioned CDRs, such antibodies with improved affinity may be obtained by a number of affinity maturation protocols, including but not limited to maintaining the CDRs, chain shuffling, use of mutation strains of E. coli, DNA shuffling, phage display and sexual. Above exemplary methods of affinity maturation are discussed by Vaughan et al. (Nature Biotechnology, 16, 535-539, 1998). Thus, in addition to the PSMA binding protein variants discussed in the foregoing sections, the disclosure provides further sequence variants which improve the affinity of the binding protein towards its target, i.e., PSMA. In certain embodiments, such sequence variants comprise one or more semi-conservative or conservative substitutions within the PSMA binding protein sequences and such substitutions preferably do not significantly affect the desired activity of the binding protein. Substitutions may be naturally occurring or may be introduced for example using mutagenesis (e.g., Hutchinson et al., 1978, J. Biol. Chem. 253:6551). For example, the amino acids glycine, alanine, valine, leucine and isoleucine can often be substituted for one another (amino acids having aliphatic side chains). Of these possible substitutions, it is typically glycine and alanine are used to substitute for one another since they have relatively short side chains and valine, leucine, and isoleucine are used to substitute for one another since they have larger aliphatic side chains which are hydrophobic. Other amino acids which may often be substituted for one another include but are not limited to: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur-containing side chains).

In some embodiments, the PSMA binding proteins are isolated by screening combinatorial libraries, for example, by generating phage display libraries and screening such libraries for antibodies possessing the desired binding characteristics. Further, the binding affinity of the PSMA binding protein towards its binding target can be selected so as to target a specific elimination half-time in a particular PSMA albumin binding protein. Thus, in some embodiments, the PSMA binding protein has a high binding affinity towards its binding target. In other embodiments, the PSMA binding protein has a medium binding affinity towards its binding target. In yet other embodiments, the PSMA binding protein has a low or marginal binding affinity towards its binding target. Exemplary binding affinities include Kd of 10 nM or less (high), between 10 nM and 100 nM (medium), and greater than 100 nM (low). The affinity to bind to PSMA can be determined, for example, by the ability of binding protein itself or its PSMA binding domain to bind to PSMA coated on an assay plate; displayed on a microbial cell surface; in solution; etc. The binding activity of the protein of the present disclosure to PSMA can also be assayed by immobilizing the ligand (e.g., PSMA) or said binding protein itself or its PSMA binding domain, to a bead, substrate, cell, etc. In some embodiments, binding between the PSMA binding protein itself, or its PSMA binding domain, and a target ligand (such as PSMA) is determined, for example, by a binding kinetics assay. The binding kinetics assay, in certain embodiments, is carried out using an OCTET® system. In such embodiments, a first step comprises immobilizing a ligand (e.g., biotinylated PSMA) onto the surface of a biosensor (e.g., a streptavidin biosensor) at an optimal loading density, followed by a wash with an assay buffer to remove unbound ligands, which is followed by association of the analyte, i.e., the PSMA binding protein itself or its PSMA binding domain with the ligand, which is followed by exposing the biosensor to a buffer that does not contain the analyte, thereby resulting in dissociation of the PSMA binding protein itself or its PSMA binding domain from the ligand. Suitable blocking agents, such as BSA, Casein, Tween-20, PEG, gelatin, are used to block the non-specific binding sites on the bio-sensor. The binding kinetics data is subsequently analyzed using an appropriate software (e.g., ForteBio's Octet software) to determine the association and dissociation rate constants for binding interaction between the PSMA binding protein itself or its PSMA binding domain and a ligand.

In certain embodiments, the PSMA binding protein disclosed herein binds to human PSMA with a human Kd (hKd). In certain embodiments, the PSMA binding protein disclosed herein binds to cynomolgus PSMA with a cyno Kd (cKd). In certain embodiments, the PSMA binding protein disclosed herein binds to cynomolgus PSMA with a cyno Kd (cKd) and to human PSMA with a human Kd (hKd). In some embodiments, the hKd and the cKd range from about 0.1 nM to about 500 nM. In some embodiments, the hKd and the cKd range from about 0.1 nM to about 450 nM. In some embodiments, the hKd and the cKd range from about 0.1 nM to about 400 nM. In some embodiments, the hKd and the cKd range from about 0.1 nM to about 350 nM. In some embodiments, the hKd and the cKd range from about 0.1 nM to about 300 nM. In some embodiments, the hKd and the cKd range from about 0.1 nM to about 250 nM. In some embodiments, the hKd and the cKd range from about 0.1 nM to about 200 nM. In some embodiments, the hKd and the cKd range from about 0.1 nM to about 150 nM. In some embodiments, the hKd and the cKd range from about 0.1 nM to about 100 nM. In some embodiments, the hKd and the cKd range from about 0.1 nM to about 90 nM. In some embodiments, the hKd and the cKd range from about 0.2 nM to about 80 nM. In some embodiments, the hKd and the cKd range from about 0.3 nM to about 70 nM. In some embodiments, the hKd and the cKd range from about 0.4 nM to about 50 nM. In some embodiments, the hKd and the cKd range from about 0.5 nM to about 30 nM. In some embodiments, the hKd and the cKd range from about 0.6 nM to about 10 nM. In some embodiments, the hKd and the cKd range from about 0.7 nM to about 8 nM. In some embodiments, the hKd and the cKd range from about 0.8 nM to about 6 nM. In some embodiments, the hKd and the cKd range from about 0.9 nM to about 4 nM. In some embodiments, the hKd and the cKd range from about 1 nM to about 2 nM. In some embodiments, the PSMA binding protein binds to human and cynomolgus PSMA with comparable binding affinity (Kd).

In some embodiments, the PSMA binding protein of the present disclosure comprises the sequence as set forth in SEQ ID No. 4 and has an hKd of about 10 nM to about 20 nM. In some embodiments, the PSMA binding protein of the present disclosure comprises a glutamic acid to proline mutation in amino acid position 31 of SEQ ID No. 4 and has an hKd of about 5 nM to about 10 nM. In some embodiments, the PSMA binding protein of the present disclosure comprises a threonine to glutamine mutation in amino acid position 56 of SEQ ID No. 4 and has a hKd of about 1 nM to about 7 nM. In some embodiments, the PSMA binding protein of the present disclosure comprises a glycine to lysine mutation in amino acid position 55 of SEQ ID No. 4 and has a hKd of about 0.5 nM to about 5 nM. In some embodiments, the PSMA binding protein of the present disclosure comprises a serine to histidine mutation in amino acid position 33, threonine to aspartic acid in amino acid position 50, and glycine to serine substitution in amino acid position 97 of SEQ ID No. 4 and has an hKd of about 5 nM to about 10 nM. In some embodiments, the PSMA binding protein of the present disclosure comprises a serine to histidine mutation in amino acid position 33, and glycine to serine substitution in amino acid position 97 of SEQ ID No. 4 and has an hKd of about 0.05 nM to about 2 nM. Thus, in various embodiments, the PSMA binding proteins comprising one or more substitutions compared to the sequence as set forth in SEQ ID No. 4 have binding affinities towards human PSMA that are 1.5 times to about 300 times higher that of a protein comprising the sequence of SEQ ID No. 4 without any substitutions. For example, the binding affinity is about 1.5 times to about 3 times higher when the substitution(s) of SEQ ID No. 4 comprises E31P; about 2 times to about 15 times higher when the substitution(s) of SEQ ID No. 4 comprises T56Q; about 3 times to about 30 times the substitution(s) of SEQ ID No. 4 comprises G55K; about 2 times to about 3 times the substitution(s) of SEQ ID No. 4 comprises S33H T50D G97S; and about 5 times to about 300 times the substitution(s) of SEQ ID No. 4 comprises S33H G97S. In some embodiments, the one or more amino acid substitutions of SEQ ID No. 4, as described above, leads to enhanced binding affinity towards both human and cynomolgus PSMA, for example, a PSMA binding protein of the present disclosure comprising amino acid substitutions S33H and G97S in SEQ ID No. 4, shows increased affinity towards human and cynomolgus PSMA compared to a protein that comprises the sequence of SEQ ID No. 4 without any substitutions. A further example of such dual affinity enhancement is seen in case of a PSMA binding protein comprising amino acid substitutions S33H, T50D, and G97S in SEQ ID No. 4. In some embodiments, any of the foregoing PSMA binding proteins (e.g., anti-PSMA single domain antibodies of SEQ ID Nos. 21-32) are affinity peptide tagged for ease of purification. In some embodiments, the affinity peptide tag is six consecutive histidine residues, also referred to as 6his (SEQ ID NO: 33).

The binding affinity of PSMA binding proteins, e.g., an anti-PSMA single domain antibody, of the present disclosure may also be described in relative terms or as compared to the binding affinity of a second binding protein that also specifically binds to PSMA (e.g., a second anti-PSMA single domain antibody that is PSMA-specific, which may be referred to herein as a "second PSMA-specific antibody". In some embodiments, the second PSMA-specific antibody is any of the PSMA binding protein variants described herein, such as binding proteins defined by SEQ ID Nos. 21-32. Accordingly, certain embodiments of the present disclosure relate to an anti-PSMA single domain antibody that binds to human PSMA and/or cynomolgus PSMA with greater affinity than the binding protein of SEQ ID No. 4, or with a Kd that is lower than the Kd of the binding protein of SEQ ID No. 4. Further, additional embodiments of the present disclosure relate to an anti-PSMA single domain antibody that binds to human PSMA and/or cynomolgus PSMA with greater affinity than the binding protein of SEQ ID No. 19, or with a Kd that is lower than the Kd of the binding protein of SEQ ID No. 19.

CD3 Binding Domain

The specificity of the response of T cells is mediated by the recognition of antigen (displayed in context of a major histocompatibility complex, MHC) by the T cell receptor complex. As part of the T cell receptor complex, CD3 is a protein complex that includes a CD3γ (gamma) chain, a CD3δ (delta) chain, and two CD3ε (epsilon) chains which are present on the cell surface. CD3 associates with the α (alpha) and β (beta) chains of the T cell receptor (TCR) as well as and CD3 ζ (zeta) altogether to comprise the T cell receptor complex. Clustering of CD3 on T cells, such as by immobilized anti-CD3 antibodies leads to T cell activation similar to the engagement of the T cell receptor but independent of its clone-typical specificity.

In one aspect is described herein a multispecific protein comprising a PSMA binding protein according to the present disclosure. In some embodiments, the multispecific protein further comprises a domain which specifically binds to CD3. In some embodiments, the multispecific protein further comprises a domain which specifically binds to CD3γ. In some embodiments, the multispecific protein further comprises a domain which specifically binds to CD3δ. In some embodiments, the multispecific protein further comprises a domain which specifically binds to CD3ε.

In additional embodiments, the multispecific protein further comprises a domain which specifically binds to the T cell receptor (TCR). In some embodiments, the multispecific protein further comprises a domain which specifically binds the α chain of the TCR. In some embodiments, the multispecific protein further comprises a domain which specifically binds the β chain of the TCR.

In some embodiments, the multispecific protein further comprises a domain which specifically binds to a bulk serum protein, such as human serum albumin (HSA). In some embodiments, the HSA binding domain comprises a sequence selected from the group consisting of SEQ ID NO. 123-146.

In some embodiments, the multispecific protein is a PSMA targeting trispecific antigen-binding protein, also referred to herein as a PSMA targeting TRITAC™ molecule or PSMA trispecific molecule or trispecific molecule.

In certain embodiments, the CD3 binding domain of the multispecific protein comprising a PSMA binding protein described herein exhibits not only potent CD3 binding affinities with human CD3, but show also excellent cross-reactivity with the respective cynomolgus monkey CD3 proteins. In some instances, the CD3 binding domain of the multispecific proteins are cross-reactive with CD3 from cynomolgus monkey.

In some embodiments, the CD3 binding domain of the multispecific protein comprising a PSMA binding protein described herein can be any domain that binds to CD3 including but not limited to domains from a monoclonal antibody, a polyclonal antibody, a recombinant antibody, a human antibody, a humanized antibody, or antigen binding fragments of the CD3 binding antibodies, such as single domain antibodies (sdAb), Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some instances, it is beneficial for the CD3 binding domain to be derived from the same species in which the multispecific protein comprising a single PSMA binding protein described herein will ultimately be used in. For example, for use in humans, it may be beneficial for the CD3 binding domain of the multispecific protein comprising a PSMA binding protein described herein to comprise human or humanized residues from the PSMA binding domain of an antibody or antibody fragment.

Thus, in one aspect, the CD3 binding domain of the multispecific protein comprising a PSMA binding protein comprises a humanized or human antibody or an antibody fragment, or a murine antibody or antibody fragment. In one embodiment, the humanized or human anti-CD3 binding domain comprises one or more (e.g., all three) light chain complementary determining regions, light chain complementary determining region 1 (LC CDR1), light chain complementary determining region 2 (LC CDR2), and light chain complementary determining region 3 (LC CDR3) of a humanized or human anti-CD3 binding domain described herein, and/or one or more (e.g., all three) heavy chain complementary determining regions, heavy chain complementary determining region 1 (HC CDR1), heavy chain complementary determining region 2 (HC CDR2), and heavy chain complementary determining region 3 (HC CDR3) of a humanized or human anti-CD3 binding domain described herein, e.g., a humanized or human anti-CD3 binding domain comprising one or more, e.g., all three, LC CDRs and one or more, e.g., all three, HC CDRs.

In some embodiments, the humanized or human anti-CD3 binding domain comprises a humanized or human light chain variable region specific to CD3 where the light chain variable region specific to CD3 comprises human or non-human light chain CDRs in a human light chain framework region. In certain instances, the light chain framework region is a λ (lambda) light chain framework. In other instances, the light chain framework region is a κ (kappa) light chain framework.

In some embodiments, the humanized or human anti-CD3 binding domain comprises a humanized or human heavy chain variable region specific to CD3 where the heavy chain variable region specific to CD3 comprises human or non-human heavy chain CDRs in a human heavy chain framework region.

In certain instances, the complementary determining regions of the heavy chain and/or the light chain are derived from known anti-CD3 antibodies, such as, for example, muromonab-CD3 (OKT3), otelixizumab (TRX4), teplizumab (MGA031), visilizumab (Nuvion), SP34, TR-66 or X35-3, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

In one embodiment, the anti-CD3 binding domain is a single chain variable fragment (scFv) comprising a light chain and a heavy chain of an amino acid sequence provided herein. As used herein, "single chain variable fragment" or "scFv" refers to an antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived. In an embodiment, the anti-CD3 binding domain comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In one embodiment, the humanized or human anti-CD3 binding domain is a scFv, and a light chain variable region comprising an amino acid sequence described herein, is attached to a heavy chain variable region comprising an amino acid sequence described herein, via a scFv linker. The light chain variable region and heavy chain variable region of a scFv can be, e.g., in any of the following orientations: light chain variable region-scFv linker-heavy chain variable region or heavy chain variable region-scFv linker-light chain variable region.

In some instances, scFvs which bind to CD3 are prepared according to known methods. For example, scFv molecules can be produced by linking VH and VL regions together using flexible polypeptide linkers. The scFv molecules comprise a scFv linker (e.g., a Ser-Gly linker) with an optimized length and/or amino acid composition. Accordingly, in some embodiments, the length of the scFv linker is such that the VH or VL domain can associate intermolecularly with the other variable domain to form the CD3 binding site. In certain embodiments, such scFv linkers are "short", i.e. consist of 0, 1, 2, 3, 4, 5, 6, 7, 8, 9, 10, 11 or 12 amino acid residues. Thus, in certain instances, the scFv linkers consist of about 12 or less amino acid residues. In the case of 0 amino acid residues, the scFv linker is a peptide bond. In some embodiments, these scFv linkers consist of about 3 to about 15, for example 8, 9 or 10 contiguous amino acid residues. Regarding the amino acid composition of the scFv linkers, peptides are selected that confer flexibility, do not interfere with the variable domains as well as allow interchain folding to bring the two variable domains together to form a functional CD3 binding site. For example, scFv linkers comprising glycine and serine residues generally provide protease resistance. In some embodiments, linkers in a scFv comprise glycine and serine residues. The amino acid sequence of the scFv linkers can be optimized, for example, by phage-display methods to improve the CD3 binding and production yield of the scFv. Examples of peptide scFv linkers suitable for linking a variable light chain domain and a variable heavy chain domain in a scFv include but are not limited to (GS)$_n$ (SEQ ID NO: 157), (GGS)$_n$ (SEQ ID NO: 158), (GGGS)$_n$ (SEQ ID NO: 159), (GGSG)$_n$ (SEQ ID NO: 160), (GGSGG)$_n$ (SEQ ID NO: 161), or (GGGGS)$_n$ (SEQ ID NO: 162), wherein n is 1, 2, 3, 4, 5, 6, 7, 8, 9, or 10. In one embodiment, the scFv linker can be (GGGGS)$_4$ (SEQ ID NO: 163) or (GGGGS)$_3$ (SEQ ID NO: 164). Variation in the linker length may retain or enhance activity, giving rise to superior efficacy in activity studies.

In some embodiments, CD3 binding domain of PSMA trispecific antigen-binding protein has an affinity to CD3 on CD3 expressing cells with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In some embodiments, the CD3 binding domain of PSMA trispecific antigen-binding protein has an affinity to CD3ε, γ, or δ with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In further embodiments, CD3 binding domain of PSMA trispecific antigen-binding protein has low affinity to CD3, i.e., about 100 nM or greater.

The affinity to bind to CD3 can be determined, for example, by the ability of the PSMA trispecific antigen-binding protein itself or its CD3 binding domain to bind to CD3 coated on an assay plate; displayed on a microbial cell surface; in solution; etc. The binding activity of the PSMA trispecific antigen-binding protein itself or its CD3 binding domain of the present disclosure to CD3 can be assayed by immobilizing the ligand (e.g., CD3) or the PSMA trispecific antigen-binding protein itself or its CD3 binding domain, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed, for example, by Surface Plasmon Resonance (SPR).

In some embodiments, CD3 binding domains described herein comprise a polypeptide having a sequence described in Table 7 (SEQ ID NO: 34-88) and subsequences thereof. In some embodiments, the CD3 binding domain comprises a polypeptide having at least 70%-95% or more homology to a sequence described in Table 7 (SEQ ID NO: 34-122). In some embodiments, the CD3 binding domain comprises a polypeptide having at least 70%, 75%, 80%, 85%, 90%, 95%, or more homology to a sequence described in Table 7 (SEQ ID NO: 34-122). In some embodiments, the CD3 binding domain has a sequence comprising at least a portion of a sequence described in Table 7 (SEQ ID NO: 34-122). In some embodiments, the CD3 binding domain comprises a polypeptide comprising one or more of the sequences described in Table 7 (SEQ ID NO: 34-122).

In certain embodiments, CD3 binding domain comprises an scFv with a heavy chain CDR1 comprising SEQ ID NO: 49, and 56-67. In certain embodiments, CD3 binding domain comprises an scFv with a heavy chain CDR2 comprising SEQ ID NO: 50, and 68-77. In certain embodiments, CD3 binding domain comprises an scFv with a heavy chain CDR3 comprising SEQ ID NO: 51, and 78-87. In certain embodiments, CD3 binding domain comprises an scFv with a light chain CDR1 comprising SEQ ID NO: 53, and 88-100. In certain embodiments, CD3 binding domain comprises an scFv with a light chain CDR2 comprising SEQ ID NO: 54, and 101-113. In certain embodiments, CD3 binding domain comprises an scFv with a light chain CDR3 comprising SEQ ID NO: 55, and 114-120.

The affinity to bind to CD3 can be determined, for example, by the ability of the multispecific protein comprising a PSMA binding protein itself or its CD3 binding domain to bind to CD3 coated on an assay plate; displayed on a microbial cell surface; in solution; etc. The binding activity of multispecific protein comprising a PSMA binding protein itself or its CD3 binding domain according to the present disclosure to CD3 can be assayed by immobilizing the ligand (e.g., CD3) or said multispecific protein itself or its CD3 binding domain, to a bead, substrate, cell, etc. The binding activity of the multispecific protein comprising a PSMA binding protein itself or its CD3 binding domain to bind to CD3 can be determined by immobilizing the ligand (e.g., CD3) or said multispecific protein itself or its PSMA binding domain, to a bead, substrate, cell, etc. In some embodiments, binding between the multispecific protein comprising a PSMA binding protein, and a target ligand (such as CD3) is determined, for example, by a binding kinetics assay. The binding kinetics assay, in certain embodiments, is carried out using an OCTET® system. In such embodiments, a first step comprises immobilizing a ligand (e.g., biotinylated CD3) onto the surface of a biosensor (e.g., a streptavidin biosensor) at an optimal loading density, followed by a wash with an assay buffer to remove unbound ligands; which is followed by association of the analyte, e.g., the the multispecific protein comprising a PSMA binding protein with the ligand; which is followed by exposing the biosensor to a buffer that does not contain the analyte, thereby resulting in dissociation of the the multispecific protein comprising a PSMA binding protein from the ligand. Suitable blocking agents, such as BSA, Casein, Tween-20, PEG, gelatin, are used to block the non-specific binding sites on the bio-sensor, during the kinetic assay. The binding kinetics data is subsequently analyzed using an appropriate software (e.g., ForteBio's Octet software) to determine the association and dissociation rate constants for binding interaction between the the multispecific protein comprising a PSMA binding protein and a ligand.

In one aspect, the PSMA targeting trispecific proteins comprise a domain (A) which specifically binds to CD3, a domain (B) which specifically binds to human serum albumin (HSA), and a domain (C) which specifically binds to PSMA. The three domains in PSMA targeting trispecific proteins are arranged in any order. Thus, it is contemplated that the domain order of the PSMA targeting trispecific proteins are:

$H_2N$-(A)-(B)-(C)-COOH,
$H_2N$-(A)-(C)-(B)-COOH,
$H_2N$-(B)-(A)-(C)-COOH,
$H_2N$-(B)-(C)-(A)-COOH,
$H_2N$-(C)-(B)-(A)-COOH, or
$H_2N$-(C)-(A)-(B)-COOH.

In some embodiments, the PSMA targeting trispecific proteins have a domain order of $H_2N$-(A)-(B)-(C)-COOH. In some embodiments, the PSMA targeting trispecific proteins have a domain order of $H_2N$-(A)-(C)-(B)-COOH. In some embodiments, the PSMA targeting trispecific proteins have a domain order of $H_2N$-(B)-(A)-(C)-COOH. In some embodiments, the PSMA targeting trispecific proteins have a domain order of $H_2N$-(B)-(C)-(A)-COOH. In some embodiments, the PSMA targeting trispecific proteins have a domain order of $H_2N$-(C)-(B)-(A)-COOH. In some embodiments, the PSMA targeting trispecific proteins have a domain order of $H_2N$-(C)-(A)-(B)-COOH.

In some embodiments, the PSMA targeting trispecific proteins have the HSA binding domain as the middle domain, such that the domain order is $H_2N$-(A)-(B)-(C)-COOH or $H_2N$-(C)-(B)-(A)-COOH. It is contemplated that in such embodiments where the HSA binding domain as the middle domain, the CD3 and PSMA binding domains are afforded additional flexibility to bind to their respective targets.

In some embodiments, the PSMA targeting trispecific proteins described herein comprise a polypeptide having a sequence described in Table 10 (SEQ ID NO: 147-156) and subsequences thereof. In some embodiments, the trispecific antigen binding protein comprises a polypeptide having at least 70%-95% or more homology to a sequence described in Table 10 (SEQ ID NO: 147-156). In some embodiments, the trispecific antigen binding protein comprises a polypeptide having at least 70%, 75%, 80%, 85%, 90%, 95%, or more homology to a sequence described in Table 10 (SEQ ID NO: 1470-156). In some embodiments, the trispecific antigen binding protein has a sequence comprising at least a portion of a sequence described in Table 10 (SEQ ID NO: 147-156). In some embodiments, the PSMA trispecific antigen-binding protein comprises a polypeptide comprising one or more of the sequences described in Table 10 (SEQ ID NO: 147-156). In further embodiments, the PSMA trispecific antigen-binding protein comprises one or more CDRs as described in the sequences in Table 10 (SEQ ID NO: 147-156).

The PSMA targeting trispecific proteins described herein are designed to allow specific targeting of cells expressing PSMA by recruiting cytotoxic T cells. This improves efficacy compared to ADCC (antibody dependent cell-mediated cytotoxicity), which is using full length antibodies directed to a sole antigen and is not capable of directly recruiting cytotoxic T cells. In contrast, by engaging CD3 molecules expressed specifically on these cells, the PSMA targeting trispecific proteins can crosslink cytotoxic T cells with cells expressing PSMA in a highly specific fashion, thereby directing the cytotoxic potential of the T cell towards the target cell. The PSMA targeting trispecific proteins described herein engage cytotoxic T cells via binding to the surface-expressed CD3 proteins, which form part of the TCR. Simultaneous binding of several PSMA trispecific antigen-binding protein to CD3 and to PSMA expressed on the surface of particular cells causes T cell activation and mediates the subsequent lysis of the particular PSMA expressing cell. Thus, PSMA targeting trispecific proteins are contemplated to display strong, specific and efficient target cell killing. In some embodiments, the PSMA targeting trispecific proteins described herein stimulate target cell killing by cytotoxic T cells to eliminate pathogenic cells (e.g., tumor cells expressing PSMA). In some of such embodiments, cells are eliminated selectively, thereby reducing the potential for toxic side effects.

The PSMA targeting trispecific proteins described herein confer further therapeutic advantages over traditional monoclonal antibodies and other smaller bispecific molecules. Generally, the effectiveness of recombinant protein pharmaceuticals depends heavily on the intrinsic pharmacokinetics of the protein itself. One such benefit here is that the PSMA targeting trispecific proteins described herein have extended pharmacokinetic elimination half-time due to having a half-life extension domain such as a domain specific to HSA. In this respect, the PSMA targeting trispecific proteins described herein have an extended serum elimination half-time of about two, three, about five, about seven, about 10, about 12, or about 14 days in some embodiments. This contrasts to other binding proteins such as BiTE or DART molecules which have relatively much shorter elimination half-times. For example, the BiTE CD19×CD3 bispecific scFv-scFv fusion molecule requires continuous intravenous infusion (i.v.) drug delivery due to its short elimination half-time. The longer intrinsic half-times of the PSMA targeting trispecific proteins solve this issue thereby allowing for increased therapeutic potential such as low-dose pharmaceutical formulations, decreased periodic administration and/or novel pharmaceutical compositions.

The PSMA targeting trispecific proteins described herein also have an optimal size for enhanced tissue penetration and tissue distribution. Larger sizes limit or prevent penetration or distribution of the protein in the target tissues. The PSMA targeting trispecific proteins described herein avoid this by having a small size that allows enhanced tissue penetration and distribution. Accordingly, the PSMA targeting trispecific proteins described herein, in some embodiments have a size of about 50 kD to about 80 kD, about 50 kD to about 75 kD, about 50 kD to about 70 kD, or about 50 kD to about 65 kD. Thus, the size of the PSMA targeting trispecific proteins is advantageous over IgG antibodies which are about 150 kD and the BiTE and DART diabody molecules which are about 55 kD but are not half-life extended and therefore cleared quickly through the kidney.

In further embodiments, the PSMA targeting trispecific proteins described herein have an optimal size for enhanced tissue penetration and distribution. In these embodiments, the PSMA targeting trispecific proteins are constructed to be as small as possible, while retaining specificity toward its targets. Accordingly, in these embodiments, the PSMA targeting trispecific proteins described herein have a size of about 20 kD to about 40 kD or about 25 kD to about 35 kD to about 40 kD, to about 45 kD, to about 50 kD, to about 55 kD, to about 60 kD, to about 65 kD. In some embodiments, the PSMA targeting trispecific proteins described herein have a size of about 50 kD, 49, kD, 48 kD, 47 kD, 46 kD, 45 kD, 44 kD, 43 kD, 42 kD, 41 kD, 40 kD, about 39 kD, about 38 kD, about 37 kD, about 36 kD, about 35 kD, about 34 kD, about 33 kD, about 32 kD, about 31 kD, about 30 kD, about 29 kD, about 28 kD, about 27 kD, about 26 kD, about 25 kD, about 24 kD, about 23 kD, about 22 kD, about 21 kD, or about 20 kD. An exemplary approach to the small size is through the use of single domain antibody (sdAb) fragments for each of the domains. For example, a particular PSMA trispecific antigen-binding protein has an anti-CD3 sdAb, anti-HSA sdAb and an sdAb for PSMA. This reduces the size of the exemplary PSMA trispecific antigen-binding protein to under 40 kD. Thus in some embodiments, the domains of the PSMA targeting trispecific proteins are all single domain antibody (sdAb) fragments. In other embodiments, the PSMA targeting trispecific proteins described herein comprise small molecule entity (SME) binders for HSA and/or the PSMA. SME binders are small molecules averaging about 500 to 2000 Da in size and are attached to the PSMA targeting trispecific proteins by known methods, such as sortase ligation or conjugation. In these instances, one of the domains of PSMA trispecific antigen-binding protein is a sortase recognition sequence, e.g., LPETG (SEQ ID NO: 57). To attach a SME binder to PSMA trispecific antigen-binding protein with a sortase recognition sequence, the protein is incubated with a sortase and a SME binder whereby the sortase attaches the SME binder to the recognition sequence. Known SME binders include MIP-1072 and MIP-1095 which bind to prostate-specific membrane antigen (PSMA). In yet other embodiments, the domain which binds to PSMA of PSMA targeting trispecific proteins described herein comprise a knottin peptide for binding PSMA. Knottins are disulfide-stabilized peptides with a cysteine knot scaffold and have average sizes about 3.5 kD. Knottins have been contemplated for binding to certain tumor molecules such as PSMA. In further embodiments, domain which binds to PSMA of PSMA targeting trispecific proteins described herein comprise a natural PSMA ligand.

Another feature of the PSMA targeting trispecific proteins described herein is that they are of a single-polypeptide design with flexible linkage of their domains. This allows for facile production and manufacturing of the PSMA targeting trispecific proteins as they can be encoded by single cDNA molecule to be easily incorporated into a vector. Further, because the PSMA targeting trispecific proteins described herein are a monomeric single polypeptide chain, there are no chain pairing issues or a requirement for dimerization. It is contemplated that the PSMA targeting trispecific proteins described herein have a reduced tendency to aggregate unlike other reported molecules such as bispecific proteins with Fc-gamma immunoglobulin domains.

In the PSMA targeting trispecific proteins described herein, the domains are linked by internal linkers L1 and L2, where L1 links the first and second domain of the PSMA targeting trispecific proteins and L2 links the second and third domains of the PSMA targeting trispecific proteins. Linkers L1 and L2 have an optimized length and/or amino acid composition. In some embodiments, linkers L1 and L2 are the same length and amino acid composition. In other embodiments, L1 and L2 are different. In certain embodiments, internal linkers L1 and/or L2 are "short", i.e., consist of 0, 1, 2, 3, 4, 5, 6, 7, 8, 9, 10, 11 or 12 amino acid residues. Thus, in certain instances, the internal linkers consist of about 12 or less amino acid residues. In the case of 0 amino acid residues, the internal linker is a peptide bond. In certain embodiments, internal linkers L1 and/or L2 are "long", i.e., consist of 15, 20 or 25 amino acid residues. In some embodiments, these internal linkers consist of about 3 to about 15, for example 8, 9 or 10 contiguous amino acid residues. Regarding the amino acid composition of the internal linkers L1 and L2, peptides are selected with properties that confer flexibility to the PSMA targeting trispecific proteins, do not interfere with the binding domains as well as resist cleavage from proteases. For example, glycine and serine residues generally provide protease resistance. Examples of internal linkers suitable for linking the domains in the PSMA targeting trispecific proteins include but are not limited to $(GS)_n$ (SEQ ID NO: 157), $(GGS)_n$ (SEQ ID NO: 158), $(GGGS)_n$ (SEQ ID NO: 159), $(GGSG)_n$ (SEQ ID NO: 160), $(GGSGG)_n$ (SEQ ID NO: 161), or $(GGGGS)_n$ (SEQ ID NO: 162), wherein n is 1, 2, 3, 4, 5, 6, 7, 8, 9, or 10. In one embodiment, internal linker L1 and/or L2 is $(GGGGS)_4$ (SEQ ID NO: 163) or $(GGGGS)_3$ (SEQ ID NO: 164).

PSMA Binding Protein Modifications

The PSMA binding proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence to block an immunogenic domain and/or for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in PSMA binding proteins described herein, including the peptide backbone, the amino acid side-chains, and the amino or carboxyl termini. Certain common peptide modifications that are useful for modification of PSMA binding proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

Polynucleotides Encoding PSMA Binding Proteins

Also provided, in some embodiments, are polynucleotide molecules encoding a PSMA binding protein as described herein. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding the anti-PSMA binding protein, operably linked to a suitable promoter, and optionally a suitable transcription terminator, and expressing it in bacteria or other appropriate expression system such as, for example CHO cells.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described PSMA binding protein. Examples of expression vectors for expression in E. coli are pSKK (Le Gall et al., J Immunol Methods. (2004) 285(1): 111-27), pcDNA5 (Invitrogen) for expression in mammalian cells, PICHIAPINK™ Yeast Expression Systems (Invitrogen), BACUVANCE™ Baculovirus Expression System (GenScript).

Thus, the PSMA albumin binding proteins as described herein, in some embodiments, are produced by introducing a vector encoding the protein as described above into a host cell and culturing said host cell under conditions whereby the protein domains are expressed, may be isolated and, optionally, further purified.

Production of PSMA Binding Proteins

Disclosed herein, in some embodiments, is a process for the production of a PSMA binding protein. In some embodiments, the process comprises culturing a host transformed or transfected with a vector comprising a nucleic acid sequence encoding a PSMA binding protein under conditions allowing the expression of the PSMA binding protein and recovering and purifying the produced protein from the culture.

In an additional embodiment is provided a process directed to improving one or more properties, e.g., affinity, stability, heat tolerance, cross-reactivity, etc., of the PSMA binding proteins and/or the multispecific binding proteins comprising a PSMA binding protein described herein, compared to a reference binding compound. In some embodiments, a plurality of single-substitution libraries is provided each corresponding to a different domain, or amino acid segment of the PSMA binding protein or reference binding compound such that each member of the single-sub stitution library encodes only a single amino acid change in its corresponding domain, or amino acid segment. Typically, this allows all of the potential substitutions in a large protein or protein binding site to be probed with a few small libraries. In some embodiments, the plurality of domains forms or covers a contiguous sequence of amino acids of the PSMA binding protein or a reference binding compound. Nucleotide sequences of different single-substitution libraries overlap with the nucleotide sequences of at least one other single-substitution library. In some embodiments, a plurality of single-substitution libraries are designed so that every member overlaps every member of each single-sub stitution library encoding an adjacent domain.

Binding compounds expressed from such single-substitution libraries are separately selected to obtain a subset of variants in each library which has properties at least as good as those of the reference binding compound and whose resultant library is reduced in size. Generally, the number of nucleic acids encoding the selected set of binding compounds is smaller than the number of nucleic acids encoding members of the original single-substitution library. Such properties include, but are not limited to, affinity to a target compound, stability with respect to various conditions such as heat, high or low pH, enzymatic degradation, cross-reactivity to other proteins and the like. The selected compounds from each single-substitution library are referred to herein interchangeably as "pre-candidate compounds," or "pre-candidate proteins." Nucleic acid sequences encoding the pre-candidate compounds from the separate single-substitution libraries are then shuffled in a PCR to generate a shuffled library, using PCR-based gene shuffling techniques.

An exemplary work flow of the screening process is described herein. Libraries of pre-candidate compounds are generated from single substitution libraries and selected for binding to the target protein(s), after which the pre-candidate libraries are shuffled to produce a library of nucleic acids encoding candidate compounds which, in turn, are cloned into a convenient expression vector, such as a phagemid expression system. Phage expressing candidate compounds then undergo one or more rounds of selection for improvements in desired properties, such as binding affinity to a target molecule. Target molecules may be adsorbed or otherwise attached to a surface of a well or other reaction container, or target molecules may be derivatized with a binding moiety, such as biotin, which after incubation with candidate binding compounds may be captured with a complementary moiety, such as streptavidin, bound to beads, such as magnetic beads, for washing. In exemplary selection regimens, the candidate binding compounds undergo a wash step so that only candidate compounds with very low dissociation rates from a target molecule are selected. Exemplary wash times for such embodiments are about 10 minutes, about 15 minutes, about 20 minutes, about 20 minutes, about 30 minutes, about 35 minutes, about 40 minutes, about 45 minutes, about 50 minutes, about 55 mins, about 1 hour, about 2 hours, about 3 hours, about 4 hours, about 5 hours, about 6 hours, about 7 hours, about 8 hours; or in other embodiments, about 24 hours; or in other embodiments, about 48 hours; or in other embodiments, about 72 hours. Isolated clones after selection are amplified and subjected to an additional cycle of selection or analyzed, for example by sequencing and by making comparative measurements of binding affinity, for example, by ELISA, surface plasmon resonance (SPR), bio-layer interferometry (e.g., OCTET® system, Pall Life Sciences, ForteBio, Menlo Park, Calif.) or the like.

In some embodiments, the above process is implemented to identify one or more PSMA binding proteins with improved binding affinity, improved cross reactivity to a selected set of binding targets compared to that of a reference PSMA binding protein. In some embodiments, the reference binding protein is a protein having the amino acid sequence as set forth in SEQ ID No. 4. In some embodiments, the reference binding protein is a protein having the amino acid sequence as set forth in SEQ ID No. 19. In certain embodiments, single substitution libraries are prepared by varying codons in the VH region of the reference PSMA binding protein, including codons in framework regions and in the CDRs. In another embodiment, the locations where codons are varied comprise the CDRs of the heavy chain of the reference PSMA binding protein, or a subset of such CDRs, such as solely CDR1, solely CDR2, solely CDR3, or pairs thereof. In another embodiment, locations where codons are varied occur solely in framework regions. In some embodiments, a library comprises single codon changes solely from a reference PSMA binding protein solely in framework regions of VH numbering in the range of from 10 to 111. In another embodiment, the locations where codons are varied comprise the CDR3s of the heavy chain of the reference PSMA binding protein, or a subset of such CDR3s. In another embodiment, the number of locations where codons of VH encoding regions are varied are in the range of from 10 to 111, such that up to 80 locations are in framework region. After preparation of the single substitution library, as outlined above, the following steps are carried out: (a) expressing separately each member of each single substitution library as a pre-candidate protein; (b) selecting members of each single substitution library which encode pre-candidate proteins which bind to a binding partner that may or may not differ from the original binding target [e.g., a desired cross-reaction target(s)]; (c) shuffling members of the selected libraries in a PCR to produce a combinatorial shuffled library; (d) expressing members of the shuffled library as candidate PSMA binding proteins; and (e) selecting members of the shuffled library one or more times for candidate PSMA binding proteins which bind the original binding partner and potentially (f) further selecting the candidate proteins for binding to the desired cross-reactive target(s) thereby providing a nucleic acid encoded PSMA binding protein with increased cross reactivity for the one or more substances with respect to the reference PSMA binding protein without loss of affinity for the original ligand. In additional embodiments, the method may be implemented for obtaining a PSMA binding protein with decreased reactivity to a selected cross-reactive substance(s) or compound(s) or epitope(s) by substituting step (f) with the following step: depleting candidate binding compounds one or more times from the subset of candidate PSMA binding protein which bind to the undesired cross-reactive compound.

Pharmaceutical Compositions

Also provided, in some embodiments, are pharmaceutical compositions comprising a PSMA binding protein described herein, a vector comprising the polynucleotide encoding the polypeptide of the PSMA binding proteins or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

In some embodiments of the pharmaceutical compositions, the PSMA binding protein described herein is encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the PSMA binding protein is attached to liposomes. In some instances, the PSMA binding protein is conjugated to the surface of liposomes. In some instances, the PSMA binding protein is encapsulated within the shell of a liposome. In some instances, the liposome is a cationic liposome.

The PSMA binding proteins described herein are contemplated for use as a medicament. Administration is effected by different ways, e.g., by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

Methods of Treatment

Also provided herein, in some embodiments, are methods and uses for stimulating the immune system of an individual in need thereof comprising administration of a PSMA binding protein or a multispecific binding protein comprising the PSMA binding protein described herein. In some instances, the administration of a PSMA binding protein described herein induces and/or sustains cytotoxicity towards a cell expressing a target antigen. In some instances, the cell expressing a target antigen is a cancer or tumor cell, a virally infected cell, a bacterially infected cell, an autoreactive T or B cell, damaged red blood cells, arterial plaques, or fibrotic tissue.

Also provided herein are methods and uses for a treatment of a disease, disorder or condition associated with a target antigen comprising administering to an individual in need thereof a PSMA binding protein or a multispecific binding protein comprising the PSMA binding protein described herein. Diseases, disorders or conditions associated with a target antigen include, but are not limited to, viral infection, bacterial infection, auto-immune disease, transplant rejection, atherosclerosis, or fibrosis. In other embodiments, the disease, disorder or condition associated with a target antigen is a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In one embodiment, the disease, disorder or condition associated with a target antigen is cancer. In one instance, the cancer is a hematological cancer. In another instance, the cancer is a prostate cancer.

In some embodiments, the prostate cancer is an advanced stage prostate cancer. In some embodiments, the prostate cancer is drug resistant. In some embodiments, the prostate cancer is anti-androgen drug resistant. In some embodiments, the prostate cancer is metastatic. In some embodiments, the prostate cancer is metastatic and drug resistant (e.g., anti-androgen drug resistant). In some embodiments, the prostate cancer is castration resistant. In some embodiments, the prostate cancer is metastatic and castration resistant. In some embodiments, the prostate cancer is enzalutamide resistant. In some embodiments, the prostate cancer is enzalutamide and arbiraterone resistant. In some embodiments, the prostate cancer is enzalutamide, arbiraterone, and bicalutamide resistant. In some embodiments, the prostate cancer is docetaxel resistant. In some of these embodiments, the prostate cancer is enzalutamide, arbiraterone, bicalutamide, and docetaxel resistant.

In some embodiments, administering an anti-PSMA single domain antibody described herein or a PSMA targeting trispecific protein described herein inhibits prostate cancer cell growth; inhibits prostate cancer cell migration; inhibits prostate cancer cell invasion; ameliorates the symptoms of prostate cancer; reduces the size of a prostate cancer tumor; reduces the number of prostate cancer tumors; reduces the number of prostate cancer cells; induces prostate cancer cell necrosis, pyroptosis, oncosis, apoptosis, autophagy, or other cell death; or enhances the therapeutic effects of a compound selected from the group consisting of enzalutamide, abiraterone, docetaxel, bicalutamide, and any combinations thereof.

In some embodiments, the method comprises inhibiting prostate cancer cell growth by administering an anti-PSMA single domain antibody described herein or a PSMA targeting trispecific protein described herein. In some embodiments, the method comprises inhibiting prostate cancer cell migration by administering an anti-PSMA single domain antibody described herein or a PSMA targeting trispecific protein described herein. In some embodiments, the method comprises inhibiting prostate cancer cell invasion by administering an anti-PSMA single domain antibody described herein or a PSMA targeting trispecific protein described herein. In some embodiments, the method comprises ameliorating the symptoms of prostate cancer by administering an anti-PSMA single domain antibody described herein or a PSMA targeting trispecific protein described herein. In some embodiments, the method comprises reducing the size of a prostate cancer tumor by administering an anti-PSMA single domain antibody described herein or a PSMA targeting trispecific protein described herein. In some embodiments, the method comprises reducing the number of prostate cancer tumors by administering an anti-PSMA single domain antibody described herein or a PSMA targeting trispecific protein described herein. In some embodiments, the method comprises reducing the number of prostate cancer cells by administering an anti-PSMA single domain antibody described herein or a PSMA targeting trispecific protein described herein. In some embodiments, the method comprises inducing prostate cancer cell necrosis, pyroptosis, oncosis, apoptosis, autophagy, or other cell death by administering a PSMA targeting trispecific protein described herein.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

In some embodiments of the methods described herein, the PSMA binding proteins or a multispecific binding protein comprising the PSMA binding protein described herein are administered in combination with an agent for treatment of the particular disease, disorder or condition. Agents include but are not limited to, therapies involving antibodies, small molecules (e.g., chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, the PSMA binding protein or a multispecific binding protein comprising the PSMA binding protein described herein are administered in combination with anti-diarrheal agents, anti-emetic agents, analgesics, opioids and/or non-steroidal anti-inflammatory agents. In some embodiments, the PSMA binding proteins or a multispecific binding protein comprising a PSMA binding protein as described herein are administered before, during, or after surgery. According to another embodiment of the invention, kits for detecting prostate cancer for diagnosis, prognosis or monitoring are provided. The kits include the foregoing PSMA binding proteins (e.g., labeled anti-PSMA single domain antibodies or antigen binding fragments thereof), and one or more compounds for detecting the label. In some embodiments, the label is selected from the group consisting of a fluorescent label, an enzyme label, a radioactive label, a nuclear magnetic resonance active label, a luminescent label, and a chromophore label.

A further embodiment provides one or more of the above described binding proteins, such as anti-PSMA single domain antibodies or antigen-binding fragments thereof packaged in lyophilized form, or packaged in an aqueous medium. In another aspect of the disclosure, methods for detecting the presence of PSMA, or a cell expressing PSMA, in a sample are provided. Such methods include contacting the sample with any of the foregoing PSMA binding proteins (such as anti-PSMA single domain antibodies or antigen-binding fragments thereof) which specifically bind to an extracellular domain of PSMA, for a time sufficient to allow the formation of a complex between the antibody or antigen-binding fragment thereof and PSMA, and detecting the PSMA-antibody complex or PSMA-antigen-binding fragment complex. In some embodiments, the presence of a complex in the sample is indicative of the presence in the sample of PSMA or a cell expressing PSMA. In another aspect, the disclosure provides other methods for diagnosing a PSMA-mediated disease in a subject. Such methods include administering to a subject suspected of having or previously diagnosed with PSMA-mediated disease an amount of any of the foregoing PSMA binding proteins (such as anti-PSMA single domain antibodies or antigen-binding fragments thereof) which specifically bind to an extracellular domain of prostate specific membrane antigen. The method also includes allowing the formation of a complex between the antibody or antigen-binding fragment thereof and PSMA, and detecting the formation of the PSMA-antibody complex or PSMA-antigen-binding fragment antibody complex to the target epitope. The presence of a complex in the subject suspected of having or previously diagnosed with prostate cancer is indicative of the presence of a PSMA-mediated disease.

In certain embodiments of the methods, the PSMA-mediated disease is prostate cancer. In other embodiments, the PSMA-mediated disease is a non-prostate cancer, such as those selected from the group consisting of bladder cancer including transitional cell carcinoma; pancreatic cancer including pancreatic duct carcinoma; lung cancer including non-small cell lung carcinoma; kidney cancer including conventional renal cell carcinoma; sarcoma including soft tissue sarcoma; breast cancer including breast carcinoma; brain cancer including glioblastoma multiforme; neuroendocrine carcinoma; colon cancer including colonic carcinoma; testicular cancer including testicular embryonal carcinoma; and melanoma including malignant melanoma.

In some embodiments of the foregoing methods, the PSMA binding proteins (such as anti-PSMA single domain antibodies or antigen-binding fragments thereof is labeled. In other embodiments of the foregoing methods, a second antibody is administered to detect the first antibody or antigen-binding fragment thereof. In a further aspect of the disclosure, methods for assessing the prognosis of a subject with a PSMA-mediated disease are provided. Such methods include administering to a subject suspected of having or previously diagnosed with PSMA-mediated disease an effective amount of any of the foregoing PSMA binding proteins (such as anti-PSMA single domain antibodies or antigen-binding fragments thereof, allowing the formation of a complex between the antibody or antigen-binding fragment thereof and PSMA, and detecting the formation of the complex to the target epitope. The amount of the complex in the subject suspected of having or previously diagnosed with PSMA-mediated disease is indicative of the prognosis.

In another aspect of the disclosure, methods for assessing the effectiveness of a treatment of a subject with a PSMA-mediated disease are provided. Such methods include administering to a subject of having or previously diagnosed with PSMA-mediated disease an effective amount of any of the foregoing PSMA binding proteins, such as anti-PSMA single domain antibodies or antigen-binding fragments thereof, allowing the formation of a complex between the antibody or antigen-binding fragment thereof and PSMA, and detecting the formation of the complex to the target epitope. The amount of the complex in the subject suspected of having or previously diagnosed with PSMA-mediated disease is indicative of the effectiveness of the treatment. In certain embodiments, the PSMA-mediated disease is prostate cancer. In other embodiments, the PSMA-mediated disease is a non-prostate cancer. In those embodiments, the non-prostate cancer preferably is selected from the group consisting of bladder cancer including transitional cell carcinoma; pancreatic cancer including pancreatic duct carcinoma; lung cancer including non-small cell lung carcinoma; kidney cancer including conventional renal cell carcinoma; sarcoma including soft tissue sarcoma; breast cancer including breast carcinoma; brain cancer including glioblastoma multiforme; neuroendocrine carcinoma; colon cancer including colonic carcinoma; testicular cancer including testicular embryonal carcinoma; and melanoma including malignant melanoma. In still other embodiments, the antibody or antigen-binding fragment thereof is labeled. In further embodiments, a second antibody is administered to detect the first antibody or antigen-binding fragment thereof.

According to yet another aspect of the disclosure, methods for inhibiting the growth of a cell expressing PSMA are provided. Such methods include contacting a cell expressing PSMA with an amount of at least one of the foregoing antibodies or antigen-binding fragments thereof which specifically binds to an extracellular domain of PSMA effective to inhibit the growth of the cell expressing PSMA.

EXAMPLES

The examples below further illustrate the described embodiments without limiting the scope of the invention.

Example 1: Generation of Anti-PSMA Single Domain Antibody Variants with Equivalent or Improved Binding Properties to a Parental Anti-PSMA Single Domain Antibody Characterization of Parental Anti-PSMA Phage
Specific binding of the parental anti-PSMA phage to an PSMA antigen was determined, (Table 1)
Single Substitution PSMA sdAb Phage Libraries Selected on Cyno PSMA
A single substitution library was provided for each of the three CDR domains. Single substitution libraries were bound to cynomolgus PSMA and then washed in buffer for 30 minutes. Phages bound at 0 and 30 minutes were rescued and counted. Phages selected using a 30 minute wash in the buffer were used to create two independent combinatorial phage libraries.
Combinatorial Anti PSMA Libraries
Cynomolgus PSMA was used as the selection target for three rounds of selection. Wells were washed for 2 to 4 hours after combinatorial phage binding from two independent libraries for three rounds of selection. Inserts PCRed from the third round of selection were subcloned into the p34 expression vector. 96 clones were picked, DNA was purified, sequenced, and transfected into Expi293 cells.
Single Substitution PSMA sdAb Phage Libraries Selected on huPSMA
A single substitution library was provided for each of the three CDR domains. Single substitution libraries were bound to human PSMA and then washed in buffer containing 30 µg/ml h PSMA-Fc for 24 hours. Phages bound at 0 and 24 hours were rescued and counted. Phages selected using the 24 hour competitive wash were used to create a combinatorial phage library.
Combinatorial Anti PSMA Libraries
Human PSMA was used as the selection target for three rounds of selection. Wells were washed in buffer containing 30 µg/ml-850 µg/ml human PSMA-Fc for 24-96 hours after combinatorial phage binding for three rounds of selection. Inserts PCRed from the third round of selection were subcloned into the p34 expression vector. 96 clones were picked, DNA was purified, sequenced, and transfected into Expi293 cells.
Binding Affinity Measurement
Supernatants were used to estimate Kd, kon, and koff (or kdis) to human and cynomolgus PSMA using the OCTET® system. Several clones were selected for further characterization (Table 1), based on their binding affinities, and association and dissociation rate constants for interaction with human PSMA, compared to the parental sdAb as well as robust production, aggregation and stability profiles. The parental sdAb is listed as Anti-PSMA wt sdAb.6his in Table 1.

TABLE 1

Binding Affinity (Kd) of several PSMA binding proteins to human PSMA

|  | Kd (hFc•flag•hPSMA) | kon (1/Ms) | kdis (1/s) |
|---|---|---|---|
| Anti-PSMA wt sdAb.6his | 15.0 nM | 8.77E+05 | 1.32E-02 |
| anti-PSMA E31P sdAb.6his | 9.5 nM | 3.83E+05 | 3.66E-03 |
| anti-PSMA T56Q sdAb.6his | 5.6 nM | 8.22E+05 | 4.61E-03 |
| anti-PSMA G55K sdAb.6his | 4.5 nM | 5.56E+05 | 2.48E-03 |
| anti-PSMA S33H T50D G97SsdAb.6his | 6.7 nM | 8.00E+05 | 5.38E-03 |
| anti-PSMA S33H G97SsdAb.6his | 0.21 nM | 9.36E+05 | 1.97E-05 |

Example 2: Methods to Assess Binding and Cytotoxic Activities of an Exemplary PSMA Targeting Trispecific Antigen-Binding Molecules Protein Production Sequences of trispecific molecules were cloned into mammalian expression vector pcDNA 3.4 (Invitrogen) preceded by a leader sequence and followed by a 6× Histidine Tag (SEQ ID NO: 33). Expi293F cells (Life Technologies A14527) were maintained in suspension in Optimum Growth Flasks (Thomson) between 0.2 to 8×1e6 cells/ml in Expi293 media. Purified plasmid DNA was transfected into Expi293 cells in accordance with Expi293 Expression System Kit (Life Technologies, A14635) protocols, and maintained for 4-6 days post transfection. Conditioned media was partially purified by affinity and desalting chromatography. Trispecific proteins were subsequently polished by ion exchange or, alternatively, concentrated with AMICON™ Ultra centrifugal filtration units (EMD Millipore), applied to SUPERDEX™ 200 size exclusion media (GE Healthcare) and resolved in a neutral buffer containing excipients. Fraction pooling and final purity were assessed by SDS-PAGE and analytical SEC.

Affinity Measurements

The affinities of the all binding domains molecules were measured by biolayer inferometry using an Octet instrument.

PSMA affinities were measured by loading human PSMA-Fc protein (100 nM) onto anti-human IgG Fc biosensors for 120 seconds, followed by a 60 second baseline, after which associations were measured by incubating the sensor tip in a dilution series of the trispecific molecules for 180 seconds, followed by dissociation for 50 seconds. EGFR and CD3 affinities were measured by loading human EGFR-Fc protein or human CD3-Flag-Fc protein, respectively, (100 nM) onto anti-human IgG Fc biosensors for 120 seconds, followed by a 60 second baseline, after which associations were measured by incubating the sensor tip in a dilution series of the trispecific molecules for 180 seconds, followed by dissociation for 300 seconds. Affinities to human serum albumin (HSA) were measured by loading biotinylated albumin onto streptavidin biosensors, then following the same kinetic parameters as for CD3 affinity measurements. All steps were performed at 30° C. in 0.25% casein in phosphate-buffered saline.

Cytotoxicity Assays

A human T-cell dependent cellular cytotoxicity (TDCC) assay was used to measure the ability of T cell engagers, including trispecific molecules, to direct T cells to kill tumor cells (Nazarian et al. 2015. J Biomol Screen. 20:519-27). In this assay, T cells and target cancer cell line cells are mixed together at a 10:1 ratio in a 384 wells plate, and varying amounts of T cell engager are added. After 48 hours, the T cells are washed away leaving attached to the plate target cells that were not killed by the T cells. To quantitate the remaining viable cells, CELLTITER-GLO® Luminescent Cell Viability Assay (Promega) is used. In some cases, the target cells are engineered to express luciferase. In these cases, viability of the target cells is assessed by performing a luminescent luciferase assay with STEADYGLO® reagent (Promega), where viability is directly proportional to the amount of luciferase activity.

Stability Assays

The stability of the trispecific binding proteins was assessed at low concentrations in the presence of non-human primate serum. TRITAC™ molecules were diluted to 33 µg/ml in Cynomolgus serum (BioReclamationIVT) and either incubated for 2 d at 37° C. or subjected to five freeze/thaw cycles. Following the treatment, the samples were assessed in cytotoxicity (TDCC) assays and their remaining activity was compared to untreated stock solutions.

Xenograft Assays

The in vivo efficacy of trispecific binding proteins was assessed in xenograft experiments (Crown Bioscience, Taicang). NOD/SCID mice deficient in the common gamma chain (NCG, Model Animal Research Center of Nanjing University) were inoculated on day 0 with a mixture of 5e6 22Rv1 human prostate cancer cells and 5e6 resting, human T cells that were isolated from a healthy, human donor. The mice were randomized into three groups, and treated with vehicle, 0.5 mg/kg PSMA TRITAC™ C324 or 0.5 mg/kg PSMA BiTE. Treatments were administered daily for 10 days via i.v. bolus injection. Animals were checked daily for morbidity and mortality. Tumor volumes were determined twice weekly with a caliper. The study was terminated after 30 days.

PK Assays

The purpose of this study was to evaluate the single dose pharmacokinetics of trispecific binding proteins following intravenous injection. 2 experimentally naïve cynomolgus monkeys per group (1 male and 1 female) were given compound via a slow IV bolus injection administered over approximately 1 minute. Following dose administration, cage side observations were performed once daily and body weights were recorded weekly. Blood samples were collected and processed to serum for pharmacokinetic analysis through 21 days post dose administration.

Concentrations of test articles were determined from monkey serum with an electroluminescent readout (Meso Scale Diagnostics, Rockville). 96 well plates with immobilized, recombinant CD3 were used to capture the analyte. Detection was performed with sulfo-tagged, recombinant PSMA on a MSD reader according to the manufacturer's instructions.

Figure 2A:
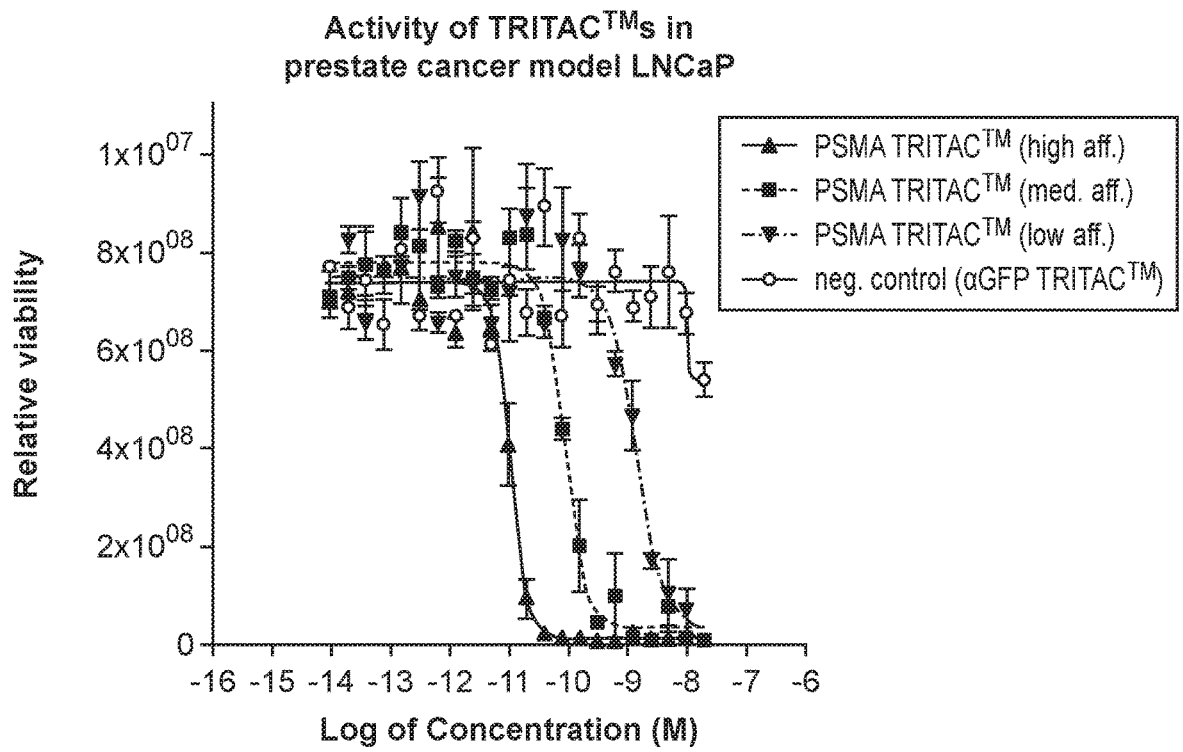
FIGS. 2A-B compare the ability of exemplary PSMA targeting trispecific proteins (PSMA targeting TRITAC™ molecules) with different affinities for CD3 to induce T cells to kill human prostate cancer cells.
Figure 2B:
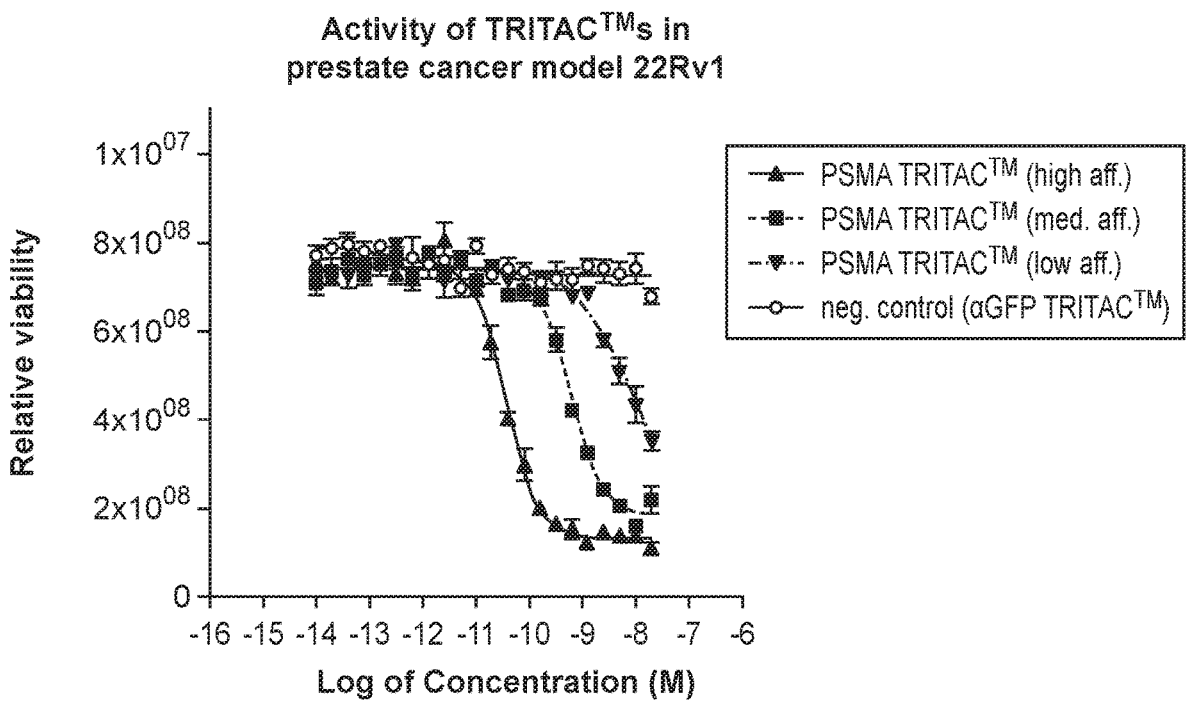
Figure 3:
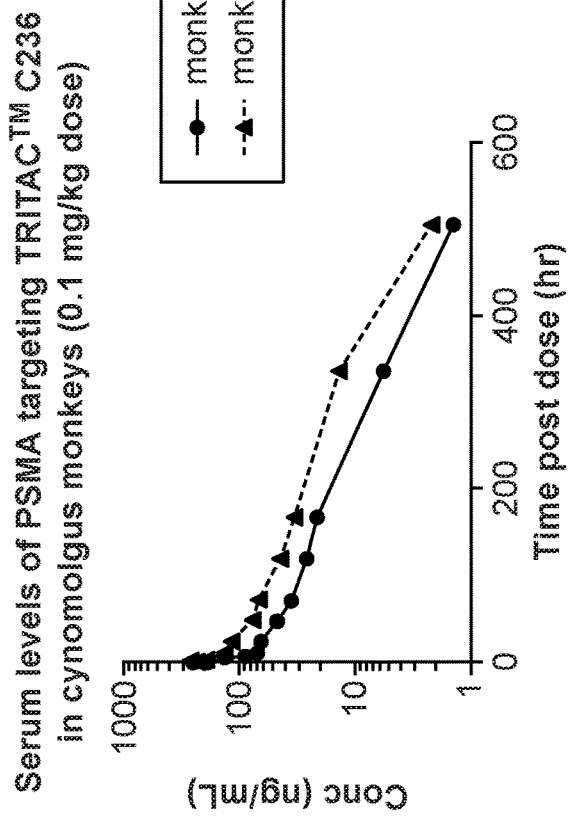
FIG. 3 shows the serum concentration of PSMA targeting TRITAC™ C236 in Cynomolgus monkeys after i.v. administration (100 μg/kg) over three weeks.
Figure 4:
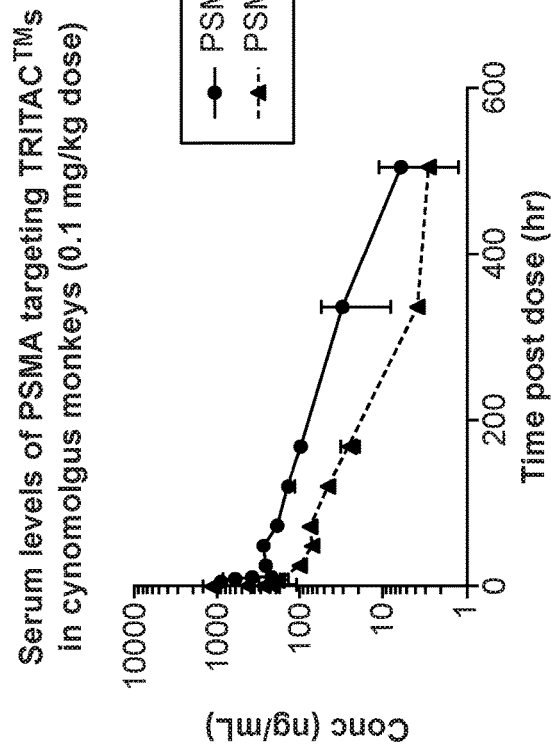
FIG. 4 shows the serum concentration of PSMA targeting TRITAC™ molecules with different CD3 affinities in Cynomolgus monkeys after i.v. administration (100 μg/kg) over three weeks.
Figure 6:
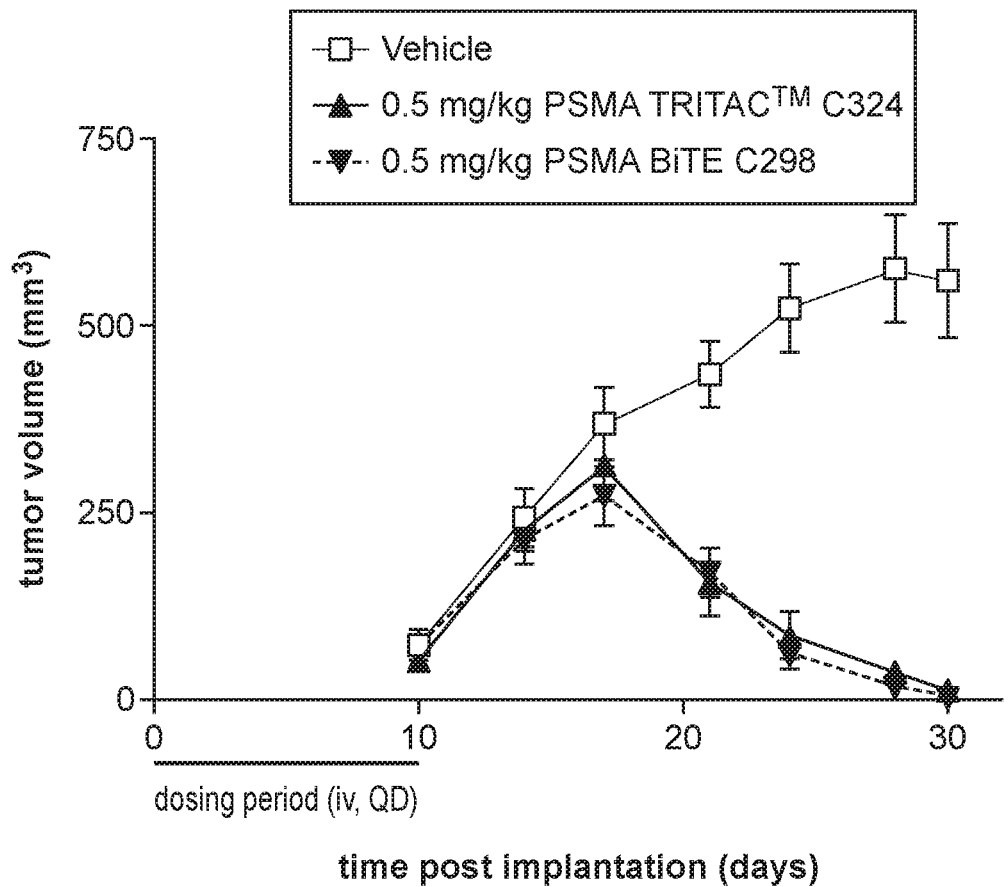
FIG. 6 demonstrates the ability of PSMA targeting TRITAC™ molecules to inhibit tumor growth of human prostate cancer cells in a mouse xenograft experiment.

Example 3: Assessing the Impact of CD3 Affinity on the Properties of Exemplary PSMA Targeting Trispecific Molecules PSMA targeting trispecific molecules with distinct CD3 binding domains were studied to demonstrate the effects of altering CD3 affinity. An exemplary PSMA targeting trispecific molecule is illustrated in FIG. 1. Table 2 lists the affinity of each molecule for the three binding partners (PSMA, CD3, HSA). Affinities were measured by biolayer interferometry using an Octet instrument (Pall Forte Bio). Reduced CD3 affinity leads to a loss in potency in terms of T cell mediated cellular toxicity (FIGS. 2A-C). The pharmacokinetic properties of these trispecific molecules were assessed in cynomolgus monkeys. Molecules with high affinity for CD3 like TRITAC™ C236 have a terminal half-life of approx. 90 h (FIG. 3). Despite the altered ability to bind CD3 on T cells, the terminal half-life of two molecules with different CD3 affinities shown in FIG. 4 is very similar. However, the reduced CD3 affinity appears to lead to a larger volume of distribution, which is consistent with reduced sequestration of trispecific molecule by T cells. There were no adverse clinical observations or body weight changes noted during the study period.

experiment, the trispecific molecule was able to inhibit tumor growth with an efficacy comparable to a BiTE molecule (FIG. 6).

Example 6: Specificity of Exemplary PSMA Targeting Trispecific Molecules

Figures 7A, 7B:
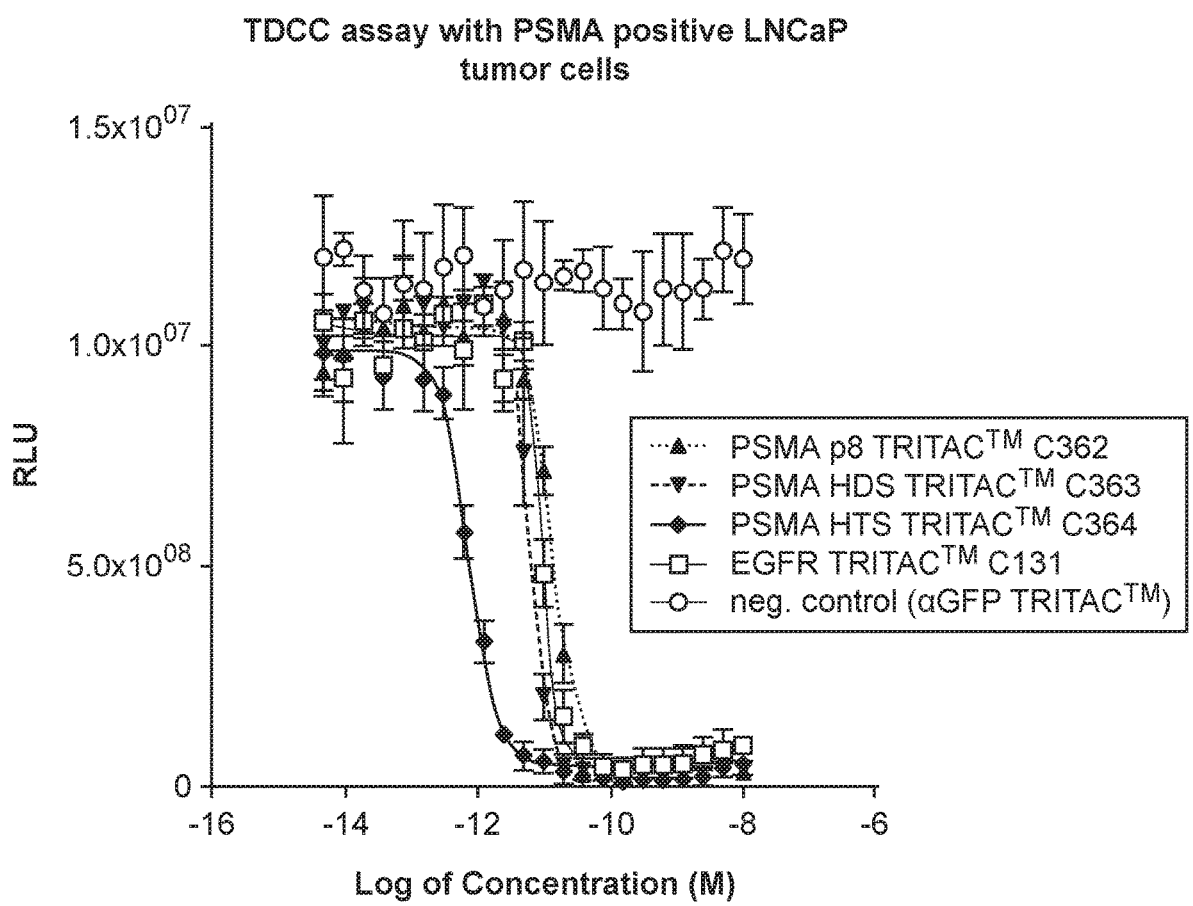
FIGS. 7A-D illustrates the specificity of TRITAC™ molecules in cell killing assays with target cell lines that do or do not express the target protein.

In order to assess the specificity of PSMA targeting TRITAC™ molecules, their ability to induce T cells to kill tumor cells was tested with tumor cells that are negative for PSMA (FIG. 7A). An EGFR targeting TRITAC™ molecule

TABLE 2

Binding Affinities for Human and Cynomolgus Antigens

| | anti-PSMA KD value (nM) | | | anti-Albumin KD value (nM) | | | anti-CD3e $K_D$ value (nM) | | |
|---|---|---|---|---|---|---|---|---|---|
| | human | cyno | ratio cyno/hum | pHSA | CSA | ratio cyno/hum | human | cyno | ratio cyno/hum |
| Tool TriTAC high aff. - C236 | 16.3 | 0 | 0 | 22.7 | 25.4 | 1.1 | 6.0 | 4.7 | 0.8 |
| TriTAC CD3 high aff. - C324 | 17.9 | 0 | 0 | 9.8 | 9.7 | 1 | 7.4 | 5.8 | 0.8 |
| TriTAC CD3 med aff. - C339 | 13.6 | 0 | 0 | 8.8 | 8.3 | 0.9 | 40.6 | 33.6 | 0.8 |
| TriTAC CD3 low aff - C325 | 15.3 | 0 | 0 | 10.1 | 9.7 | 1 | 217 | 160 | 0.7 |

Figure 5A:
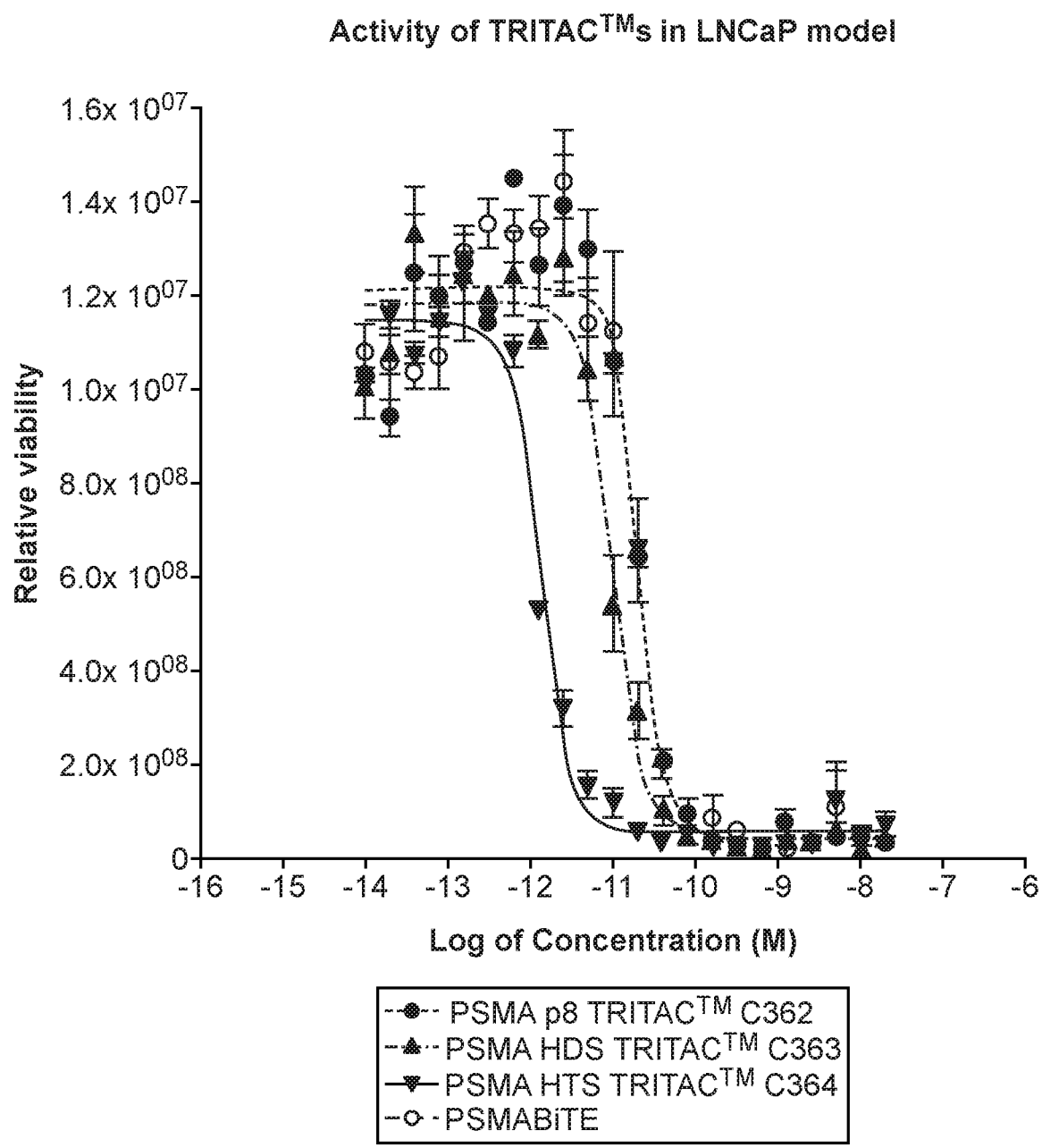
Figure 5B:
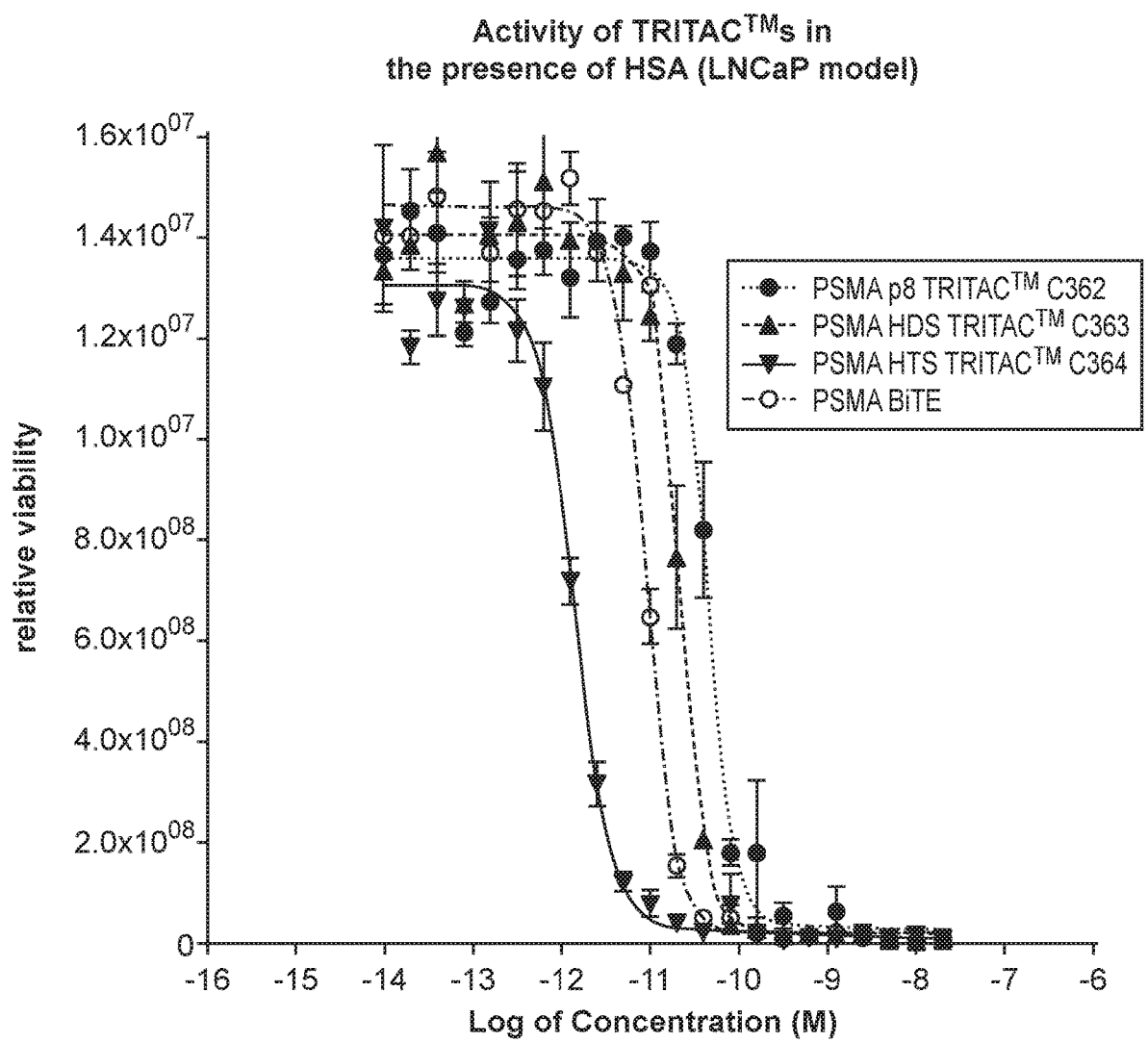
Figures 7C, 7D:
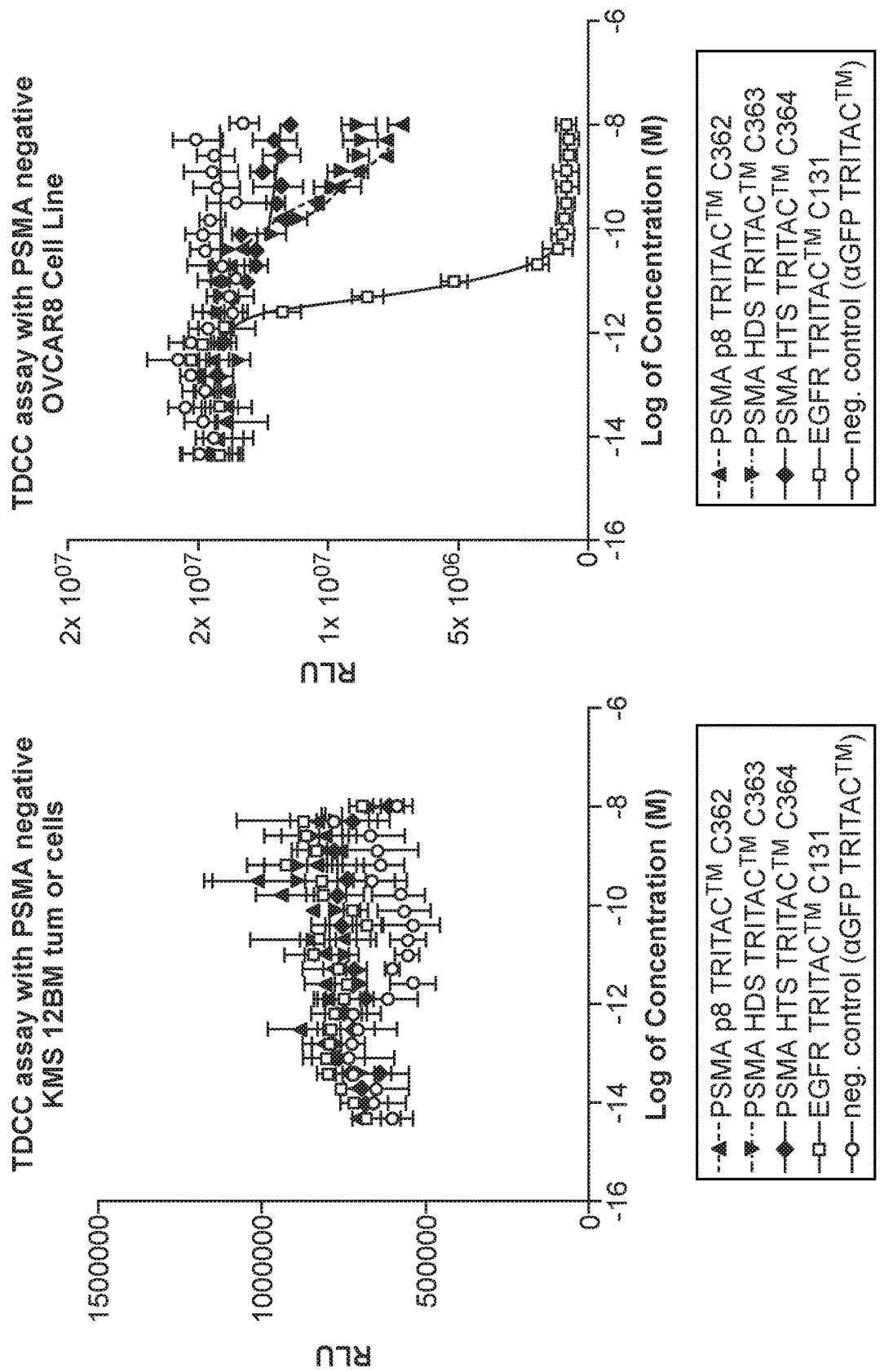
Figure 8A:
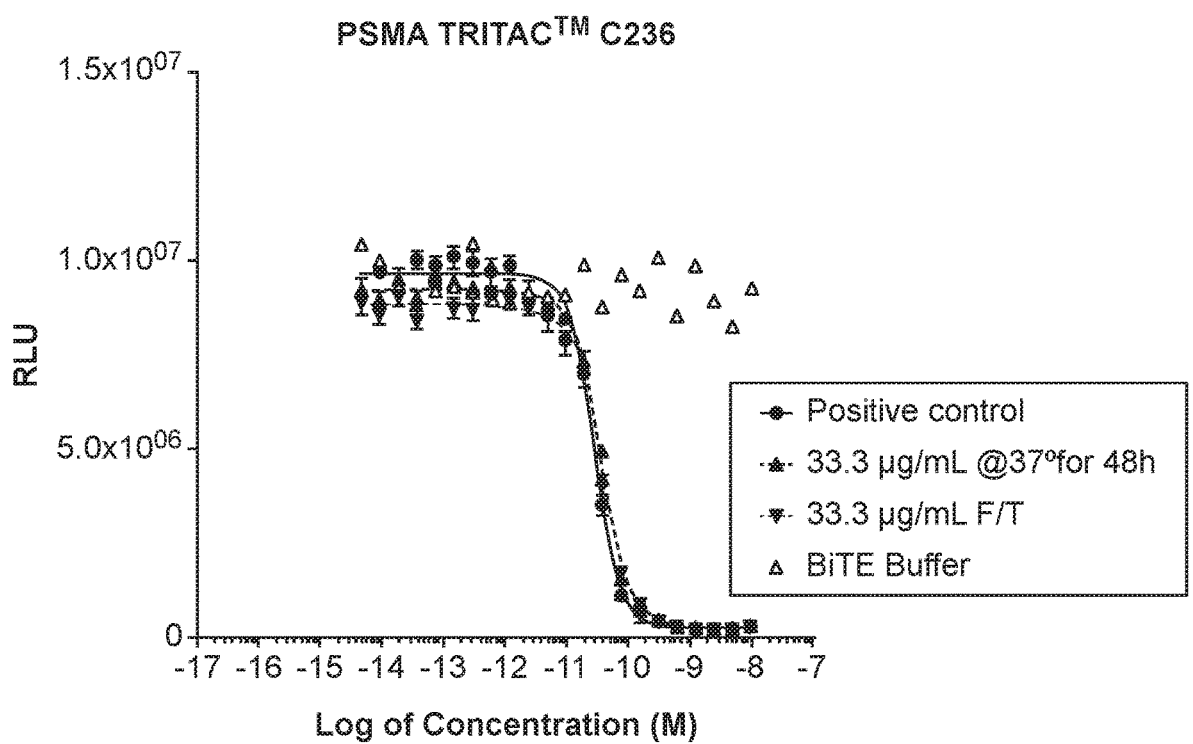
FIGS. 8A-D depict the impact of pre-incubation at 37° C. and freeze/thaw cycles on TRITAC™ activity.
Figure 8B:
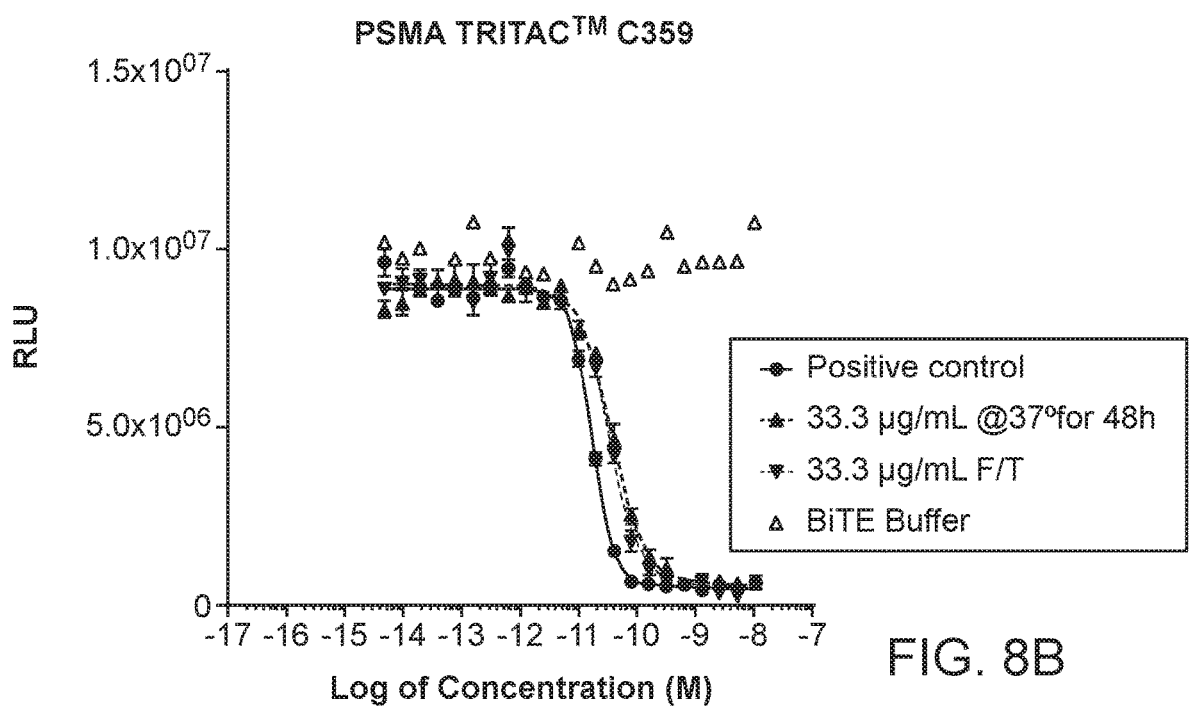
Figure 8C:
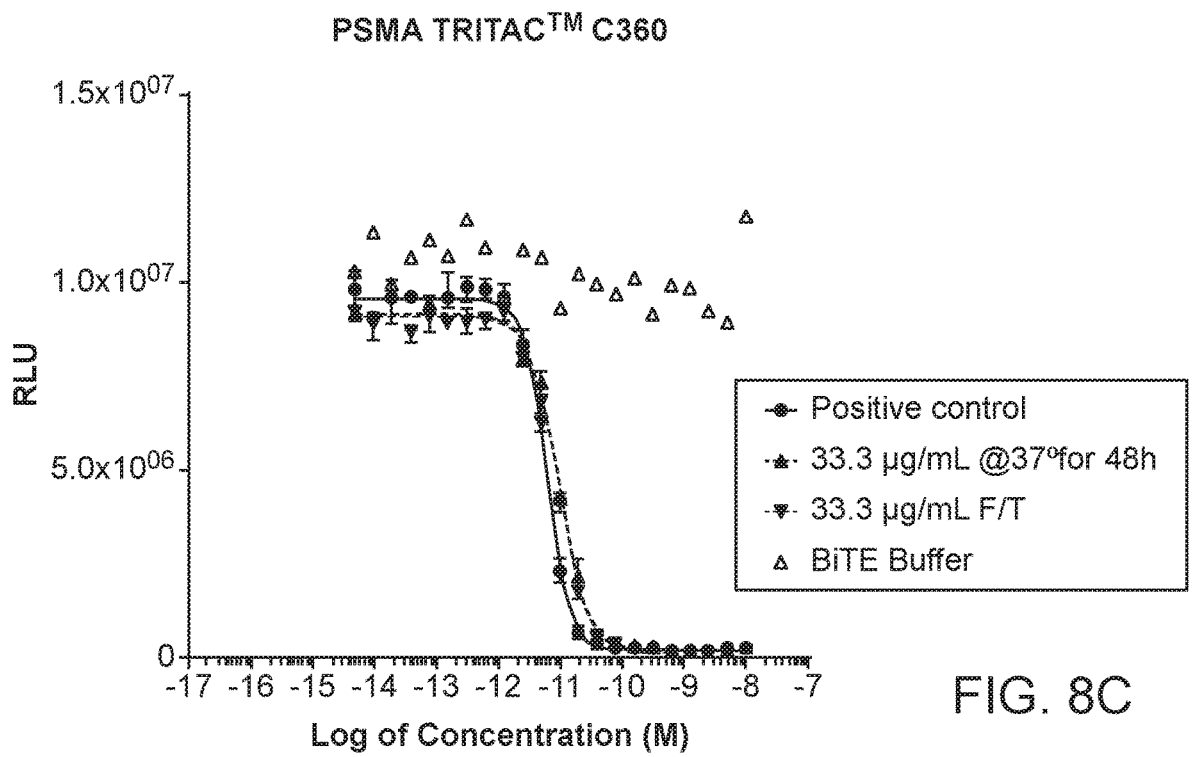
Figure 8D:
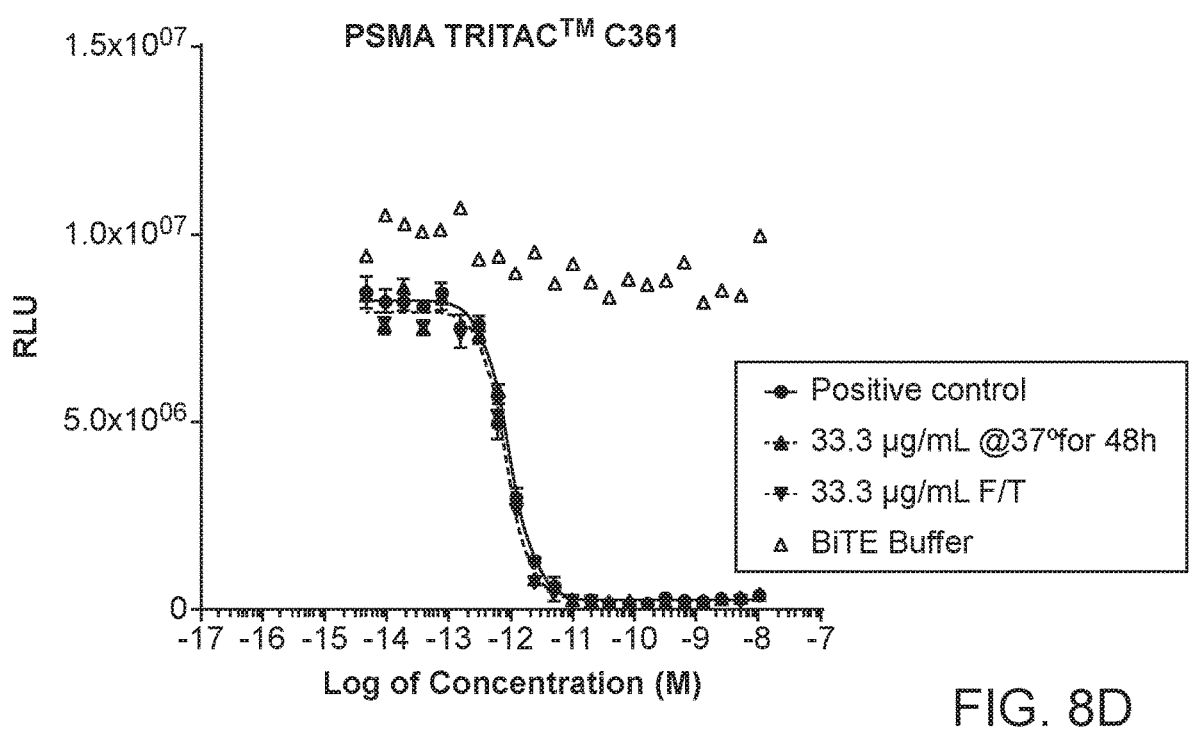

Example 4: Assessing the Impact of PSMA Affinity on the Properties of Exemplary PSMA Targeting Trispecific Molecules PSMA targeting trispecific molecules with distinct PSMA binding domains were studied to demonstrate the effects of altering PSMA affinity. Table 3 lists the affinity of each molecule for the three binding partners (PSMA, CD3, HSA). Reduced PSMA affinity leads to a loss in potency in terms of T cell mediated cellular toxicity (FIGS. 5A-C).

served as positive control, a GFP targeting TRITAC™ molecule as negative control. All three TRITAC™ molecules with distinct PSMA binding domains showed the expected activity against the PSMA positive cell line LNCaP (FIG. 7B), but did not reach EC50s in the PSMA negative tumor cell lines KMS12BM and OVCAR8 (FIGS. 7C and 7D). The EC50s are summarized in Table 4. At very high TRITAC™ concentrations (>1 nM), some limited off-target cell killing could be observed for TRITAC™ molecules

TABLE 3

Binding Affinities for Human and Cynomolgus Antigens

| | anti-PSMA KD value (nM) | | | anti-Albumin KD value (nM) | | | anti-CD3e $K_D$ value (nM) | | |
|---|---|---|---|---|---|---|---|---|---|
| | human | cyno | ratio cyno/hum | pHSA | CSA | ratio cyno/hum | human | cyno | ratio cyno/hum |
| PSMA-TriTAC (p8)-C362 | 22.0 | 0 | n/a | 6.6 | 6.6 | 1.0 | 8.3 | 4.3 | 0.52 |
| PSMA TriTAC (HDS)-C363 | 3.7 | 540 | 146 | 7.6 | 8.4 | 1.1 | 8.0 | 5.2 | 0.65 |
| PSMA TriTAC (HTS)-C364 | 0.15 | 663 | 4423 | 8.4 | 8.6 | 1.0 | 7.7 | 3.8 | 0.49 |

Example 5: In Vivo Efficacy of Exemplary PSMA Targeting Trispecific Molecules

The PSMA targeting trispecific molecule C324 was assessed for its ability to inhibit the growth of tumors in mice. For this experiment, immunocompromised mice reconstituted with human T cells were subcutaneously inoculated with PSMA expressing human prostate tumor cells (22Rv1) and treated daily for 10 days with 0.5 mg/kg i.v. of either PSMA targeting BiTE or TRITAC™ molecules. Tumor growth was measured for 30. Over the course of the C362 and C363, while C364 did not show significant cell killing under any of the tested conditions.

TABLE 4

Cell killing activity of TRITAC ™ molecules in with antigen positive and negative tumor cell lines (EC50 [pM])

| TRITAC ™ | LNCaP | KMS12BM | OVCAR8 |
|---|---|---|---|
| PSMA p8 TRITAC ™ C362 | 13.0 | >10,000 | >10,000 |
| PSMA HDS TRITAC ™ C363 | 6.2 | >10,000 | >10,000 |
| PSMA HTS TRITAC ™ C364 | 0.8 | >10,000 | >10,000 |

TABLE 4-continued

Cell killing activity of TRITAC ™ molecules in with antigen positive and negative tumor cell lines (EC50 [pM])

| TRITAC ™ | LNCaP | KMS12BM | OVCAR8 |
|---|---|---|---|
| EGFR TRITAC ™ C131 | 9.4 | >10,000 | 6 |
| GFP TRITAC ™ C | >10,000 | >10,000 | >10,000 |

Example 7: Stress Tests and Protein Stability

Four PSMA targeting trispecific molecules were either incubated for 48 h in Cynomolgus serum at low concentrations (33.3 μg/ml) or subjected to five freeze thaw cycles in Cynomolgus serum. After the treatment, the bio-activity of the TRITAC™ molecules was assessed in cell killing assays and compared to unstressed samples ("positive control", FIG. 8A-D). All molecules maintained the majority of their cell killing activity. TRITAC™ C362 was the most stress resistant and did not appear to lose any activity under the conditions tested here.

Example 8: Xenograft Tumor Model

The PSMA targeting trispecific proteins of the previous examples are evaluated in a xenograft model.

Male immune-deficient NCG mice are subcutaneously inoculated with $5 \times 10^6$ 22Rv1 cells into their right dorsal flank. When tumors reach 100 to 200 mm$^3$, animals are allocated into 3 treatment groups. Groups 2 and 3 (8 animals each) are intraperitoneally injected with $1.5 \times 10^7$ activated human T-cells. Three days later, animals from Group 3 are subsequently treated with a total of 9 intravenous doses of 50 μg of the exemplary PSMA trispecific antigen-binding protein (qdx9d). Groups 1 and 2 are only treated with vehicle. Body weight and tumor volume are determined for 30 days. It is expected that tumor growth in mice treated with the PSMA trispecific antigen-binding protein is significantly reduced in comparison to the tumor growth in respective vehicle-treated control group.

Example 9: Proof-of-Concept Clinical Trial Protocol for Administration of the Exemplary PSMA Trispecific Antigen-Binding Protein to Prostate Cancer Patients This is a Phase I/II clinical trial for studying the PSMA trispecific antigen-binding protein of Example 1 as a treatment for Prostate Cancer.

Study Outcomes:

Primary: Maximum tolerated dose of PSMA targeting trispecific proteins of the previous examples Secondary: To determine whether in vitro response of PSMA targeting trispecific proteins of is the previous examples are associated with clinical response Phase I The maximum tolerated dose (MTD) will be determined in the phase I section of the trial.

1.1 The maximum tolerated dose (MTD) will be determined in the phase I section of the trial.
1.2 Patients who fulfill eligibility criteria will be entered into the trial to PSMA targeting trispecific proteins of the previous examples.
1.3 The goal is to identify the highest dose of PSMA targeting trispecific proteins of the previous examples that can be administered safely without severe or unmanageable side effects in participants. The dose given will depend on the number of participants who have been enrolled in the study prior and how well the dose was tolerated. Not all participants will receive the same dose.

Phase II 2.1 A subsequent phase II section will be treated at the MTD with a goal of determining if therapy with therapy of PSMA targeting trispecific proteins of the previous examples results in at least a 20% response rate.

Primary Outcome for the Phase II—To determine if therapy of PSMA targeting trispecific proteins of the previous examples results in at least 20% of patients achieving a clinical response (blast response, minor response, partial response, or complete response)

Eligibility:

Histologically confirmed newly diagnosed aggressive prostate cancer according to the current World Health Organisation Classification, from 2001 to 2007

Any stage of disease.

Treatment with docetaxel and prednisone (+/−surgery).

Age ≥18 years

Karnofsky performance status ≥50% or ECOG performance status 0-2

Life expectancy ≥6 weeks

Example 10: Activity of an Exemplary PSMA Antigen-Binding Protein (PSMA Targeting TRITAC™ Molecule) in Redirected T Cell Killing Assays Using a Panel of PSMA Expressing Cell Lines and T Cells from Different Donors This study was carried out to demonstrate that the activity of the exemplary PSMA trispecific antigen-binding protein is not limited to LNCaP cells or a single cell donor.

Redirected T cell killing assays were performed using T cells from four different donors and the human PSMA-expressing prostate cancer cell lines VCaP, LNCaP, MDAPCa2b, and 22Rv1. With one exception, the PSMA trispecific antigen-binding protein was able to direct killing of these cancer cell lines using T cells from all donors with $EC_{50}$ values of 0.2 to 1.5 pM, as shown in Table 5. With the prostate cancer cell line 22 Rv1 and Donor 24, little to no killing was observed (data not shown). Donor 24 also only resulted approximately 50% killing of the MDAPCa2b cell line whereas T cells from the other 3 donors resulted in almost complete killing of this cell line (data not shown). Control assays demonstrated that killing by the PSMA trispecific antigen-binding protein was PSMA specific. No killing was observed when PSMA-expressing cells were treated with a control trispecific protein targeting green fluorescent protein (GFP) instead of PSMA (data not shown). Similarly, the PSMA trispecific antigen-binding protein was inactive with cell lines that lack PSMA expression, NCI-1563 and HCT116, also shown in Table 5.

TABLE 5

$EC_{50}$ Values from TDCC Assays with Six Human Cancer Cell Lines and Four Different T Cell Donors

| | TDCC $EC_{50}$ Values (M) | | | |
|---|---|---|---|---|
| Cell Line | Donor 24 | Donor 8144 | Donor 72 | Donor 41 |
| LNCaP | 1.5E−12 | 2.2E−13 | 3.6E−13 | 4.3E−13 |
| MDAPCa2b | 4.8E−12 | 4.1E−13 | 4.9E−13 | 6.5E−13 |

TABLE 5-continued

EC$_{50}$ Values from TDCC Assays with Six Human Cancer Cell Lines and Four Different T Cell Donors

| Cell Line | TDCC EC$_{50}$ Values (M) | | | |
|---|---|---|---|---|
| | Donor 24 | Donor 8144 | Donor 72 | Donor 41 |
| VCaP | 6.4E−13 | 1.6E−13 | 2.0E−13 | 3.5E−13 |
| 22Rv1 | n/a | 7.2E−13 | 1.4E−12 | 1.3E−12 |
| HCT116 | >1.0E−8 | >1.0E−8 | >1.0E−8 | >1.0E−8 |
| NCI-1563 | >1.0E−8 | >1.0E−8 | >1.0E−8 | >1.0E−8 |

Example 11: Stimulation of Cytokine Expression in by an Exemplary PSMA Trispecific Antigen-Binding Protein (PSMA Targeting TRITAC™ Molecule) in Redirected T Cell Killing Assays This study was carried out to demonstrate activation of T cells by the exemplary PSMA trispecific antigen-binding protein during redirected T cell killing assays by measuring secretion of cytokine into the assay medium by activated T cells.

Conditioned media collected from redirected T cell killing assays, as described above in Example 9, were analyzed for expression of the cytokines TNFα and IFNγ. Cytokines were measured using AlphaLISA assays (Perkin-Elmer). Adding a titration of the PSMA antigen-binding protein to T cells from four different donors and four PSMA-expressing cell lines, LNCaP, VCaP, MDAPCa2b, and 22Rv1 resulted in increased levels of TNFα. The results for TNFα expression and IFN γ expression levels in the conditioned media are shown in Tables 6 and 7, respectively. The EC$_{50}$ values for the PSMA antigen-binding protein induced expression of these cytokines ranged from 3 to 15 pM. Increased cytokine levels were not observed with a control trispecific protein targeting GFP. Similarly, when assays were performed with two cell lines that lack PSMA expression, HCT116 and NCI-H1563, PSMA HTS TRITAC™ also did not increase TNFα or IFNγ expression.

TABLE 6

EC$_{50}$ Values for TNFα Expression in Media from PSMA Trispecific Antigen-Binding Protein TDCC Assays with Six Human Cancer Cell Lines and T Cells from Four Different Donors

| Cell Line | Donor 24 | Donor 8144 | Donor 41 | Donor72 |
|---|---|---|---|---|
| LNCaP | 4.9E−12 | 2.8E−12 | 4.0E−12 | 3.2E−12 |
| VCaP | 3.2E−12 | 2.9E−12 | 2.9E−12 | 2.9E−12 |
| MDAPCa2b | 2.1E−11 | 4.0E−12 | 5.5E−12 | 3.6E−12 |
| 22Rv1 | 8.9E−12 | 2.5E−12 | 4.0E−12 | 3.3E−12 |
| HCT116 | >1E−8 | >1E−8 | >1E−8 | >1E−8 |
| NCI-H1563 | >1E−8 | >1E−8 | >1E−8 | >1E−8 |

TABLE 7

EC$_{50}$ Values for IFNγ Expression in Media from PSMA Trispecific Antigen-Binding Protein TDCC Assays with Six Human Cancer Cell Lines and T Cells from Four Different Donors

| Cell Line | Donor 24 | Donor 8144 | Donor 41 | Donor72 |
|---|---|---|---|---|
| LNCaP | 4.2E−12 | 4.2E−12 | 4.2E−12 | 2.8E−12 |
| VCaP | 5.1E−12 | 1.5E−11 | 3.4E−12 | 4.9E−12 |
| MDAPCa2b | 1.5E−11 | 5.8E−12 | 9.7E−12 | 3.5E−12 |
| 22Rv1 | 7.8E−12 | 3.0E−12 | 9.1E−12 | 3.0E−12 |

TABLE 7-continued

EC$_{50}$ Values for IFNγ Expression in Media from PSMA Trispecific Antigen-Binding Protein TDCC Assays with Six Human Cancer Cell Lines and T Cells from Four Different Donors

| Cell Line | Donor 24 | Donor 8144 | Donor 41 | Donor72 |
|---|---|---|---|---|
| HCT116 | >1E−8 | >1E−8 | >1E−8 | >1E−8 |
| NCI-H1563 | >1E−8 | >1E−8 | >1E−8 | >1E−8 |

Example 12: Activity of an Exemplary PSMA Trispecific Antigen-Binding Protein (PSMA Targeting TRITAC™) in Redirected T Cell Killing Assay (TDCC) Using T Cells from Cynomolgus Monkeys This study was carried out to test the ability of the exemplary PSMA trispecific antigen-binding protein to direct T cells from cynomolgus monkeys to kill PSMA-expressing cell lines.

Figure 9A:
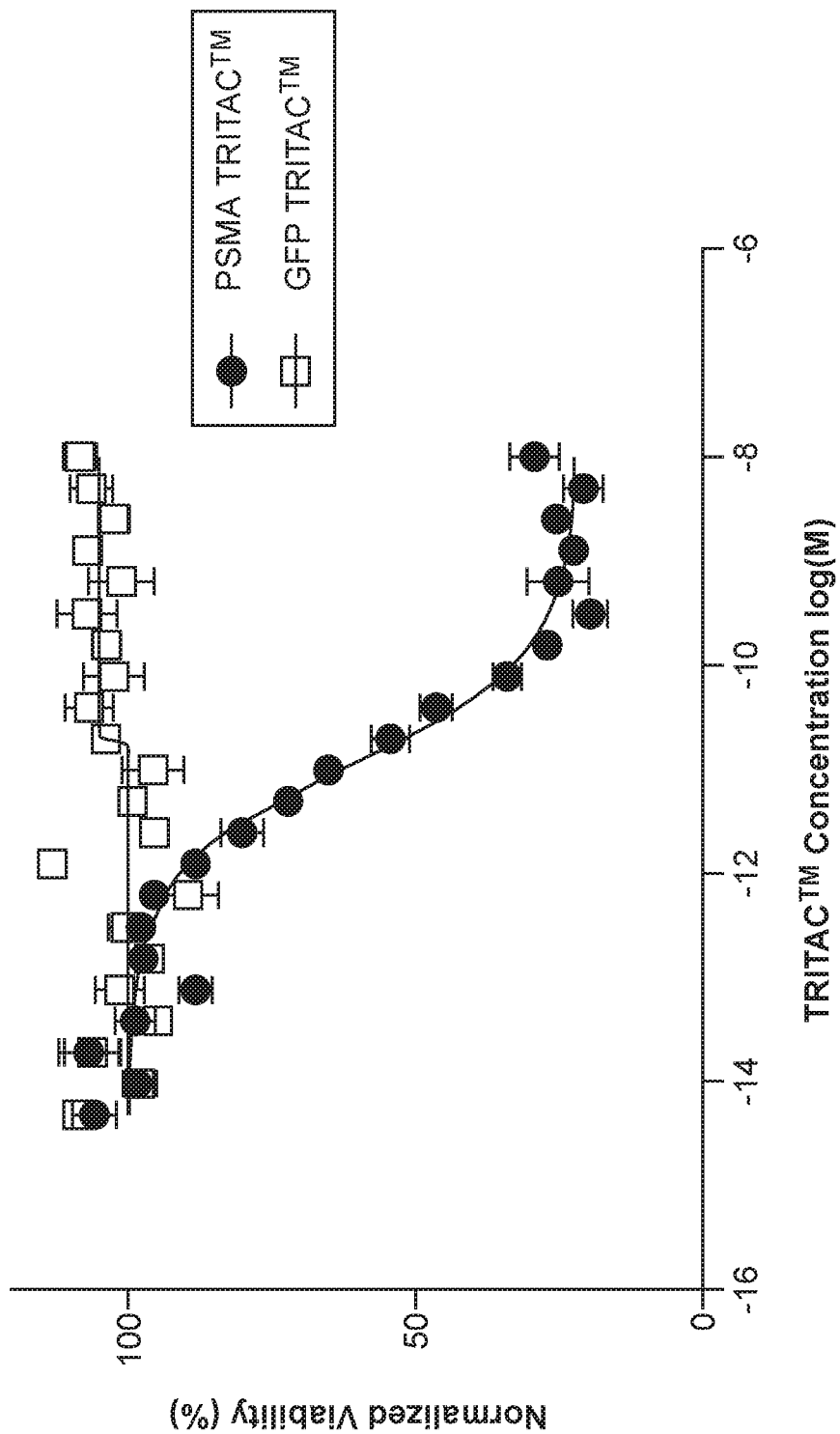
FIGS. 9A-B depict the activity of a PSMA targeting TRITAC™ molecule of this disclosure in redirected T cell killing in T cell dependent cellular cytotoxicity assays (TDCC).
Figure 9B:
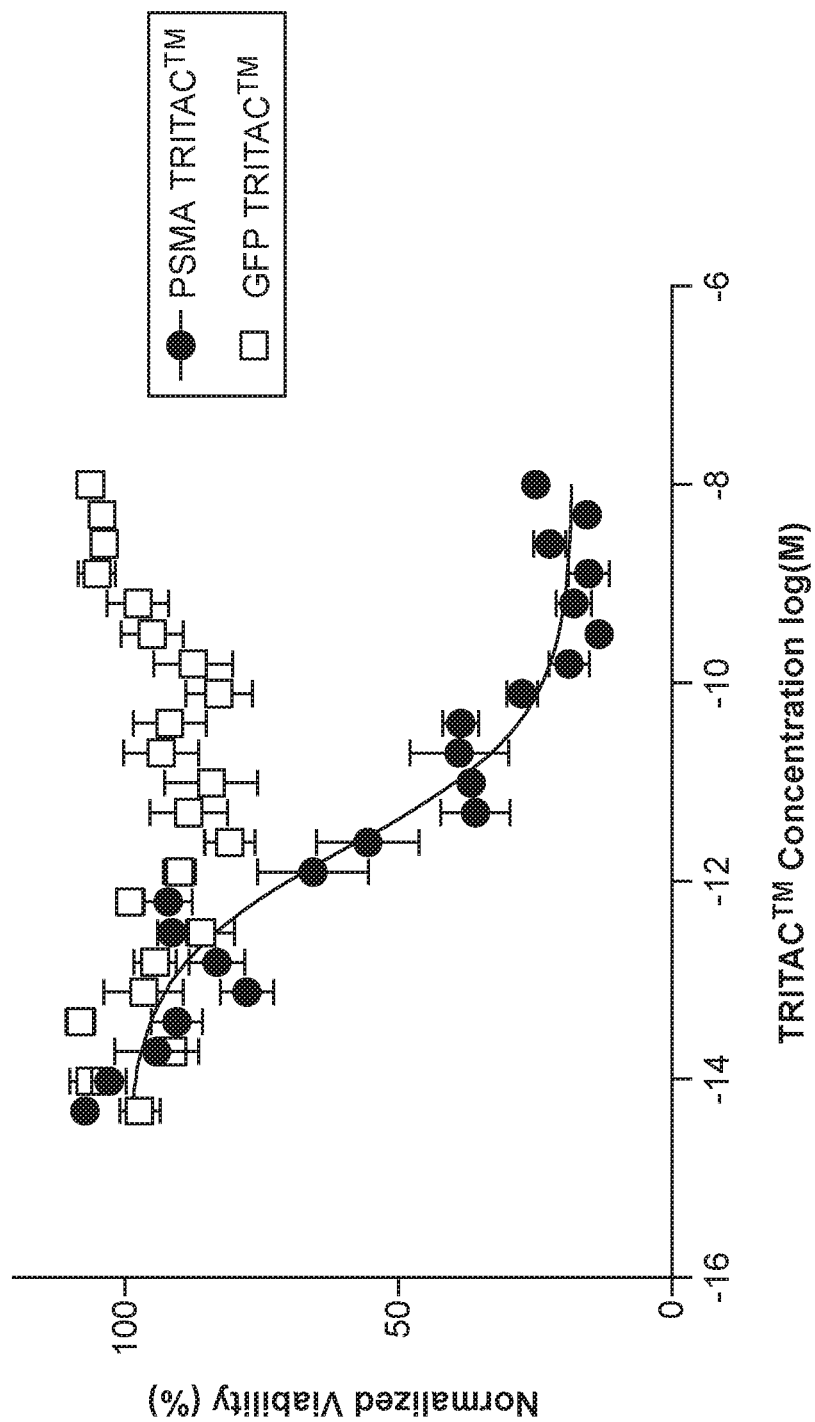

TDCC assays were set up using peripheral blood mononuclear cells (PBMCs) from cynomolgus monkeys. Cyno PBMCs were added to LNCaP cells at a 10:1 ratio. It was observed that the PSMA trispecific antigen-binding protein redirected killing of LNCaP by the cyno PBMCs with an EC$_{50}$ value of 11 pM. The result is shown in FIG. 9A. To confirm these results, a second cell line was used, MDAPCa2b, and PBMCs from a second cynomolgus monkey donor were tested. Redirected killing of the target cells was observed with an EC$_{50}$ value of 2.2 pM. The result is shown in FIG. 9B. Killing was specific to the anti-PMSA arm of the PSMA trispecific antigen-binding protein as killing was not observed with a negative control trispecific protein targeting GFP. These data demonstrate that the PSMA antigen-binding trispecific protein can direct cynomolgus T cells to kill target cells expressing human PSMA.

Example 13: Expression of Markers of T Cell Activation in Redirect T Cell Killing Assays with an Exemplary PSMA Trispecific Antigen-Binding Protein (PSMA Targeting TRITAC™ Molecule)

This study was performed to assess whether T cells were activated when the exemplary PSMA trispecific antigen-binding protein directed the T cells to kill target cells.

Figure 10:
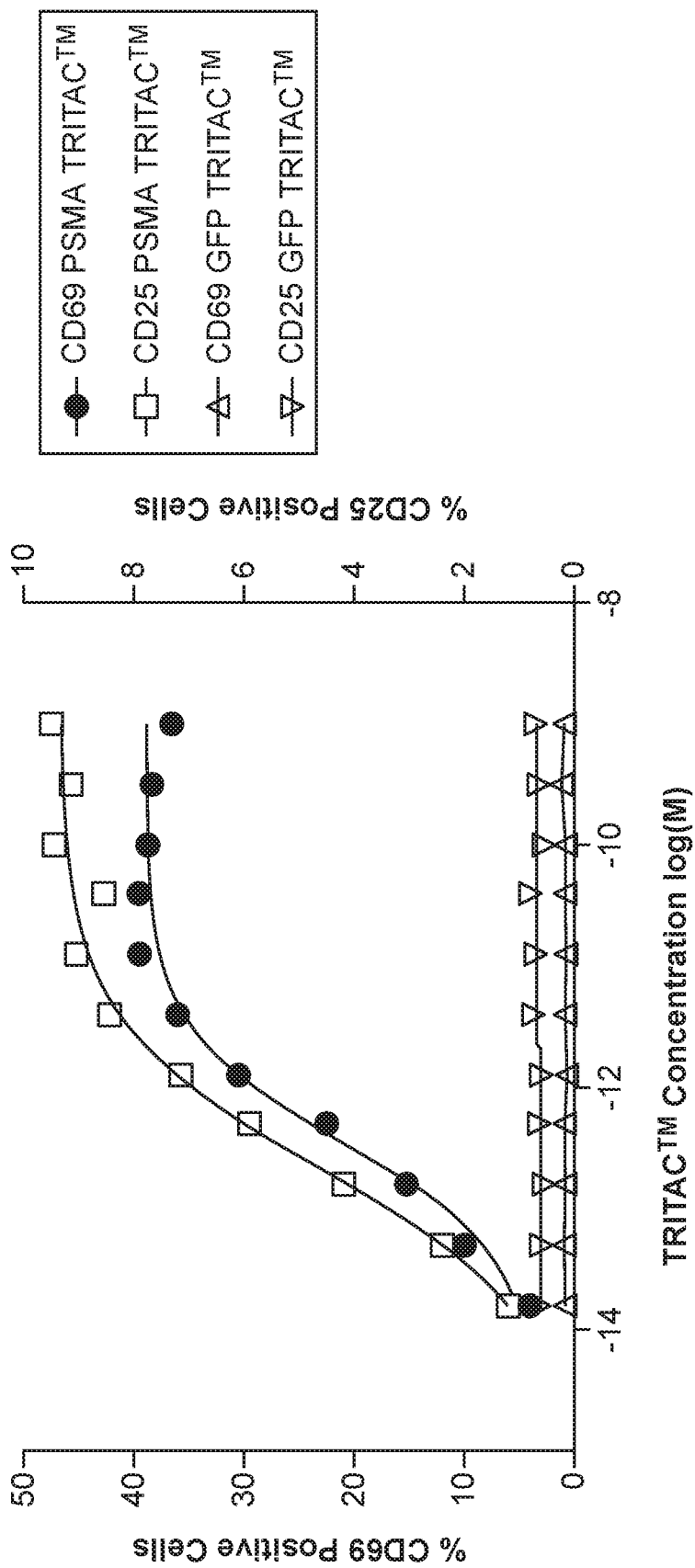
FIG. 10 depicts the impact of a PSMA targeting TRITAC™ molecule of this disclosure on expression of T cell activation markers CD25 and CD69.

The assays were set up using conditions for the redirected T cell killings assays described in the above example. T cell activation was assessed by measuring expression of CD25 and CD69 on the surface of the T cells using flow cytometry. The PSMA trispecific antigen-binding protein was added to a 10:1 mixture of purified human T cells and the prostate cancer cell line VCaP. Upon addition of increasing amounts of the PSMA trispecific antigen-binding protein, increased CD69 expression and CD25 expression was observed, as shown in FIG. 10. EC$_{50}$ value was 0.3 pM for CD69 and 0.2 pM for CD25. A trispecific protein targeting GFP was included in these assays as negative control, and little to no increase in CD69 or CD25 expression is observed with the GFP targeting trispecific protein, also shown in FIG. 10.

Example 14: Stimulation of T Cell Proliferation by an Exemplary PSMA Trispecific Antigen-Binding Protein (PSMA Targeting TRITAC™ Molecule) in the Presence of PSMA Expressing Target Cells This study was used as an additional method to demonstrate that the exemplary PSMA trispecific antigen-binding protein was able to activate T cells when it redirects them to kill target cells.

Figure 11:
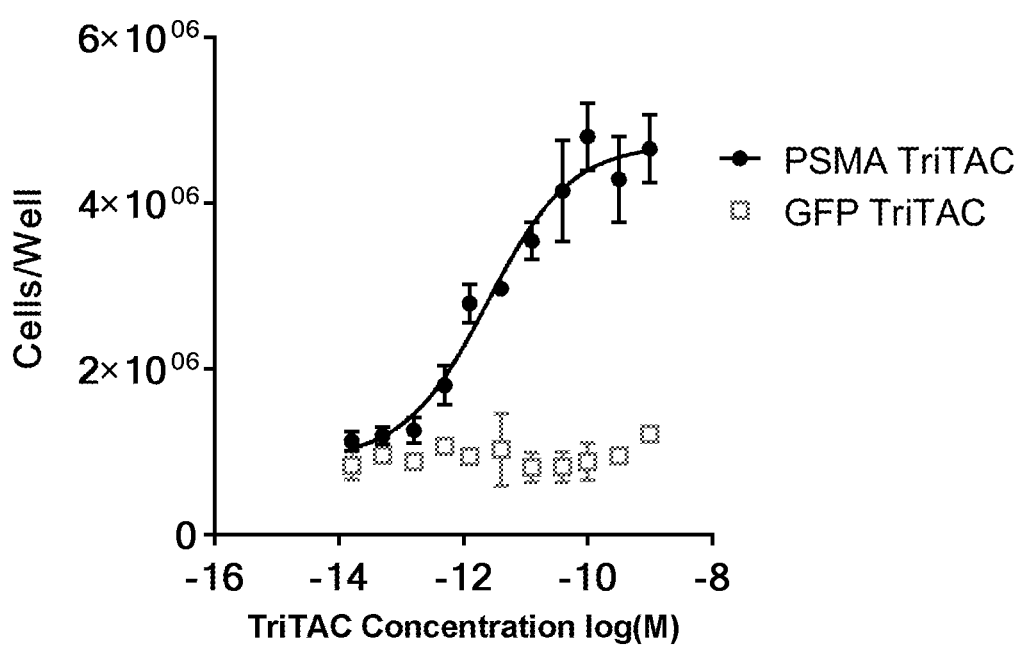
FIG. 11 depicts the ability of a PSMA targeting TRITAC™ molecule of this disclosure to stimulate T cell proliferation in the presence of PSMA expressing target cells.

T cell proliferation assays were set up using the conditions of the T cell redirected killing assay using LNCaP target cells, as described above, and measuring the number of T cells present at 72 hours. The exemplary PSMA trispecific antigen-binding protein stimulated proliferation with an $EC_{50}$ value of 0.5 pM. As negative control, a trispecific protein targeting GFP was included in the assay, and no increased proliferation was observed with this protein. The results for the T cell proliferation assay are illustrated in FIG. 11.

Example 15: Redirected T Cell Killing of LNCaP Cells by an Exemplary PSMA Trispecific Antigen-Binding Proteins (PSMA Targeting TRITAC™ Molecule Z2)

This study was carried out to test the ability of an exemplary PSMA trispecific antigen-binding protein, having the sequence as set forth in SEQ ID No: 156, to redirect T cells to kill the LNCaP cell line.

Figure 12:
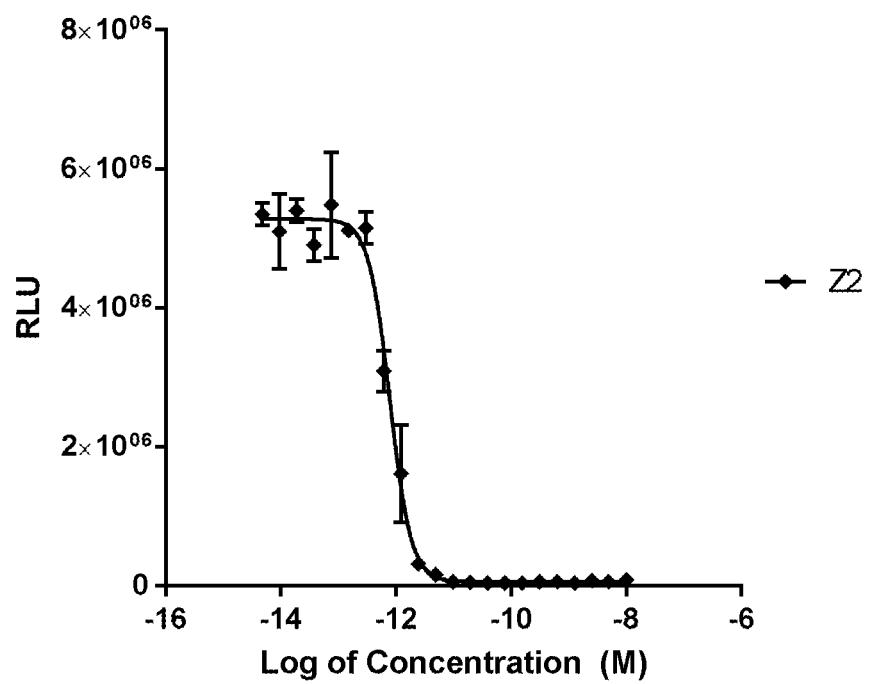
FIG. 12 depicts redirected T cell killing of LnCaP cells by PSMA targeting TRITAC™ molecule PSMA Z2 TRITAC™ (SEQ ID NO: 156).

In TDCC assays, set up as described in above examples, the PSMA Z2 TRITAC™ (SEQ ID NO: 156) protein directed killing with an $EC_{50}$ value of 0.8 pM, as shown in FIG. 12.

TABLE 8

| SEQ ID Nos. | Sequence |
| --- | --- |
| SEQ ID No. 1 | RFMISX$_1$YX$_2$MH |
| SEQ ID No. 2 | X$_3$INPAX$_4$X$_5$TDYAEX$_6$VKG |
| SEQ ID No. 3 | DX$_7$YGY |
| SEQ ID No. 4 | EVQLVESGGGLVQPGGSLTLSCAASRFMISEYSMHWVRQAPGKGLEWVSTINPAGTTDYAESV KGRFTISRDNAKNTLYLQMNSLKPEDTAVYYCDGYGYRGQGTQVTVSS |
| SEQ ID No. 5 | RFMISEYHMH |
| SEQ ID No. 6 | RFMISPYSMH |
| SEQ ID No. 7 | RFMISPYHMH |
| SEQ ID No. 8 | DINPAGTTDYAESVKG |
| SEQ ID No. 9 | TINPAKTTDYAESVKG |
| SEQ ID No. 10 | TINPAGQTDYAESVKG |
| SEQ ID No. 11 | TINPAGTTDYAEYVKG |
| SEQ ID No. 12 | DINPAKTTDYAESVKG |
| SEQ ID No. 13 | DINPAGQTDYAESVKG |
| SEQ ID No. 14 | DINPAGTTDYAEYVKG |
| SEQ ID No. 15 | DSYGY |
| SEQ ID No. 16 | RFMISEYSMH |
| SEQ ID No. 17 | TINPAGTTDYAESVKG |
| SEQ ID No. 18 | DGYGY |
| SEQ ID No. 19 | EVQLVESGGGLVQPGGSLRLSCAASRFMISEYSMHWVRQAPGKGLEWVSTINPAGTTDYAESV KGRFTISRDNAKNTLYLQMNSLRAEDTAVYYCDGYGYRGQGTLVTVSS |
| SEQ ID No. 20 | MWNLLHETDSAVATARRPRWLCAGALVLAGGFFLLGFLFGWFIKSSNEATNITPKHNMKAFLD ELKAENIKKFLYNFTQIPHLAGTEQNFQLAKQIQSQWKEFGLDSVELAHYDVLLSYPNKTHPN YISIINEDGNEIFNTSLFEPPPPGYENVSDIVPPFSAFSPQGMPEGDLVYVNYARTEDFFKLE RDMKINCSGKIVIARYGKVFRGNKVKNAQLAGAKGVILYSDPADYFAPGVKSYPDGWNLPGGG VQRGNILNLNGAGDPLTPGYPANEYAYRRGIAEAVGLPSIPVHPIGYYDAQKLLEKMGGSAPP DSSWRGSLKVPYNVGPGFTGNFSTQKVKMHIHSTNEVTRIYNVIGTLRGAVEPDRYVILGGHR DSWVFGGIDPQSGAAVVHEIVRSFGTLKKEGWRPRRTILFASWDAEEFGLLGSTEWAEENSRL LQERGVAYINADSSIEGNYTLRVDCTPLMYSLVHNLTKELKSPDEGFEGKSLYESWTKKSPSP EFSGMPRISKLGSGNDFEVFFQRLGIASGRARYTKNWETNKFSGYPLYHSVYETYELVEKFYD PMFKYHLTVAQVRGGMVFELANSIVLPFDCRDYAVVLRKYADKIYSISMKHPQEMKTYSVSFD SLFSAVKNFTEIASKFSERLQDFDKSNPIVLRMMNDQLMFLERAFIDPLGLPDRPFYRHVIYA PSSHNKYAGESFPGIYDALFDIESKVDPSKAWGEVKRQIYVAAFTVQAAAETLSEVA |
| SEQ ID No. 21 | EVQLVESGGGLVQPGGSLRLSCAASRFMISEYHMHWVRQAPGKGLEWVSDINPAGTTDYAESV KGRFTISRDNAKNTLYLQMNSLRAEDTAVYYCDSYGYRGQGTLVTVSS |

TABLE 8-continued

| SEQ ID Nos. | Sequence |
|---|---|
| SEQ ID No. 22 | EVQLVESGGGLVQPGGSLRLSCAASRFMISEYHMHWVRQAPGKGLEWVSTINPAGTTDYAESV<br>KGRFTISRDNAKNTLYLQMNSLRAEDTAVYYCDSYGYRGQGTLVTVSS |
| SEQ ID No. 23 | EVQLVESGGGLVQPGGSLRLSCAASRFMISEYSMHWVRQAPGKGLEWVSTINPAKTTDYAESV<br>KGRFTISRDNAKNTLYLQMNSLRAEDTAVYYCDSYGYRGQGTLVTVSS |
| SEQ ID No. 24 | EVQLVESGGGLVQPGGSLRLSCAASRFMISPYSMHWVRQAPGKGLEWVSTINPAGTTDYAESV<br>KGRFTISRDNAKNTLYLQMNSLRAEDTAVYYCDGYGYRGQGTLVTVSS |
| SEQ ID No. 25 | EVQLVESGGGLVQPGGSLRLSCAASRFMISEYSMHWVRQAPGKGLEWVSTINPAGQTDYAESV<br>KGRFTISRDNAKNTLYLQMNSLRAEDTAVYYCDGYGYRGQGTLVTVSS |
| SEQ ID No. 26 | EVQLVESGGGLVQPGGSLRLSCAASRFMISEYSMHWVRQAPGKGLEWVSTINPAGTTDYAEYV<br>KGRFTISRDNAKNTLYLQMNSLRAEDTAVYYCDGYGYRGQGTLVTVSS |
| SEQ ID No. 27 | EVQLVESGGGLVQPGGSLRLSCAASRFMISEYHMHWVRQAPGKGLEWVSDINPAKTTDYAESV<br>KGRFTISRDNAKNTLYLQMNSLRAEDTAVYYCDSYGYRGQGTLVTVSS |
| SEQ ID No. 28 | EVQLVESGGGLVQPGGSLRLSCAASRFMISPYHMHWVRQAPGKGLEWVSDINPAGTTDYAESV<br>KGRFTISRDNAKNTLYLQMNSLRAEDTAVYYCDGYGYRGQGTLVTVSS |
| SEQ ID No. 29 | EVQLVESGGGLVQPGGSLRLSCAASRFMISEYHMHWVRQAPGKGLEWVSDINPAGQTDYAESV<br>KGRFTISRDNAKNTLYLQMNSLRAEDTAVYYCDSYGYRGQGTLVTVSS |
| SEQ ID No. 30 | EVQLVESGGGLVQPGGSLRLSCAASRFMISEYHMHWVRQAPGKGLEWVSDINPAGTTDYAEYV<br>KGRFTISRDNAKNTLYLQMNSLRAEDTAVYYCDSYGYRGQGTLVTVSS |
| SEQ ID No. 31 | EVQLVESGGGLVQPGGSLTLSCAASRFMISEYHMHWVRQAPGKGLEWVSDINPAGTTDYAESV<br>KGRFTISRDNAKNTLYLQMNSLKPEDTAVYYCDSYGYRGQGTQVTVSS |
| SEQ ID No. 32 | EVQLVESGGGLVQPGGSLTLSCAASRFMISEYHMHWVRQAPGKGLEWVSTINPAGTTDYAESV<br>KGRFTISRDNAKNTLYLQMNSLKPEDTAVYYCDSYGYRGQGTQVTVSS |

TABLE 9

CD3 Binding Domain Sequences

| SEQ ID NO: | Description | AA Sequence |
|---|---|---|
| 34 | Anti-CD3, clone 2B2 | EVQLVESGGGLVQPGGSLKLSCAASGFTFNKYAINWVRQAPGKGL<br>EWVARIRSKYNNYATYYADQVKDRFTISRDDSKNTAYLQMNNLKT<br>EDTAVYYCVRHANFGNSYISYWAYWGQGTLVTVSSGGGGSGGGG<br>SGGGGSQTVVTQEPSLTVSPGGTVTLTCASSTGAVTSGNYPNWVQQ<br>KPGQAPRGLIGGTKFLVPGTPARFSGSLLGGKAALTLSGVQPEDEAE<br>YYCTLWYSNRWVFGGGTKLTVL |
| 35 | Anti-CD3, clone 9F2 | EVQLVESGGGLVQPGGSLKLSCAASGFEFNKYAMNWVRQAPGKG<br>LEWVARIRSKYNKYATYYADSVKDRFTISRDDSKNTAYLQMNNLK<br>TEDTAVYYCVRHGNFGNSYISYWAYWGQGTLVTVSSGGGGSGGG<br>GSGGGGSQTVVTQEPSLTVSPGGTVTLTCGSSFGAVTSGNYPNWVQ<br>QKPGQAPRGLIGGTKFLAPGTPARFSGSLLGGKAALTLSGVQPEDE<br>AEYYCVLWYDNRWVFGGGTKLTVL |
| 36 | Anti-CD3, clone 5A2 | EVQLVESGGGLVQPGGSLKLSCAASGFTFNKYAMNWVRQAPGKG<br>LEWVARIRSKYNNYATYYADSVKDRFTISRDDSKNTAYLQMNNLK<br>TEDTAVYYCVRHGNFGNSHISYWAYWGQGTLVTVSSGGGGSGGG<br>GSGGGGSQTVVTQEPSLTVSPGGTVTLTCGSSTGYVTSGNYPNWVQ<br>QKPGQAPRGLIGGTSFLAPGTPARFSGSLLGGKAALTLSGVQPEDEA<br>EYYCVLWYSNRWIFGGGTKLTVL |
| 37 | Anti-CD3, clone 6A2 | EVQLVESGGGLVQPGGSLKLSCAASGFMFNKYAMNWVRQAPGKG<br>LEWVARIRSKSNNYATYYADSVKDRFTISRDDSKNTAYLQMNNLK<br>TEDTAVYYCVRHGNFGNSYISYWATWGQGTLVTVSSGGGGSGGG<br>GSGGGGSQTVVTQEPSLTVSPGGTVTLTCGSSFGAVTSGNYPNWVQ<br>QKPGQAPRGLIGGTKLLAPGTPARFSGSLLGGKAALTLSGVQPEDE<br>AEYYCVLWYSNSWVFGGGTKLTVL |
| 38 | Anti-CD3, clone 2D2 | EVQLVESGGGLVQPGGSLKLSCAASGFTFNTYAMNWVRQAPGKGL<br>EWVARIRSKYNNYATYYKDSVKDRFTISRDDSKNTAYLQMNNLKT<br>EDTAVYYCVRHGNFGNSPISYWAYWGQGTLVTVSSGGGGSGGGG<br>SGGGGSQTVVTQEPSLTVSPGGTVTLTCGSSTGAVVSGNYPNWVQ<br>QKPGQAPRGLIGGTEFLAPGTPARFSGSLLGGKAALTLSGVQPEDEA<br>EYYCVLWYSNRWVFGGGTKLTVL |

TABLE 9-continued

CD3 Binding Domain Sequences

| SEQ ID NO: | Description | AA Sequence |
|---|---|---|
| 39 | Anti-CD3, clone 3F2 | EVQLVESGGGLVQPGGSLKLSCAASGFTYNKYAMNWVRQAPGKG<br>LEWVARIRSKYNNYATYYADEVKDRFTISRDDSKNTAYLQMNNLK<br>TEDTAVYYCVRHGNFGNSPISYWAYWGQGTLVTVSSGGGGSGGG<br>GSGGGGSQTVVTQEPSLTVSPGGTVTLTCGSSKGAVTSGNYPNWV<br>QQKPGQAPRGLIGGTKELAPGTPARFSGSLLGGKAALTLSGVQPED<br>EAEYYCTLWYSNRWVFGGGTKLTVL |
| 40 | Anti-CD3, clone 1A2 | EVQLVESGGGLVQPGGSLKLSCAASGNTFNKYAMNWVRQAPGKG<br>LEWVARIRSKYNNYETYYADSVKDRFTISRDDSKNTAYLQMNNLK<br>TEDTAVYYCVRHTNFGNSYISYWAYWGQGTLVTVSSGGGGSGGG<br>GSGGGGSQTVVTQEPSLTVSPGGTVTLTCGSSTGAVTSGYYPNWVQ<br>QKPGQAPRGLIGGTYFLAPGTPARFSGSLLGGKAALTLSGVQPEDE<br>AEYYCVLWYSNRWVFGGGTKLTVL |
| 41 | Anti-CD3, clone 1C2 | EVQLVESGGGLVQPGGSLKLSCAASGFTFNNYAMNWVRQAPGKG<br>LEWVARIRSKYNNYATYYADAVKDRFTISRDDSKNTAYLQMNNLK<br>TEDTAVYYCVRHGNFGNSQISYWAYWGQGTLVTVSSGGGGSGGG<br>GSGGGGSQTVVTQEPSLTVSPGGTVTLTCGSSTGAVTDGNYPNWV<br>QQKPGQAPRGLIGGIKFLAPGTPARFSGSLLGGKAALTLSGVQPEDE<br>AEYYCVLWYSNRWVFGGGTKLTVL |
| 42 | Anti-CD3, clone 2E4 | EVQLVESGGGLVQPGGSLKLSCAASGFTFNKYAVNWVRQAPGKGL<br>EWVARIRSKYNNYATYYADSVKDRFTISRDDSKNTAYLQMNNLKT<br>EDTAVYYCVRHGNFGNSYISYWAYWGQGTLVTVSSGGGGSGGGG<br>SGGGGSQTVVTQEPSLTVSPGGTVTLTCGESTGAVTSGNYPNWVQ<br>QKPGQAPRGLIGGTKILAPGTPARFSGSLLGGKAALTLSGVQPEDEA<br>EYYCVLWYSNRWVFGGGTKLTVL |
| 43 | Anti-CD3, clone 10E4 | EVQLVESGGGLVQPGGSLKLSCAASGFTFNKYPMNWVRQAPGKGL<br>EWVARIRSKYNNYATYYADSVKDRFTISRDDSKNTAYLQMNNLKN<br>EDTAVYYCVRHGNFNNSYISYWAYWGQGTLVTVSSGGGGSGGGG<br>SGGGGSQTVVTQEPSLTVSPGGTVTLTCGSSTGAVTKGNYPNWVQ<br>QKPGQAPRGLIGGTKMLAPGTPARFSGSLLGGKAALTLSGVQPEDE<br>AEYYCALWYSNRWVFGGGTKLTVL |
| 44 | Anti-CD3, clone 2H2 | EVQLVESGGGLVQPGGSLKLSCAASGFTFNGYAMNWVRQAPGKG<br>LEWVARIRSKYNNYATYYADEVKDRFTISRDDSKNTAYLQMNNLK<br>TEDTAVYYCVRHGNFGNSPISYWAYWGQGTLVTVSSGGGGSGGG<br>GSGGGGSQTVVTQEPSLTVSPGGTVTLTCGSSTGAVVSGNYPNWV<br>QQKPGQAPRGLIGGTEFLAPGTPARFSGSLLGGKAALTLSGVQPEDE<br>AEYYCVLWYSNRWVFGGGTKLTVL |
| 45 | Anti-CD3, clone 2A4 | EVQLVESGGGLVQPGGSLKLSCAASGNTFNKYAMNWVRQAPGKG<br>LEWVARIRSKYNNYATYYADSVKDRFTISRDDSKNTAYLQMNNLK<br>TEDTAVYYCVRHGNFGDSYISYWAYWGQGTLVTVSSGGGGSGGG<br>GSGGGGSQTVVTQEPSLTVSPGGTVTLTCGSSTGAVTHGNYPNWV<br>QQKPGQAPRGLIGGTKVLAPGTPARFSGSLLGGKAALTLSGVQPED<br>EAEYYCVLWYSNRWVFGGGTKLTVL |
| 46 | Anti-CD3, clone 10B2 | EVQLVESGGGLVQPGGSLKLSCAASGFTFNNYAMNWVRQAPGKG<br>LEWVARIRSGYNNYATYYADSVKDRFTISRDDSKNTAYLQMNNLK<br>TEDTAVYYCVRHGNFGNSYISYWAYWGQGTLVTVSSGGGGSGGG<br>GSGGGGSQTVVTQEPSLTVSPGGTVTLTCGSYTGAVTSGNYPNWV<br>QQKPGQAPRGLIGGTKFNAPGTPARFSGSLLGGKAALTLSGVQPED<br>EAEYYCVLWYANRWVFGGGTKLTVL |
| 47 | Anti-CD3, clone 1G4 | EVQLVESGGGLVQPGGSLKLSCAASGFEFNKYAMNWVRQAPGKG<br>LEWVARIRSKYNNYETYYADSVKDRFTISRDDSKNTAYLQMNNLK<br>TEDTAVYYCVRHGNFGNSLISYWAYWGQGTLVTVSSGGGGSGGG<br>GSGGGGSQTVVTQEPSLTVSPGGTVTLTCGSSSGAVTSGNYPNWVQ<br>QKPGQAPRGLIGGTKFGAPGTPARFSGSLLGGKAALTLSGVQPEDE<br>AEYYCVLWYSNRWVFGGGTKLTVL |
| 48 | wt anti-CD3 | EVQLVESGGGLVQPGGSLKLSCAASGFTFNKYAMNWVRQAPGKG<br>LEWVARIRSKYNNYATYYADSVKDRFTISRDDSKNTAYLQMNNLK<br>TEDTAVYYCVRHGNFGNSYISYWAYWGQGTLVTVSSGGGGSGGG<br>GSGGGGSQTVVTQEPSLTVSPGGTVTLTCGSSTGAVTSGNYPNWVQ<br>QKPGQAPRGLIGGTKFLAPGTPARFSGSLLGGKAALTLSGVQPEDE<br>AEYYCVLWYSNRWVFGGGTKLTVL |
| 49 | wt anti-CD3 HC CDR1 | GFTFNKYAMN |
| 50 | wt anti-CD3 HC CDR2 | RIRSKYNNYATYYADSVK |

TABLE 9-continued

CD3 Binding Domain Sequences

| SEQ ID NO: | Description | AA Sequence |
|---|---|---|
| 51 | wt anti-CD3 HC CDR3 | HGNFGNSYISYWAY |
| 53 | wt anti-CD3 LC CDR1 | GSSTGAVTSGNYPN |
| 54 | wt anti-CD3 LC CDR2 | GTKFLAP |
| 55 | wt anti-CD3 LC CDR3 | VLWYSNRWV |
| 56 | HC CDR1 variant 1 | GNTFNKYAMN |
| 57 | HC CDR1 variant 2 | GFEFNKYAMN |
| 58 | HC CDR1 variant 3 | GFMFNKYAMN |
| 59 | HC CDR1 variant 4 | GFTYNKYAMN |
| 60 | HC CDR1 variant 5 | GFTFNNYAMN |
| 61 | HC CDR1 variant 6 | GFTFNGYAMN |
| 62 | HC CDR1 variant 7 | GFTFNTYAMN |
| 63 | HC CDR1 variant 8 | GFTFNEYAMN |
| 64 | HC CDR1 variant 9 | GFTFNKYPMN |
| 65 | HC CDR1 variant 10 | GFTFNKYAVN |
| 66 | HC CDR1 variant 11 | GFTFNKYAIN |
| 67 | HC CDR1 variant 12 | GFTFNKYALN |
| 68 | HC CDR2 variant 1 | RIRSGYNNYATYYADSVK |
| 69 | HC CDR2 variant 2 | RIRSKSNNYATYYADSVK |
| 70 | HC CDR2 variant 3 | RIRSKYNKYATYYADSVK |
| 71 | HC CDR2 variant 4 | RIRSKYNNYETYYADSVK |
| 72 | HC CDR2 variant 5 | RIRSKYNNYATEYADSVK |
| 73 | HC CDR2 variant 6 | RIRSKYNNYATYYKDSVK |
| 74 | HC CDR2 variant 7 | RIRSKYNNYATYYADEVK |
| 75 | HC CDR2 variant 8 | RIRSKYNNYATYYADAVK |
| 76 | HC CDR2 variant 9 | RIRSKYNNYATYYADQVK |
| 77 | HC CDR2 variant 10 | RIRSKYNNYATYYADDVK |
| 78 | HC CDR3 variant 1 | HANFGNSYISYWAY |
| 79 | HC CDR3 variant 2 | HTNFGNSYISYWAY |
| 80 | HC CDR3 variant 3 | HGNFNNSYISYWAY |
| 81 | HC CDR3 variant 4 | HGNFGDSYISYWAY |
| 82 | HC CDR3 variant 5 | HGNFGNSHISYWAY |
| 83 | HC CDR3 variant 6 | HGNFGNSPISYWAY |
| 84 | HC CDR3 variant 7 | HGNFGNSQISYWAY |
| 85 | HC CDR3 variant 8 | HGNFGNSLISYWAY |
| 86 | HC CDR3 variant 9 | HGNFGNSGISYWAY |
| 87 | HC CDR3 variant 10 | HGNFGNSYISYWAT |
| 88 | LC CDR1 variant 1 | ASSTGAVTSGNYPN |

TABLE 9-continued

| | CD3 Binding Domain Sequences | |
|---|---|---|
| SEQ ID NO: | Description | AA Sequence |
| 89 | LC CDR1 variant 2 | GESTGAVTSGNYPN |
| 90 | LC CDR1 variant 3 | GSYTGAVTSGNYPN |
| 91 | LC CDR1 variant 4 | GSSFGAVTSGNYPN |
| 92 | LC CDR1 variant 5 | GSSKGAVTSGNYPN |
| 93 | LC CDR1 variant 6 | GSSSGAVTSGNYPN |
| 94 | LC CDR1 variant 7 | GSSTGYVTSGNYPN |
| 95 | LC CDR1 variant 8 | GSSTGAVVSGNYPN |
| 96 | LC CDR1 variant 9 | GSSTGAVTDGNYPN |
| 97 | LC CDR1 variant 10 | GSSTGAVTKGNYPN |
| 98 | LC CDR1 variant 11 | GSSTGAVTHGNYPN |
| 99 | LC CDR1 variant 12 | GSSTGAVTVGNYPN |
| 100 | LC CDR1 variant 13 | GSSTGAVTSGYYPN |
| 101 | LC CDR2 variant 1 | GIKFLAP |
| 102 | LC CDR2 variant 2 | GTEFLAP |
| 103 | LC CDR2 variant 3 | GTYFLAP |
| 104 | LC CDR2 variant 4 | GTSFLAP |
| 105 | LC CDR2 variant 5 | GTNFLAP |
| 106 | LC CDR2 variant 6 | GTKLLAP |
| 107 | LC CDR2 variant 7 | GTKELAP |
| 108 | LC CDR2 variant 8 | GTKILAP |
| 109 | LC CDR2 variant 9 | GTKMLAP |
| 110 | LC CDR2 variant 10 | GTKVLAP |
| 111 | LC CDR2 variant 11 | GTKFNAP |
| 112 | LC CDR2 variant 12 | GTKFGAP |
| 113 | LC CDR2 variant 13 | GTKFLVP |
| 114 | LC CDR3 variant 1 | TLWYSNRWV |
| 115 | LC CDR3 variant 2 | ALWYSNRWV |
| 116 | LC CDR3 variant 3 | VLWYDNRWV |
| 117 | LC CDR3 variant 4 | VLWYANRWV |
| 118 | LC CDR3 variant 5 | VLWYSNSWV |
| 119 | LC CDR3 variant 6 | VLWYSNRWI |
| 120 | LC CDR3 variant 7 | VLWYSNRWA |
| 121 | Anti-CD3, clone 2G5 | EVQLVESGGGLVQPGGSLKLSCAASGFTFNKYALNWVRQAPGKGL<br>EWVARIRSKYNNYATEYADSVKDRFTISRDDSKNTAYLQMNNLKT<br>EDTAVYYCVRHGNFGNSPISYWAYWGQGTLVTVSSGGGGSGGGG<br>SGGGGSQTVVTQEPSLTVSPGGTVTLTCGSSTGAVTSGNYPNWVQQ<br>KPGQAPRGLIGGTNFLAPGTPERFSGSLLGGKAALTLSGVQPEDEAE<br>YYCVLWYSNRWAFGGGTKLTVL |
| 122 | Anti-CD3, clone 8A5 | EVQLVESGGGLVQPGGSLKLSCAASGFTFNEYAMNWVRQAPGKGL<br>EWVARIRSKYNNYATYYADDVKDRFTISRDDSKNTAYLQMNNLKT |

TABLE 9-continued

CD3 Binding Domain Sequences

| SEQ ID NO: | Description | AA Sequence |
|---|---|---|
| | | EDTAVYYCVRHGNFGNSGISYWAYWGQGTLVTVSSGGGGSGGGG SGGGGSQTVVTQEPSLTVSPGGTVTLTCGSSTGAVTVGNYPNWVQ QKPGQAPRGLIGGTEFLAPGTPARFSGSLLGGKAALTLSGVQPEDEA EYYCVLWYSNRWVFGGGTKLTVL |

TABLE 10

HSA Binding Domain Sequences

| SEQ ID NO: | Description | AA Sequence |
|---|---|---|
| 123 | Anti-HSA sdAb clone 6C | EVQLVESGGGLVQPGNSLRLSCAASGFTFSRFGMSWVRQAPGKGL EWVSSISGSGSDTLYADSVKGRFTISRDNAKTTLYLQMNSLRPEDTA VYYCTIGGSLSRSSQGTLVTVSS |
| 124 | Anti-HSA sdAb clone 7A | EVQLVESGGGLVQPGNSLRLSCAASGFTFSKFGMSWVRQAPGKGL EWVSSISGSGADTLYADSLKGRFTISRDNAKTTLYLQMNSLRPEDT AVYYCTIGGSLSKSSQGTLVTVSS |
| 125 | Anti-HSA sdAb clone 7G | EVQLVESGGGLVQPGNSLRLSCAASGFTYSSFGMSWVRQAPGKGL EWVSSISGSGSDTLYADSVKGRFTISRDNAKTTLYLQMNSLRPEDTA VYYCTIGGSLSKSSQGTLVTVSS |
| 126 | Anti-HSA sdAb clone 8H | EVQLVESGGGLVQPGNSLRLSCAASGFTFSKFGMSWVRQAPGKGL EWVSSISGSGTDTLYADSVKGRFTISRDNAKTTLYLQMNSLRPEDT AVYYCTIGGSLSRSSQGTLVTVSS |
| 127 | Anti-HSA sdAb clone 9A | EVQLVESGGGLVQPGNSLRLSCAASGFTFSRFGMSWVRQAPGKGL EWVSSISGSGSDTLYADSVKGRFTISRDNAKTTLYLQMNSLRPEDTA VYYCTIGGSLSKSSQGTLVTVSS |
| 128 | Anti-HSA sdAb clone 10G | EVQLVESGGGLVQPGNSLRLSCAASGFTFSKFGMSWVRQAPGKGL EWVSSISGSGRDTLYADSVKGRFTISRDNAKTTLYLQMNSLRPEDT AVYYCTIGGSLSVSSQGTLVTVSS |
| 129 | wt anti-HSA | EVQLVESGGGLVQPGNSLRLSCAASGFTFSSFGMSWVRQAPGKGLE WVSSISGSGSDTLYADSVKGRFTISRDNAKTTLYLQMNSLRPEDTA VYYCTIGGSLSRSSQGTLVTVSS |
| 130 | wt anti-HSA CDR1 | GFTFSSFGMS |
| 131 | wt anti-HSA CDR2 | SISGSGSDTLYADSVK |
| 132 | wt anti-HSACDR3 | GGSLSR |
| 133 | CDR1 variant 1 | GFTFSRFGMS |
| 134 | CDR1 variant 2 | GFTFSKFGMS |
| 135 | CDR1 variant 3 | GFTYSSFGMS |
| 136 | CDR2 variant 1 | SISGSGADTLYADSLK |
| 137 | CDR2 variant 2 | SISGSGTDTLYADSVK |
| 138 | CDR2 variant 3 | SISGSGRDTLYADSVK |
| 139 | CDR2 variant 4 | SISGSGSDTLYAESVK |
| 140 | CDR2 variant 5 | SISGSGTDTLYAESVK |
| 141 | CDR2 variant 6 | SISGSGRDTLYAESVK |
| 142 | CDR3 variant 1 | GGSLSK |
| 143 | CDR3 variant 2 | GGSLSV |

TABLE 10-continued

HSA Binding Domain Sequences

| SEQ ID NO: | Description | AA Sequence |
|---|---|---|
| 144 | Anti-HSA sdAb clone 6CE | EVQLVESGGGLVQPGNSLRLSCAASGFTFSRFGMSWVRQAPGKGL EWVSSISGSGSDTLYAESVKGRFTISRDNAKTTLYLQMNSLRPEDTA VYYCTIGGSLSRSSQGTLVTVSS |
| 145 | Anti-HSA sdAb clone 8HE | EVQLVESGGGLVQPGNSLRLSCAASGFTFSKFGMSWVRQAPGKGL EWVSSISGSGTDTLYAESVKGRFTISRDNAKTTLYLQMNSLRPEDTA VYYCTIGGSLSRSSQGTLVTVSS |
| 146 | Anti-HSA sdAb clone 10GE | EVQLVESGGGLVQPGNSLRLSCAASGFTFSKFGMSWVRQAPGKGL EWVSSISGSGRDTLYAESVKGRFTISRDNAKTTLYLQMNSLRPEDTA VYYCTIGGSLSVSSQGTLVTVSS |

TABLE 11

PSMA Targeting Trispecific Protein Sequences

| SEQ ID NO: | C-Number | Construct | Sequence |
|---|---|---|---|
| 147 | C00324 | PSMA TriTAC ™ CD3 high aff. | EVQLVESGGGLVQPGGSLTLSCAASRFMISEYSMHWVRQAPGK GLEWVSTINPAGTTDYAESVKGRFTISRDNAKNTLYLQMNSLKP EDTAVYYCDGYGYRGQGTQVTVSSGGGGSGGGGSEVQLVESGG GLVQPGNSLRLSCAASGFTFSKFGMSWVRQAPGKGLEWVSSISG SGRDTLYADSVKGRFTISRDNAKTTLYLQMNSLRPEDTAVYYCT IGGSLSVSSQGTLVTVSSGGGGSGGGGSEVQLVESGGGLVQPGGS LKLSCAASGFTFNKYAINWVRQAPGKGLEWVARIRSKYNNYAT YYADQVKDRFTISRDDSKNTAYLQMNNLKTEDTAVYYCVRHA NFGNSYISYWAYWGQGTLVTVSSGGGGSGGGGSGGGGSQTVV TQEPSLTVSPGGTVTLTCASSTGAVTSGNYPNWVQQKPGQAPRG LIGGTKFLVPGTPARFSGSLLGGKAALTLSGVQPEDEAEYYCTL WYSNRWVFGGGTKLTVLHHHHHH |
| 148 | C00339 | PSMA TriTAC ™ CD3 med. aff. | EVQLVESGGGLVQPGGSLTLSCAASRFMISEYSMHWVRQAPGK GLEWVSTINPAGTTDYAESVKGRFTISRDNAKNTLYLQMNSLKP EDTAVYYCDGYGYRGQGTQVTVSSGGGGSGGGGSEVQLVESGG GLVQPGNSLRLSCAASGFTFSKFGMSWVRQAPGKGLEWVSSISG SGRDTLYADSVKGRFTISRDNAKTTLYLQMNSLRPEDTAVYYCT IGGSLSVSSQGTLVTVSSGGGGSGGGGSEVQLVESGGGLVQPGGS LKLSCAASGFTFNNYAMNWVRQAPGKGLEWVARIRSGYNNYA TYYADSVKDRFTISRDDSKNTAYLQMNNLKTEDTAVYYCVRHG NFGNSYISYWAYWGQGTLVTVSSGGGGSGGGGSGGGGSQTVV TQEPSLTVSPGGTVTLTCGSYTGAVTSGNYPNWVQQKPGQAPR GLIGGTKFNAPGTPARFSGSLLGGKAALTLSGVQPEDEAEYYCV LWYANRWVFGGGTKLTVLHHHHHH |
| 149 | C00325 | PSMA TriTAC ™ CD3 low aff. | EVQLVESGGGLVQPGGSLTLSCAASRFMISEYSMHWVRQAPGK GLEWVSTINPAGTTDYAESVKGRFTISRDNAKNTLYLQMNSLKP EDTAVYYCDGYGYRGQGTQVTVSSGGGGSGGGGSEVQLVESGG GLVQPGNSLRLSCAASGFTFSKFGMSWVRQAPGKGLEWVSSISG SGRDTLYADSVKGRFTISRDNAKTTLYLQMNSLRPEDTAVYYCT IGGSLSVSSQGTLVTVSSGGGGSGGGGSEVQLVESGGGLVQPGGS LKLSCAASGFEFNKYAMNWVRQAPGKGLEWVARIRSKYNNYE TYYADSVKDRFTISRDDSKNTAYLQMNNLKTEDTAVYYCVRHG NFGNSLISYWAYWGQGTLVTVSSGGGGSGGGGSGGGGSQTVVT QEPSLTVSPGGTVTLTCGSSSGAVTSGNYPNWVQQKPGQAPRGL IGGTKFGAPGTPARFSGSLLGGKAALTLSGVQPEDEAEYYCVLW YSNRWVFGGGTKLTVLHHHHHH |
| 150 | C00236 | Tool PSMA TriTAC ™ | EVQLVESGGGLVQPGGSLTLSCAASRFMISEYSMHWVRQAPGK GLEWVSTINPAGTTDYAESVKGRFTISRDNAKNTLYLQMNSLKP EDTAVYYCDGYGYRGQGTQVTVSSGGGGSGGGGSEVQLVESGG GLVQPGNSLRLSCAASGFTFSSFGMSWVRQAPGKGLEWVSSISG SGSDTLYADSVKGRFTISRDNAKTTLYLQMNSLRPEDTAVYYCT IGGSLSRSSQGTLVTVSSGGGGSGGGGSEVQLVESGGGLVQPGGS LKLSCAASGFTFNKYAMNWVRQAPGKGLEWVARIRSKYNNYA TYYADSVKDRFTISRDDSKNTAYLQMNNLKTEDTAVYYCVRHG NFGNSYISYWAYWGQGTLVTVSSGGGGSGGGGSGGGGSQTVV TQEPSLTVSPGGTVTLTCGSSTGAVTSGNYPNWVQQKPGQAPRG LIGGTKFLAPGTPARFSGSLLGGKAALTLSGVQPEDEAEYYCVL WYSNRWVFGGGTKLTVLHHHHHH |

TABLE 11-continued

PSMA Targeting Trispecific Protein Sequences

| SEQ ID NO: | C-Number | Construct | Sequence |
|---|---|---|---|
| 151 | C00362 | PSMA p8 TriTAC ™ | EVQLVESGGGLVQPGGSLRLSCAASRFMISEYSMHWVRQAPGK GLEWVSTINPAGTTDYAESVKGRFTISRDNAKNTLYLQMNSLRA EDTAVYYCDGYGYRGQGTLVTVSSGGGGSGGGSEVQLVESGG GLVQPGNSLRLSCAASGFTFSKFGMSWVRQAPGKGLEWVSSISG SGRDTLYADSVKGRFTISRDNAKTTLYLQMNSLRPEDTAVYYCT IGGSLSVSSQGTLVTVSSGGGGSGGGSEVQLVESGGGLVQPGGS LKLSCAASGFTFNKYAINWVRQAPGKGLEWVARIRSKYNNYAT YYADQVKDRFTISRDDSKNTAYLQMNNLKTEDTAVYYCVRHA NFGNSYISYWAYWGQGTLVTVSSGGGGSGGGGSGGGGSQTVV TQEPSLTVSPGGTVTLTCASSTGAVTSGNYPNWVQQKPGQAPRG LIGGTKFLVPGTPARFSGSLLGGKAALTLSGVQPEDEAEYYCTL WYSNRWVFGGGTKLTVLHHHHHH |
| 152 | C00363 | PSMA HDS TriTAC ™ C363 | EVQLVESGGGLVQPGGSLTLSCAASRFMISEYHMHWVRQAPGK GLEWVSDINPAGTTDYAESVKGRFTISRDNAKNTLYLQMNSLKP EDTAVYYCDSYGYRGQGTQVTVSSGGGGSGGGSEVQLVESGGG LVQPGNSLRLSCAASGFTFSKFGMSWVRQAPGKGLEWVSSISGS GRDTLYADSVKGRFTISRDNAKTTLYLQMNSLRPEDTAVYYCTI GGSLSVSSQGTLVTVSSGGGGSGGGSEVQLVESGGGLVQPGGSL KLSCAASGFTFNKYAINWVRQAPGKGLEWVARIRSKYNNYATY YADQVKDRFTISRDDSKNTAYLQMNNLKTEDTAVYYCVRHANF GNSYISYWAYWGQGTLVTVSSGGGGSGGGGSGGGGSQTVVTQ EPSLTVSPGGTVTLTCASSTGAVTSGNYPNWVQQKPGQAPRGLI GGTKFLVPGTPARFSGSLLGGKAALTLSGVQPEDEAEYYCTLWY SNRWVFGGGTKLTVLHHHHHH |
| 153 | C00364 | PSMA HTS TriTAC ™ C364 | EVQLVESGGGLVQPGGSLTLSCAASRFMISEYHMHWVRQAPGK GLEWVSTINPAGTTDYAESVKGRFTISRDNAKNTLYLQMNSLKP EDTAVYYCDSYGYRGQGTQVTVSSGGGGSGGGSEVQLVESGGG LVQPGNSLRLSCAASGFTFSKFGMSWVRQAPGKGLEWVSSISGS GRDTLYADSVKGRFTISRDNAKTTLYLQMNSLRPEDTAVYYCTI GGSLSVSSQGTLVTVSSGGGGSGGGSEVQLVESGGGLVQPGGSL KLSCAASGFTFNKYAINWVRQAPGKGLEWVARIRSKYNNYATY YADQVKDRFTISRDDSKNTAYLQMNNLKTEDTAVYYCVRHANF GNSYISYWAYWGQGTLVTVSSGGGGSGGGGSGGGGSQTVVTQ EPSLTVSPGGTVTLTCASSTGAVTSGNYPNWVQQKPGQAPRGLI GGTKFLVPGTPARFSGSLLGGKAALTLSGVQPEDEAEYYCTLWY SNRWVFGGGTKLTVLHHHHHH |
| 154 | C00298 | PSMA BiTE | QVQLVESGGGLVKPGESLRLSCAASGFTFSDYYMYWVRQAPGK GLEWVAIISDGGYYTYYSDIIKGRFTISRDNAKNSLYLQMNSLKA EDTAVYYCARGFPLLRHGAMDYWGQGTLVTVSSGGGGSGGGG SGGGGSDIQMTQSPSSLSASVGDRVTITCKASQNVDTNVAWYQ QKPGQAPKSLIYSASYRYSDVPSRFSGSASGTDFTLTISSVQSEDF ATYYCQQYDSYPYTFGGGTKLEIKSGGGGSEVQLVESGGGLVQP GGSLKLSCAASGFTFNKYAMNWVRQAPGKGLEWVARIRSKYN NYATYYADSVKDRFTISRDDSKNTAYLQMNNLKTEDTAVYYCV RHGNFGNSYISYWAYWGQGTLVTVSSGGGGSGGGGSGGGGSQ TVVTQEPSLTVSPGGTVTLTCGSSTGAVTSGNYPNWVQQKPGQ APRGLIGGTKFLAPGTPARFSGSLLGGKAALTLSGVQPEDEAEYY CVLWYSNRWVFGGGTKLTVLHHHHHH |
| 155 | C00131 | EGFR TriTAC ™ | QVKLEESGGGSVQTGGSLRLTCAASGRTSRSYGMGWFRQAPGK EREFVSGISWRGDSTGYADSVKGRFTISRDNAKNTVDLQMNSLK PEDTAIYYCAAAAGSAWYGTLYEYDYWGQGTQVTVSSGGGGS GGGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSSGGGGSGGGSEVQL VESGGGLVQPGGSLKLSCAASGFTFNKYAMNWVRQAPGKGLE WVARIRSKYNNYATYYADSVKDRFTISRDDSKNTAYLQMNNLK TEDTAVYYCVRHGNFGNSYISYWAYWGQGTLVTVSSGGGGSG GGGSGGGGSQTVVTQEPSLTVSPGGTVTLTCGSSTGAVTSGNYP NWVQQKPGQAPRGLIGGTKFLAPGTPARFSGSLLGGKAALTLSG VQPEDEAEYYCVLWYSNRWVFGGGTKLTVLHHHHHH |
| 156 | C00410 | PSMA Z2 TTriTAC ™ | EVQLVESGGGLVQPGGSLTLSCAASRFMISEYHMHWVRQAPGK GLEWVSTINPAGTTDYAESVKGRFTISRDNAKNTLYLQMNSLRA EDTAVYYCDSYGYRGQGTLVTVSSGGGGSGGGSEVQLVESGGG LVQPGNSLRLSCAASGFTFSKFGMSWVRQAPGKGLEWVSSISGS GRDTLYADSVKGRFTISRDNAKTTLYLQMNSLRPEDTAVYYCTI GGSLSVSSQGTLVTVSSGGGGSGGGSEVQLVESGGGLVQPGGSL KLSCAASGFTFNKYAINWVRQAPGKGLEWVARIRSKYNNYATY YADQVKDRFTISRDDSKNTAYLQMNNLKTEDTAVYYCVRHANF GNSYISYWAYWGQGTLVTVSSGGGGSGGGGSGGGGSQTVVTQ |

TABLE 11-continued

PSMA Targeting Trispecific Protein Sequences

| SEQ ID NO: | C-Number | Construct | Sequence |
|---|---|---|---|
| | | | EPSLTVSPGGTVTLTCASSTGAVTSGNYPNWVQQKPGQAPRGLI GGTKFLVPGTPARFSGSLLGGKAALTLSGVQPEDEAEYYCTLWY SNRWVFGGGTKLTVLHHHHHH |

TABLE 12

Exemplary Framework Sequences

| SEQ ID NO: | Description | Sequence |
|---|---|---|
| 165 | Framework (f1) | EVQLVESGGGLVQPGGSLTLSCAAS |
| 166 | Framework (f2) | WVRQAPGKGLEWVS |
| 167 | Framework (f3) | RFTISRDNAKNTLYLQMNSLRAEDTAVYYC |
| 168 | Framework (f4) | DGYGYRGQGTLVTVSS |

What is claimed is:

1. An isolated single domain antibody that is capable of specifically binding to a PSMA polypeptide comprising SEQ ID No. 20, the single domain antibody comprising complementarity determining regions (CDRs) as follows: (i) a CDR1 comprising the sequence of SEQ ID No. 5, (ii) a CDR2 comprising the sequence of SEQ ID No. 17, and (iii) a CDR3 comprising the sequence of SEQ ID No. 15.

2. The isolated single domain antibody of claim 1, wherein the single domain antibody has the amino acid sequence of SEQ ID No. 32.

3. The isolated single domain antibody of claim 2, wherein said single domain antibody is part of a trispecific protein.

4. The isolated single domain antibody of claim 3, wherein said trispecific protein has the amino acid sequence of SEQ ID No. 153.

5. An isolated polynucleotide encoding the single domain antibody according to claim 1.

6. An isolated vector comprising the polynucleotide of claim 5.

7. An isolated host cell transformed with the vector according to claim 6.

8. A pharmaceutical composition comprising (i) a single domain antibody according to claim 1, and (ii) a pharmaceutically acceptable carrier.

* * * * *

SEQUENCE LISTING

<160> NUMBER OF SEQ ID NOS: 168

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Glu, Pro, Ser, His, Thr, Asp, Gly, Lys, Gln or
      Tyr
<220> FEATURE:
<221> NAME/KEY: MOD_RES
<222> LOCATION: (8)..(8)
<223> OTHER INFORMATION: Glu, Pro, Ser, His, Thr, Asp, Gly, Lys, Gln or
      Tyr

<400> SEQUENCE: 1

Arg Phe Met Ile Ser Xaa Tyr Xaa Met His
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, Pro, Ser, His, Thr, Asp, Gly, Lys, Gln or
      Tyr
<220> FEATURE:
<221> NAME/KEY: MOD_RES
<222> LOCATION: (6)..(7)
<223> OTHER INFORMATION: Glu, Pro, Ser, His, Thr, Asp, Gly, Lys, Gln or
      Tyr
<220> FEATURE:
<221> NAME/KEY: MOD_RES
<222> LOCATION: (13)..(13)
<223> OTHER INFORMATION: Glu, Pro, Ser, His, Thr, Asp, Gly, Lys, Gln or
      Tyr

<400> SEQUENCE: 2

```
Xaa Ile Asn Pro Ala Xaa Xaa Thr Asp Tyr Ala Glu Xaa Val Lys Gly
1               5                   10                  15
```

```
<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu, Pro, Ser, His, Thr, Asp, Gly, Lys, Gln or
      Tyr

<400> SEQUENCE: 3

Asp Xaa Tyr Gly Tyr
1               5
```

```
<210> SEQ ID NO 4
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Gly Tyr Gly Tyr Arg Gly Gln Gly Thr Gln Val Thr Val Ser Ser
            100                 105                 110
```

```
<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Phe Met Ile Ser Glu Tyr His Met His
1               5                   10
```

```
<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

Arg Phe Met Ile Ser Pro Tyr Ser Met His
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Phe Met Ile Ser Pro Tyr His Met His
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Ile Asn Pro Ala Gly Thr Thr Asp Tyr Ala Glu Ser Val Lys Gly
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Ile Asn Pro Ala Lys Thr Thr Asp Tyr Ala Glu Ser Val Lys Gly
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ile Asn Pro Ala Gly Gln Thr Asp Tyr Ala Glu Ser Val Lys Gly
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ile Asn Pro Ala Gly Thr Thr Asp Tyr Ala Glu Tyr Val Lys Gly
1               5                   10                  15

<210> SEQ ID NO 12
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 12

Asp Ile Asn Pro Ala Lys Thr Thr Asp Tyr Ala Glu Ser Val Lys Gly
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ile Asn Pro Ala Gly Gln Thr Asp Tyr Ala Glu Ser Val Lys Gly
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Ile Asn Pro Ala Gly Thr Thr Asp Tyr Ala Glu Tyr Val Lys Gly
1               5                   10                  15

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ser Tyr Gly Tyr
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Phe Met Ile Ser Glu Tyr Ser Met His
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ile Asn Pro Ala Gly Thr Thr Asp Tyr Ala Glu Ser Val Lys Gly
1               5                   10                  15
```

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Gly Tyr Gly Tyr
1               5

<210> SEQ ID NO 19
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Gly Tyr Gly Tyr Arg Gly Gln Gly Thr Leu Val Thr Val Ser Ser
            100                 105                 110

<210> SEQ ID NO 20
<211> LENGTH: 750
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile

```
            115                 120                 125
Ser Ile Ile Asn Glu Asp Gly Asn Glu Ile Phe Asn Thr Ser Leu Phe
        130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540
```

```
Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Val Lys Arg Gln Ile Tyr Val Ala Ala
                725                 730                 735

Phe Thr Val Gln Ala Ala Ala Glu Thr Leu Ser Glu Val Ala
            740                 745                 750

<210> SEQ ID NO 21
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Asp Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser
            100                 105                 110

<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser
            100                 105                 110

<210> SEQ ID NO 23
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Lys Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Pro Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

```
Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                 85                  90                  95

Gly Tyr Gly Tyr Arg Gly Gln Gly Thr Leu Val Thr Val Ser Ser
            100                 105                 110

<210> SEQ ID NO 25
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Leu Val Gln Pro Gly Gly
  1               5                  10                  15

Ser Leu Arg Leu Ser Cys Ala Ala Ser Arg Phe Met Ile Ser Glu Tyr
             20                  25                  30

Ser Met His Trp Val Arg Gln Ala Pro Gly Lys Gly Leu Glu Trp Val
         35                  40                  45

Ser Thr Ile Asn Pro Ala Gly Gln Thr Asp Tyr Ala Glu Ser Val Lys
     50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                 85                  90                  95

Gly Tyr Gly Tyr Arg Gly Gln Gly Thr Leu Val Thr Val Ser Ser
            100                 105                 110

<210> SEQ ID NO 26
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Gln Pro Gly Gly
  1               5                  10                  15

Ser Leu Arg Leu Ser Cys Ala Ala Ser Arg Phe Met Ile Ser Glu Tyr
             20                  25                  30

Ser Met His Trp Val Arg Gln Ala Pro Gly Lys Gly Leu Glu Trp Val
         35                  40                  45

Ser Thr Ile Asn Pro Ala Gly Thr Thr Asp Tyr Ala Glu Tyr Val Lys
     50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                 85                  90                  95

Gly Tyr Gly Tyr Arg Gly Gln Gly Thr Leu Val Thr Val Ser Ser
            100                 105                 110

<210> SEQ ID NO 27
<211> LENGTH: 111
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Asp Ile Asn Pro Ala Lys Thr Thr Asp Tyr Ala Glu Ser Val Lys
50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser
            100                 105                 110

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Pro Tyr
            20                  25                  30

His Met His Trp Val Arg Gln Ala Pro Gly Lys Gly Leu Glu Trp Val
        35                  40                  45

Ser Asp Ile Asn Pro Ala Gly Thr Thr Asp Tyr Ala Glu Ser Val Lys
50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser
            100                 105                 110

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45
```

Ser Asp Ile Asn Pro Ala Gly Gln Thr Asp Tyr Ala Glu Ser Val Lys
            50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser
            100                 105                 110

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
 1               5                   10                  15

Ser Leu Arg Leu Ser Cys Ala Ala Ser Arg Phe Met Ile Ser Glu Tyr
                20                  25                  30

His Met His Trp Val Arg Gln Ala Pro Gly Lys Gly Leu Glu Trp Val
            35                  40                  45

Ser Asp Ile Asn Pro Ala Gly Thr Thr Asp Tyr Ala Glu Tyr Val Lys
            50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser
            100                 105                 110

<210> SEQ ID NO 31
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
 1               5                   10                  15

Ser Leu Thr Leu Ser Cys Ala Ala Ser Arg Phe Met Ile Ser Glu Tyr
                20                  25                  30

His Met His Trp Val Arg Gln Ala Pro Gly Lys Gly Leu Glu Trp Val
            35                  40                  45

Ser Asp Ile Asn Pro Ala Gly Thr Thr Asp Tyr Ala Glu Ser Val Lys
            50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Asp Thr Ala Val Tyr Tyr Cys Asp
                85                  90                  95

Ser Tyr Gly Tyr Arg Gly Gln Gly Thr Gln Val Thr Val Ser Ser
            100                 105                 110

<210> SEQ ID NO 32
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Ser Tyr Gly Tyr Arg Gly Gln Gly Thr Gln Val Thr Val Ser Ser
            100                 105                 110

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
1               5

<210> SEQ ID NO 34
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Ile Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Gln Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Ala Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
```

```
            130                 135                 140
Thr Gln Glu Pro Ser Leu Thr Val Ser Pro Gly Gly Thr Val Thr Leu
145                 150                 155                 160

Thr Cys Ala Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Val Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Thr Leu Trp Tyr Ser Asn Arg Trp Val Phe
225                 230                 235                 240

Gly Gly Gly Thr Lys Leu Thr Val Leu
                245

<210> SEQ ID NO 35
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Glu Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Lys Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Phe Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Asp Asn Arg Trp Val Phe
225                 230                 235                 240
```

Gly Gly Gly Thr Lys Leu Thr Val Leu
            245

<210> SEQ ID NO 36
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser His Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Tyr Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Ser Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Ile Phe
225                 230                 235                 240

Gly Gly Gly Thr Lys Leu Thr Val Leu
            245

<210> SEQ ID NO 37
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Met Phe Asn Lys Tyr
            20                  25                  30

```
Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Thr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Phe Gly Ala Val Thr Ser Gly Asn Tyr Pro Asn
                165                 170                 175

Trp Val Gln Gln Lys Pro Gly Gln Ala Pro Arg Gly Leu Ile Gly
            180                 185                 190

Thr Lys Leu Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Ser Trp Val Phe
225                 230                 235                 240

Gly Gly Gly Thr Lys Leu Thr Val Leu
                245

<210> SEQ ID NO 38
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Lys Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140
```

Thr Gln Glu Pro Ser Leu Thr Val Ser Pro Gly Gly Thr Val Thr Leu
145                 150                 155                 160

Thr Cys Gly Ser Ser Thr Gly Ala Val Val Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Glu Phe Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
        210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 39
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Tyr Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Glu Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Lys Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Glu Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
        210                 215                 220

Glu Ala Glu Tyr Tyr Cys Thr Leu Trp Tyr Ser Asn Arg Trp Val Phe
225                 230                 235                 240

Gly Gly Gly Thr Lys Leu Thr Val Leu

<210> SEQ ID NO 40
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Glu Ser Gly Gly Gly Leu Val Gln Pro Gly Gly
1               5                   10                  15

Ser Leu Lys Leu Ser Cys Ala Ala Ser Gly Asn Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Glu Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Thr Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Tyr Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 41
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val

```
                35                  40                  45
Ala Arg Ile Arg Ser Lys Tyr Asn Asn Tyr Ala Thr Tyr Tyr Ala Asp
            50                  55                  60
Ala Val Lys Asp Arg Phe Thr Ile Ser Arg Asp Asp Ser Lys Asn Thr
65                  70                  75                  80
Ala Tyr Leu Gln Met Asn Asn Leu Lys Thr Glu Asp Thr Ala Val Tyr
                85                  90                  95
Tyr Cys Val Arg His Gly Asn Phe Gly Asn Ser Gln Ile Ser Tyr Trp
            100                 105                 110
Ala Tyr Trp Gly Gln Gly Thr Leu Val Thr Val Ser Ser Gly Gly Gly
        115                 120                 125
Gly Ser Gly Gly Gly Gly Ser Gly Gly Gly Ser Gln Thr Val Val
    130                 135                 140
Thr Gln Glu Pro Ser Leu Thr Val Ser Pro Gly Gly Thr Val Thr Leu
145                 150                 155                 160
Thr Cys Gly Ser Ser Thr Gly Ala Val Thr Asp Gly Asn Tyr Pro Asn
                165                 170                 175
Trp Val Gln Gln Lys Pro Gly Gln Ala Pro Arg Gly Leu Ile Gly Gly
            180                 185                 190
Ile Lys Phe Leu Ala Pro Gly Thr Pro Ala Arg Phe Ser Gly Ser Leu
        195                 200                 205
Leu Gly Gly Lys Ala Ala Leu Thr Leu Ser Gly Val Gln Pro Glu Asp
    210                 215                 220
Glu Ala Glu Tyr Tyr Cys Val Leu Trp Tyr Ser Asn Arg Trp Val Phe
225                 230                 235                 240
Gly Gly Gly Thr Lys Leu Thr Val Leu
                245

<210> SEQ ID NO 42
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Asn Lys Tyr
            20                  25                  30
Ala Val Asn Trp Val Arg Gln Ala Pro Gly Lys Gly Leu Glu Trp Val
        35                  40                  45
Ala Arg Ile Arg Ser Lys Tyr Asn Asn Tyr Ala Thr Tyr Tyr Ala Asp
    50                  55                  60
Ser Val Lys Asp Arg Phe Thr Ile Ser Arg Asp Asp Ser Lys Asn Thr
65                  70                  75                  80
Ala Tyr Leu Gln Met Asn Asn Leu Lys Thr Glu Asp Thr Ala Val Tyr
                85                  90                  95
Tyr Cys Val Arg His Gly Asn Phe Gly Asn Ser Tyr Ile Ser Tyr Trp
            100                 105                 110
Ala Tyr Trp Gly Gln Gly Thr Leu Val Thr Val Ser Ser Gly Gly Gly
        115                 120                 125
Gly Ser Gly Gly Gly Gly Ser Gly Gly Gly Gly Ser Gln Thr Val Val
    130                 135                 140
```

```
Thr Gln Glu Pro Ser Leu Thr Val Ser Pro Gly Gly Thr Val Thr Leu
145                 150                 155                 160

Thr Cys Gly Glu Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Ile Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
            210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 43
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
                20                  25                  30

Pro Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Asn Glu Asp Thr Ala Val Tyr
                85                  90                  95

Tyr Cys Val Arg His Gly Asn Phe Asn Asn Ser Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
            130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Lys Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Met Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
            210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
                245
```

<210> SEQ ID NO 44
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Gly Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Glu Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Val Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Glu Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 45
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Lys Leu Ser Cys Ala Ala Ser Gly Asn Thr Phe Asn Lys Tyr
            20                  25                  30

Ala Met Asn Trp Val Arg Gln Ala Pro Gly Lys Gly Leu Glu Trp Val
        35                  40                  45

```
Ala Arg Ile Arg Ser Lys Tyr Asn Asn Tyr Ala Thr Tyr Tyr Ala Asp
            50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                    85                  90                  95

Tyr Cys Val Arg His Gly Asn Phe Gly Asp Ser Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
            130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr His Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Val Leu Ala Pro Gly Thr Pro Ala Arg Phe Ser Gly Ser Leu
                195                 200                 205

Leu Gly Gly Lys Ala Ala Leu Thr Leu Ser Gly Val Gln Pro Glu Asp
            210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 46
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Asn Tyr
                20                  25                  30

Ala Met Asn Trp Val Arg Gln Ala Pro Gly Lys Gly Leu Glu Trp Val
            35                  40                  45

Ala Arg Ile Arg Ser Gly Tyr Asn Asn Tyr Ala Thr Tyr Tyr Ala Asp
            50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                    85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
            130                 135                 140

Thr Gln Glu Pro Ser Leu Thr Val Ser Pro Gly Gly Thr Val Thr Leu
```

-continued

```
            145                 150                 155                 160
Thr Cys Gly Ser Tyr Thr Gly Ala Val Thr Ser Gly Asn Tyr Pro Asn
                165                 170                 175
Trp Val Gln Gln Lys Pro Gly Gln Ala Pro Arg Gly Leu Ile Gly Gly
                180                 185                 190
Thr Lys Phe Asn Ala Pro Gly Thr Pro Ala Arg Phe Ser Gly Ser Leu
                195                 200                 205
Leu Gly Gly Lys Ala Ala Leu Thr Leu Ser Gly Val Gln Pro Glu Asp
                210                 215                 220
Glu Ala Glu Tyr Tyr Cys Val Leu Trp Tyr Ala Asn Arg Trp Val Phe
225                 230                 235                 240
Gly Gly Gly Thr Lys Leu Thr Val Leu
                245

<210> SEQ ID NO 47
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Glu Phe Asn Lys Tyr
                20                  25                  30
Ala Met Asn Trp Val Arg Gln Ala Pro Gly Lys Gly Leu Glu Trp Val
                35                  40                  45
Ala Arg Ile Arg Ser Lys Tyr Asn Asn Tyr Glu Thr Tyr Tyr Ala Asp
            50                  55                  60
Ser Val Lys Asp Arg Phe Thr Ile Ser Arg Asp Asp Ser Lys Asn Thr
65              70                  75                  80
Ala Tyr Leu Gln Met Asn Asn Leu Lys Thr Glu Asp Thr Ala Val Tyr
                85                  90                  95
Tyr Cys Val Arg His Gly Asn Phe Gly Asn Ser Leu Ile Ser Tyr Trp
                100                 105                 110
Ala Tyr Trp Gly Gln Gly Thr Leu Val Thr Val Ser Ser Gly Gly Gly
                115                 120                 125
Gly Ser Gly Gly Gly Gly Ser Gly Gly Gly Gly Ser Gln Thr Val Val
130                 135                 140
Thr Gln Glu Pro Ser Leu Thr Val Ser Pro Gly Gly Thr Val Thr Leu
145                 150                 155                 160
Thr Cys Gly Ser Ser Ser Gly Ala Val Thr Ser Gly Asn Tyr Pro Asn
                165                 170                 175
Trp Val Gln Gln Lys Pro Gly Gln Ala Pro Arg Gly Leu Ile Gly Gly
                180                 185                 190
Thr Lys Phe Gly Ala Pro Gly Thr Pro Ala Arg Phe Ser Gly Ser Leu
                195                 200                 205
Leu Gly Gly Lys Ala Ala Leu Thr Leu Ser Gly Val Gln Pro Glu Asp
                210                 215                 220
Glu Ala Glu Tyr Tyr Cys Val Leu Trp Tyr Ser Asn Arg Trp Val Phe
225                 230                 235                 240
Gly Gly Gly Thr Lys Leu Thr Val Leu
                245
```

-continued

```
<210> SEQ ID NO 48
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Thr Phe Asn Lys Tyr Ala Met Asn
1               5                   10

<210> SEQ ID NO 50
<211> LENGTH: 18
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 50

Arg Ile Arg Ser Lys Tyr Asn Asn Tyr Ala Thr Tyr Tyr Ala Asp Ser
1               5                   10                  15

Val Lys

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Gly Asn Phe Gly Asn Ser Tyr Ile Ser Tyr Trp Ala Tyr
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Pro Glu Thr Gly
1               5

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ser Ser Thr Gly Ala Val Thr Ser Gly Asn Tyr Pro Asn
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Thr Lys Phe Leu Ala Pro
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Leu Trp Tyr Ser Asn Arg Trp Val
1               5

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Asn Thr Phe Asn Lys Tyr Ala Met Asn
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Phe Glu Phe Asn Lys Tyr Ala Met Asn
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Phe Met Phe Asn Lys Tyr Ala Met Asn
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Phe Thr Tyr Asn Lys Tyr Ala Met Asn
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Phe Thr Phe Asn Asn Tyr Ala Met Asn
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 61

Gly Phe Thr Phe Asn Gly Tyr Ala Met Asn
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Phe Thr Phe Asn Thr Tyr Ala Met Asn
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Phe Thr Phe Asn Glu Tyr Ala Met Asn
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Phe Thr Phe Asn Lys Tyr Pro Met Asn
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Phe Thr Phe Asn Lys Tyr Ala Val Asn
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Phe Thr Phe Asn Lys Tyr Ala Ile Asn
1               5                   10

<210> SEQ ID NO 67
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Phe Thr Phe Asn Lys Tyr Ala Leu Asn
1               5                   10

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Ile Arg Ser Gly Tyr Asn Asn Tyr Ala Thr Tyr Tyr Ala Asp Ser
1               5                   10                  15

Val Lys

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ile Arg Ser Lys Ser Asn Asn Tyr Ala Thr Tyr Tyr Ala Asp Ser
1               5                   10                  15

Val Lys

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Ile Arg Ser Lys Tyr Asn Lys Tyr Ala Thr Tyr Tyr Ala Asp Ser
1               5                   10                  15

Val Lys

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Ile Arg Ser Lys Tyr Asn Asn Tyr Glu Thr Tyr Tyr Ala Asp Ser
1               5                   10                  15

Val Lys

<210> SEQ ID NO 72
<211> LENGTH: 18
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 72

Arg Ile Arg Ser Lys Tyr Asn Asn Tyr Ala Thr Glu Tyr Ala Asp Ser
1               5                   10                  15

Val Lys

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ile Arg Ser Lys Tyr Asn Asn Tyr Ala Thr Tyr Tyr Lys Asp Ser
1               5                   10                  15

Val Lys

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ile Arg Ser Lys Tyr Asn Asn Tyr Ala Thr Tyr Tyr Ala Asp Glu
1               5                   10                  15

Val Lys

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ile Arg Ser Lys Tyr Asn Asn Tyr Ala Thr Tyr Tyr Ala Asp Ala
1               5                   10                  15

Val Lys

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ile Arg Ser Lys Tyr Asn Asn Tyr Ala Thr Tyr Tyr Ala Asp Gln
1               5                   10                  15

Val Lys

<210> SEQ ID NO 77
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Ile Arg Ser Lys Tyr Asn Asn Tyr Ala Thr Tyr Tyr Ala Asp Asp
1               5                   10                  15

Val Lys

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

His Ala Asn Phe Gly Asn Ser Tyr Ile Ser Tyr Trp Ala Tyr
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

His Thr Asn Phe Gly Asn Ser Tyr Ile Ser Tyr Trp Ala Tyr
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

His Gly Asn Phe Asn Asn Ser Tyr Ile Ser Tyr Trp Ala Tyr
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

His Gly Asn Phe Gly Asp Ser Tyr Ile Ser Tyr Trp Ala Tyr
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82
```

```
His Gly Asn Phe Gly Asn Ser His Ile Ser Tyr Trp Ala Tyr
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Gly Asn Phe Gly Asn Ser Pro Ile Ser Tyr Trp Ala Tyr
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

His Gly Asn Phe Gly Asn Ser Gln Ile Ser Tyr Trp Ala Tyr
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

His Gly Asn Phe Gly Asn Ser Leu Ile Ser Tyr Trp Ala Tyr
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

His Gly Asn Phe Gly Asn Ser Gly Ile Ser Tyr Trp Ala Tyr
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

His Gly Asn Phe Gly Asn Ser Tyr Ile Ser Tyr Trp Ala Thr
1               5                   10

<210> SEQ ID NO 88
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 88

Ala Ser Ser Thr Gly Ala Val Thr Ser Gly Asn Tyr Pro Asn
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Glu Ser Thr Gly Ala Val Thr Ser Gly Asn Tyr Pro Asn
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Ser Tyr Thr Gly Ala Val Thr Ser Gly Asn Tyr Pro Asn
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Ser Ser Phe Gly Ala Val Thr Ser Gly Asn Tyr Pro Asn
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ser Ser Lys Gly Ala Val Thr Ser Gly Asn Tyr Pro Asn
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ser Ser Ser Gly Ala Val Thr Ser Gly Asn Tyr Pro Asn
1               5                   10
```

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Ser Ser Thr Gly Tyr Val Thr Ser Gly Asn Tyr Pro Asn
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ser Ser Thr Gly Ala Val Val Ser Gly Asn Tyr Pro Asn
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Ser Ser Thr Gly Ala Val Thr Asp Gly Asn Tyr Pro Asn
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Ser Ser Thr Gly Ala Val Thr Lys Gly Asn Tyr Pro Asn
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ser Ser Thr Gly Ala Val Thr His Gly Asn Tyr Pro Asn
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 99

Gly Ser Ser Thr Gly Ala Val Thr Val Gly Asn Tyr Pro Asn
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Ser Ser Thr Gly Ala Val Thr Ser Gly Tyr Tyr Pro Asn
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ile Lys Phe Leu Ala Pro
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Thr Glu Phe Leu Ala Pro
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Thr Tyr Phe Leu Ala Pro
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Thr Ser Phe Leu Ala Pro
1               5

<210> SEQ ID NO 105
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 105

Gly Thr Asn Phe Leu Ala Pro
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Thr Lys Leu Leu Ala Pro
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Thr Lys Glu Leu Ala Pro
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Thr Lys Ile Leu Ala Pro
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Thr Lys Met Leu Ala Pro
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Thr Lys Val Leu Ala Pro
1               5
```

```
<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Thr Lys Phe Asn Ala Pro
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Thr Lys Phe Gly Ala Pro
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Thr Lys Phe Leu Val Pro
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Leu Trp Tyr Ser Asn Arg Trp Val
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Leu Trp Tyr Ser Asn Arg Trp Val
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 116

Val Leu Trp Tyr Asp Asn Arg Trp Val
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Val Leu Trp Tyr Ala Asn Arg Trp Val
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Val Leu Trp Tyr Ser Asn Ser Trp Val
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Val Leu Trp Tyr Ser Asn Arg Trp Ile
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Val Leu Trp Tyr Ser Asn Arg Trp Ala
1               5

<210> SEQ ID NO 121
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30
```

```
Ala Leu Asn Trp Val Arg Gln Ala Pro Gly Lys Gly Leu Glu Trp Val
         35                  40                  45

Ala Arg Ile Arg Ser Lys Tyr Asn Asn Tyr Ala Thr Glu Tyr Ala Asp
     50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
             85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Asn Phe Leu Ala Pro Gly Thr Pro Glu Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Ala Phe
225                 230                 235                 240

Gly Gly Gly Thr Lys Leu Thr Val Leu
                245

<210> SEQ ID NO 122
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Thr Phe Asn Glu Tyr
             20                  25                  30

Ala Met Asn Trp Val Arg Gln Ala Pro Gly Lys Gly Leu Glu Trp Val
         35                  40                  45

Ala Arg Ile Arg Ser Lys Tyr Asn Asn Tyr Ala Thr Tyr Tyr Ala Asp
     50                  55                  60

Asp Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
             85                  90                  95

Tyr Cys Val Arg His Gly Asn Phe Gly Asn Ser Gly Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140
```

```
Thr Gln Glu Pro Ser Leu Thr Val Ser Pro Gly Gly Thr Val Thr Leu
145                 150                 155                 160

Thr Cys Gly Ser Ser Thr Gly Ala Val Thr Val Gly Asn Tyr Pro Asn
                165                 170                 175

Trp Val Gln Gln Lys Pro Gly Gln Ala Pro Arg Gly Leu Ile Gly Gly
            180                 185                 190

Thr Glu Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 123
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 124
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ala Asp Thr Leu Tyr Ala Asp Ser Leu
    50                  55                  60
```

```
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Lys Ser Ser Gln Gly Thr Leu Val Thr
            100                 105                 110

Val Ser Ser
        115

<210> SEQ ID NO 125
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Glu Ser Gly Gly Gly Leu Val Gln Pro Gly Asn
  1               5                  10                  15

Ser Leu Arg Leu Ser Cys Ala Ala Ser Gly Phe Thr Tyr Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Lys Ser Ser Gln Gly Thr Leu Val Thr
            100                 105                 110

Val Ser Ser
        115

<210> SEQ ID NO 126
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Val Glu Ser Gly Gly Gly Leu Val Gln Pro Gly Asn
  1               5                  10                  15

Ser Leu Arg Leu Ser Cys Ala Ala Ser Gly Phe Thr Phe Ser Lys Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Thr Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110
```

```
Val Ser Ser
        115

<210> SEQ ID NO 127
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Lys Ser Ser Gln Gly Thr Leu Val Thr
            100                 105                 110

Val Ser Ser
        115

<210> SEQ ID NO 128
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser
        115

<210> SEQ ID NO 129
<211> LENGTH: 115
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 129

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Phe Thr Phe Ser Ser Phe Gly Met Ser
1               5                   10

<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Ile Ser Gly Ser Gly Ser Asp Thr Leu Tyr Ala Asp Ser Val Lys
1               5                   10                  15

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Gly Ser Leu Ser Arg
1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 133

Gly Phe Thr Phe Ser Arg Phe Gly Met Ser
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Phe Thr Phe Ser Lys Phe Gly Met Ser
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Phe Thr Tyr Ser Ser Phe Gly Met Ser
1               5                   10

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Ile Ser Gly Ser Gly Ala Asp Thr Leu Tyr Ala Asp Ser Leu Lys
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Ile Ser Gly Ser Gly Thr Asp Thr Leu Tyr Ala Asp Ser Val Lys
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Ile Ser Gly Ser Gly Arg Asp Thr Leu Tyr Ala Asp Ser Val Lys
1               5                   10                  15

<210> SEQ ID NO 139

<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Ile Ser Gly Ser Gly Ser Asp Thr Leu Tyr Ala Glu Ser Val Lys
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ser Ile Ser Gly Ser Gly Thr Asp Thr Leu Tyr Ala Glu Ser Val Lys
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Ile Ser Gly Ser Gly Arg Asp Thr Leu Tyr Ala Glu Ser Val Lys
1               5                   10                  15

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Gly Ser Leu Ser Lys
1               5

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gly Ser Leu Ser Val
1               5

<210> SEQ ID NO 144
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 145
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Thr Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 146
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45
```

Ser Ser Ile Ser Gly Ser Gly Arg Asp Thr Leu Tyr Ala Glu Ser Val
    50              55                  60

Lys Gly Arg Phe Thr Ile Ser Arg Asp Asn Ala Lys Thr Thr Leu Tyr
65              70                  75                  80

Leu Gln Met Asn Ser Leu Arg Pro Glu Asp Thr Ala Val Tyr Tyr Cys
            85                  90                  95

Thr Ile Gly Gly Ser Leu Ser Val Ser Ser Gln Gly Thr Leu Val Thr
            100                 105                 110

Val Ser Ser
        115

<210> SEQ ID NO 147
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Gly Tyr Gly Tyr Arg Gly Gln Gly Thr Gln Val Thr Val Ser Ser Gly
            100                 105                 110

Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

```
Leu Glu Trp Val Ala Arg Ile Arg Ser Lys Tyr Asn Asn Tyr Ala Thr
        290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
                340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
                420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 148
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
                20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Gly Tyr Gly Tyr Arg Gly Gln Gly Thr Gln Val Thr Val Ser Ser Gly
                100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140
```

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
            165                 170                 175

Asp Thr Leu Tyr Ala Asp Ser Val Lys Gly Arg Phe Thr Ile Ser Arg
        180                 185                 190

Asp Asn Ala Lys Thr Thr Leu Tyr Leu Gln Met Asn Ser Leu Arg Pro
    195                 200                 205

Glu Asp Thr Ala Val Tyr Tyr Cys Thr Ile Gly Gly Ser Leu Ser Val
210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
            245                 250                 255

Gln Pro Gly Gly Ser Leu Lys Leu Ser Cys Ala Ala Ser Gly Phe Thr
        260                 265                 270

Phe Asn Asn Tyr Ala Met Asn Trp Val Arg Gln Ala Pro Gly Lys Gly
    275                 280                 285

Leu Glu Trp Val Ala Arg Ile Arg Ser Gly Tyr Asn Asn Tyr Ala Thr
290                 295                 300

Tyr Tyr Ala Asp Ser Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
            325                 330                 335

Thr Ala Val Tyr Tyr Cys Val Arg His Gly Asn Phe Gly Asn Ser Tyr
        340                 345                 350

Ile Ser Tyr Trp Ala Tyr Trp Gly Gln Gly Thr Leu Val Thr Val Ser
    355                 360                 365

Ser Gly Gly Gly Gly Ser Gly Gly Gly Ser Gly Gly Gly Gly Ser
370                 375                 380

Gln Thr Val Val Thr Gln Glu Pro Ser Leu Thr Val Ser Pro Gly Gly
385                 390                 395                 400

Thr Val Thr Leu Thr Cys Gly Ser Tyr Thr Gly Ala Val Thr Ser Gly
            405                 410                 415

Asn Tyr Pro Asn Trp Val Gln Gln Lys Pro Gly Gln Ala Pro Arg Gly
        420                 425                 430

Leu Ile Gly Gly Thr Lys Phe Asn Ala Pro Gly Thr Pro Ala Arg Phe
    435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Val Leu Trp Tyr Ala Asn
465                 470                 475                 480

Arg Trp Val Phe Gly Gly Gly Thr Lys Leu Thr Val Leu His His His
            485                 490                 495

His His His

<210> SEQ ID NO 149
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

-continued

```
Glu Val Gln Leu Val Glu Ser Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Gly Tyr Gly Tyr Arg Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Glu
            260                 265                 270

Phe Asn Lys Tyr Ala Met Asn Trp Val Arg Gln Ala Pro Gly Lys Gly
        275                 280                 285

Leu Glu Trp Val Ala Arg Ile Arg Ser Lys Tyr Asn Asn Tyr Glu Thr
    290                 295                 300

Tyr Tyr Ala Asp Ser Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Gly Asn Phe Gly Asn Ser Leu
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Gly Ser Ser Gly Ala Val Thr Ser Gly
                405                 410                 415
```

```
Asn Tyr Pro Asn Trp Val Gln Gln Lys Pro Gly Gln Ala Pro Arg Gly
                420                 425                 430

Leu Ile Gly Gly Thr Lys Phe Gly Ala Pro Gly Thr Pro Ala Arg Phe
            435                 440                 445

Ser Gly Ser Leu Leu Gly Gly Lys Ala Ala Leu Thr Leu Ser Gly Val
        450                 455                 460

Gln Pro Glu Asp Glu Ala Glu Tyr Tyr Cys Val Leu Trp Tyr Ser Asn
465                 470                 475                 480

Arg Trp Val Phe Gly Gly Thr Lys Leu Thr Val Leu His His His
                485                 490                 495

His His His

<210> SEQ ID NO 150
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Gly Tyr Gly Tyr Arg Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Ser Phe Gly Met Ser Trp Val Arg Gln Ala
145                 150                 155                 160

Pro Gly Lys Gly Leu Glu Trp Val Ser Ser Ile Ser Gly Ser Gly Ser
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Arg
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270
```

```
Phe Asn Lys Tyr Ala Met Asn Trp Val Arg Gln Ala Pro Gly Lys Gly
            275                 280                 285

Leu Glu Trp Val Ala Arg Ile Arg Ser Lys Tyr Asn Asn Tyr Ala Thr
        290                 295                 300

Tyr Tyr Ala Asp Ser Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Gly Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Gly Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Ala Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Val Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 151
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Gly Tyr Gly Tyr Arg Gly Gln Gly Thr Leu Val Thr Val Ser Ser Gly
            100                 105                 110

Gly Gly Gly Ser Gly Gly Gly Ser Glu Val Gln Leu Val Glu Ser Gly
        115                 120                 125
```

```
Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
                180                 185                 190

Asp Asn Ala Lys Thr Thr Leu Tyr Leu Gln Met Asn Ser Leu Arg Pro
            195                 200                 205

Glu Asp Thr Ala Val Tyr Tyr Cys Thr Ile Gly Gly Ser Leu Ser Val
210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
                260                 265                 270

Phe Asn Lys Tyr Ala Ile Asn Trp Val Arg Gln Ala Pro Gly Lys Gly
            275                 280                 285

Leu Glu Trp Val Ala Arg Ile Arg Ser Lys Tyr Asn Asn Tyr Ala Thr
290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
                340                 345                 350

Ile Ser Tyr Trp Ala Tyr Trp Gly Gln Gly Thr Leu Val Thr Val Ser
            355                 360                 365

Ser Gly Gly Gly Gly Ser Gly Gly Gly Ser Gly Gly Gly Gly Ser
370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His
                485                 490                 495

His His His

<210> SEQ ID NO 152
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 152

```
Glu Val Gln Leu Val Glu Ser Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Asp Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Ser Tyr Gly Tyr Arg Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
```

```
                    405                 410                 415
Asn Tyr Pro Asn Trp Val Gln Gln Lys Pro Gly Gln Ala Pro Arg Gly
                420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 153
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Glu Tyr
            20                  25                  30

His Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Ser Tyr Gly Tyr Arg Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Gly Gly Gly Gly Ser
225                 230                 235                 240

Gly Gly Gly Ser Glu Val Gln Leu Val Glu Ser Gly Gly Leu Val
                245                 250                 255

Gln Pro Gly Gly Ser Leu Lys Leu Ser Cys Ala Ala Ser Gly Phe Thr
```

```
                     260                 265                 270
        Phe Asn Lys Tyr Ala Ile Asn Trp Val Arg Gln Ala Pro Gly Lys Gly
                    275                 280                 285

Leu Glu Trp Val Ala Arg Ile Arg Ser Lys Tyr Asn Asn Tyr Ala Thr
                    290                 295                 300

Tyr Tyr Ala Asp Gln Val Lys Asp Arg Phe Thr Ile Ser Arg Asp Asp
        305                 310                 315                 320

Ser Lys Asn Thr Ala Tyr Leu Gln Met Asn Asn Leu Lys Thr Glu Asp
                        325                 330                 335

Thr Ala Val Tyr Tyr Cys Val Arg His Ala Asn Phe Gly Asn Ser Tyr
                        340                 345                 350

Ile Ser Tyr Trp Ala Tyr Trp Gly Gln Gly Thr Leu Val Thr Val Ser
                        355                 360                 365

Ser Gly Gly Gly Gly Ser Gly Gly Gly Gly Ser Gly Gly Gly Gly Ser
                    370                 375                 380

Gln Thr Val Val Thr Gln Glu Pro Ser Leu Thr Val Ser Pro Gly Gly
        385                 390                 395                 400

Thr Val Thr Leu Thr Cys Ala Ser Ser Thr Gly Ala Val Thr Ser Gly
                        405                 410                 415

Asn Tyr Pro Asn Trp Val Gln Gln Lys Pro Gly Gln Ala Pro Arg Gly
                        420                 425                 430

Leu Ile Gly Gly Thr Lys Phe Leu Val Pro Gly Thr Pro Ala Arg Phe
                        435                 440                 445

Ser Gly Ser Leu Leu Gly Gly Lys Ala Ala Leu Thr Leu Ser Gly Val
                    450                 455                 460

Gln Pro Glu Asp Glu Ala Glu Tyr Tyr Cys Thr Leu Trp Tyr Ser Asn
        465                 470                 475                 480

Arg Trp Val Phe Gly Gly Gly Thr Lys Leu Thr Val Leu His His His
                        485                 490                 495

His His His
```

<210> SEQ ID NO 154
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
        Gln Val Gln Leu Val Glu Ser Gly Gly Gly Leu Val Lys Pro Gly Glu
        1               5                   10                  15

Ser Leu Arg Leu Ser Cys Ala Ala Ser Gly Phe Thr Phe Ser Asp Tyr
                        20                  25                  30

Tyr Met Tyr Trp Val Arg Gln Ala Pro Gly Lys Gly Leu Glu Trp Val
                    35                  40                  45

Ala Ile Ile Ser Asp Gly Gly Tyr Tyr Thr Tyr Ser Asp Ile Ile
                50                  55                  60

Lys Gly Arg Phe Thr Ile Ser Arg Asp Asn Ala Lys Asn Ser Leu Tyr
        65                  70                  75                  80

Leu Gln Met Asn Ser Leu Lys Ala Glu Asp Thr Ala Val Tyr Tyr Cys
                        85                  90                  95

Ala Arg Gly Phe Pro Leu Leu Arg His Gly Ala Met Asp Tyr Trp Gly
                        100                 105                 110

Gln Gly Thr Leu Val Thr Val Ser Ser Gly Gly Gly Gly Ser Gly Gly
```

```
            115                 120                 125
Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Lys Pro
                165                 170                 175

Gly Gln Ala Pro Lys Ser Leu Ile Tyr Ser Ala Ser Tyr Arg Tyr Ser
                180                 185                 190

Asp Val Pro Ser Arg Phe Ser Gly Ser Ala Ser Gly Thr Asp Phe Thr
                195                 200                 205

Leu Thr Ile Ser Ser Val Gln Ser Glu Asp Phe Ala Thr Tyr Tyr Cys
    210                 215                 220

Gln Gln Tyr Asp Ser Tyr Pro Tyr Thr Phe Gly Gly Gly Thr Lys Leu
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
                260                 265                 270

Ala Ser Gly Phe Thr Phe Asn Lys Tyr Ala Met Asn Trp Val Arg Gln
    275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
                340                 345                 350

Phe Gly Asn Ser Tyr Ile Ser Tyr Trp Ala Tyr Trp Gly Gln Gly Thr
    355                 360                 365

Leu Val Thr Val Ser Ser Gly Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
                420                 425                 430

Gln Ala Pro Arg Gly Leu Ile Gly Gly Thr Lys Phe Leu Ala Pro Gly
                435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu His His His His His His
            500

<210> SEQ ID NO 155
<211> LENGTH: 512
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 155

```
Gln Val Lys Leu Glu Glu Ser Gly Gly Gly Ser Val Gln Thr Gly Gly
1               5                   10                  15

Ser Leu Arg Leu Thr Cys Ala Ala Ser Gly Arg Thr Ser Arg Ser Tyr
            20                  25                  30

Gly Met Gly Trp Phe Arg Gln Ala Pro Gly Lys Glu Arg Glu Phe Val
        35                  40                  45

Ser Gly Ile Ser Trp Arg Gly Asp Ser Thr Gly Tyr Ala Asp Ser Val
    50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Ala Trp Tyr Gly Thr Leu Tyr Glu Tyr Asp
            100                 105                 110

Tyr Trp Gly Gln Gly Thr Gln Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
    210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Gly Gly Gly Gly Ser Gly Gly Gly
                245                 250                 255

Ser Glu Val Gln Leu Val Glu Ser Gly Gly Gly Leu Val Gln Pro Gly
            260                 265                 270

Gly Ser Leu Lys Leu Ser Cys Ala Ala Ser Gly Phe Thr Phe Asn Lys
        275                 280                 285

Tyr Ala Met Asn Trp Val Arg Gln Ala Pro Gly Lys Gly Leu Glu Trp
    290                 295                 300

Val Ala Arg Ile Arg Ser Lys Tyr Asn Asn Tyr Ala Thr Tyr Tyr Ala
305                 310                 315                 320

Asp Ser Val Lys Asp Arg Phe Thr Ile Ser Arg Asp Asp Ser Lys Asn
                325                 330                 335

Thr Ala Tyr Leu Gln Met Asn Asn Leu Lys Thr Glu Asp Thr Ala Val
            340                 345                 350

Tyr Tyr Cys Val Arg His Gly Asn Phe Gly Asn Ser Tyr Ile Ser Tyr
        355                 360                 365

Trp Ala Tyr Trp Gly Gln Gly Thr Leu Val Thr Val Ser Ser Gly Gly
    370                 375                 380

Gly Gly Ser Gly Gly Gly Gly Ser Gly Gly Gly Gly Ser Gln Thr Val
```

```
385                 390                 395                 400
Val Thr Gln Glu Pro Ser Leu Thr Val Ser Pro Gly Gly Thr Val Thr
                405                 410                 415

Leu Thr Cys Gly Ser Ser Thr Gly Ala Val Thr Ser Gly Asn Tyr Pro
            420                 425                 430

Asn Trp Val Gln Gln Lys Pro Gly Gln Ala Pro Arg Gly Leu Ile Gly
        435                 440                 445

Gly Thr Lys Phe Leu Ala Pro Gly Thr Pro Ala Arg Phe Ser Gly Ser
    450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Val Leu Trp Tyr Ser Asn Arg Trp Val
                485                 490                 495

Phe Gly Gly Gly Thr Lys Leu Thr Val Leu His His His His His His
            500                 505                 510

<210> SEQ ID NO 156
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240
```

```
Gly Gly Gly Ser Glu Val Gln Leu Val Glu Ser Gly Gly Gly Leu Val
            245                 250                 255

Gln Pro Gly Gly Ser Leu Lys Leu Ser Cys Ala Ala Ser Gly Phe Thr
        260                 265                 270

Phe Asn Lys Tyr Ala Ile Asn Trp Val Arg Gln Ala Pro Gly Lys Gly
            275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His
                485                 490                 495

His His His

<210> SEQ ID NO 157
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-10 "Gly Ser"
      repeating units

<400> SEQUENCE: 157

Gly Ser Gly Ser Gly Ser Gly Ser Gly Ser Gly Ser Gly Ser Gly Ser
1               5                   10                  15

Gly Ser Gly Ser
            20

<210> SEQ ID NO 158
<211> LENGTH: 30
<212> TYPE: PRT
<213> ORGANISM: Artificial Sequence
<220> FEATURE:
<223> OTHER INFORMATION: Description of Artificial Sequence: Synthetic
```

```
      polypeptide
<220> FEATURE:
<221> NAME/KEY: MISC_FEATURE
<222> LOCATION: (1)..(30)
<223> OTHER INFORMATION: This sequence may encompass 1-10 "Gly Gly Ser"
      repeating units

<400> SEQUENCE: 158

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 159
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units

<400> SEQUENCE: 159

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 160
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Ser
      Gly" repeating units

<400> SEQUENCE: 160

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 161
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Ser
      Gly Gly" repeating units
```

```
<400> SEQUENCE: 161

Gly Gly Ser Gly Gly Gly Gly Ser Gly Gly Gly Ser Gly Gly
1               5                   10                  15

Gly Ser Gly Gly Gly Gly Ser Gly Gly Gly Ser Gly Gly Gly
            20                  25                  30

Ser Gly Gly Gly Gly Ser Gly Gly Gly Ser Gly Gly Gly Ser
        35                  40                  45

Gly Gly
    50

<210> SEQ ID NO 162
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units

<400> SEQUENCE: 162

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly
        35                  40                  45

Gly Ser
    50

<210> SEQ ID NO 163
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Gly Gly Gly Ser Gly Gly Gly Gly Ser Gly Gly Gly Ser Gly
1               5                   10                  15

Gly Gly Gly Ser
            20

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Gly Gly Gly Ser Gly Gly Gly Gly Ser Gly Gly Gly Gly Ser
1               5                   10                  15

<210> SEQ ID NO 165
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 165

Glu Val Gln Leu Val Glu Ser Gly Gly Gly Leu Val Gln Pro Gly Gly
1               5                   10                  15

Ser Leu Thr Leu Ser Cys Ala Ala Ser
            20                  25

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Trp Val Arg Gln Ala Pro Gly Lys Gly Leu Glu Trp Val Ser
1               5                   10

<210> SEQ ID NO 167
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asp Gly Tyr Gly Tyr Arg Gly Gln Gly Thr Leu Val Thr Val Ser Ser
1               5                   10                  15
```